(12) United States Patent
Roberts

(10) Patent No.: US 6,601,055 B1
(45) Date of Patent: Jul. 29, 2003

(54) EXPLANATION GENERATION SYSTEM FOR A DIAGNOSIS SUPPORT TOOL EMPLOYING AN INFERENCE SYSTEM

(76) Inventor: Linda M. Roberts, 4134 N. 89th St., Milwaukee, WI (US) 53222

( * ) Notice: Subject to any disclaimer, the term of this patent is extended or adjusted under 35 U.S.C. 154(b) by 0 days.

(21) Appl. No.: 09/366,482

(22) Filed: Aug. 2, 1999

Related U.S. Application Data

(63) Continuation-in-part of application No. 08/998,494, filed on Dec. 26, 1997, now Pat. No. 6,056,690.
(60) Provisional application No. 60/034,383, filed on Dec. 27, 1996.

(51) Int. Cl.[7] .................................................. G06N 5/02
(52) U.S. Cl. ........................ 706/45; 600/300; 704/257
(58) Field of Search .............................. 706/45; 705/3; 704/257; 600/300

(56) References Cited

U.S. PATENT DOCUMENTS

| | | | | |
|---|---|---|---|---|
| 5,594,638 A | * | 1/1997 | Iliff ................................ 705/3 |
| 5,660,176 A | * | 8/1997 | Iliff ............................. 600/300 |
| 5,692,220 A | | 11/1997 | Diamond et al. ........... 600/368 |
| 5,711,297 A | * | 1/1998 | Iliff ............................. 600/300 |
| 5,724,968 A | * | 3/1998 | Iliff ............................. 600/300 |
| 5,800,347 A | | 9/1998 | Skates et al. ............... 600/300 |
| 5,839,106 A | * | 11/1998 | Bellegarda ................. 704/257 |
| 5,868,669 A | * | 2/1999 | Iliff ............................. 600/300 |
| 5,910,107 A | * | 6/1999 | Iliff ............................. 600/300 |
| 6,022,315 A | * | 2/2000 | Iliff ............................. 600/300 |
| 6,113,540 A | * | 9/2000 | Iliff ............................. 600/330 |

* cited by examiner

Primary Examiner—Wilbert L. Starks, Jr.
(74) Attorney, Agent, or Firm—Dorsey & Whitney LLP

(57) ABSTRACT

An interactive multimodal explanation generation system for a computer-aided decision support tool employing an inference system is disclosed. The explanation generation system includes a user interface enhanced with a reasoning component that allows a user to ask, using mouse clicks and natural language text, the system questions about her health and about how the system is constructed. The explanation generation system produces interactive multimodal explanations (using textual displays, graphics, animation, or a combination of these) for the results generated by the inference system in the diagnostic support tool.

10 Claims, 52 Drawing Sheets

| P(X\|Y) | $y_1$ | $y_2$ | $y_3$ |
|---|---|---|---|
| $x_1$ | $p(x_1 \| y_1)$ | $p(x_1 \| y_2)$ | $p(x_1 \| y_3)$ |
| $x_2$ | $p(x_2 \| y_1)$ | $p(x_2 \| y_2)$ | $p(x_2 \| y_3)$ |
| $x_3$ | $p(x_3 \| y_1)$ | $p(x_3 \| y_2)$ | $p(x_3 \| y_3)$ |

FIG. 1

| P(X,Y) | $y_1$ | $y_2$ | $y_3$ |
|---|---|---|---|
| $x_1$ | $p(x_1, y_1)$ | $p(x_1, y_2)$ | $p(x_1, y_3)$ |
| $x_2$ | $p(x_2, y_1)$ | $p(x_2, y_2)$ | $p(x_2, y_3)$ |
| $x_3$ | $p(x_3, y_1)$ | $p(x_3, y_2)$ | $p(x_3, y_3)$ |

FIG. 2

| Category | Node | States |
|---|---|---|
| Diagnosis | Breast Cancer | present, absent |
| Demographic Factors | Age (years)<br>Age at Menarche (years)<br>Age at First Life Birth (years)<br>Number of First-Degree Relatives with Breast Cancer<br>Previous Biopsy | 20-24, 25-29, ..., 75-79<br><12, 12-13, >=14<br><20, 20-24, 25-29, >=30<br><br>0, 1, >= 2<br><br><br>present, absent |
| Physical Findings | Pain<br>Nipple Discharge<br>Palpable Mass | present, absent<br>present, absent<br>present, absent |
| Indirect Mammographic Findings | Architectural Distortion<br>Asymmetry<br>Developing Density<br>Dilated Duct | present, absent<br>present, absent<br>present, absent<br>present, absent |
| Direct Mammographic Findings | Mass<br>  Mass Margin<br><br>  Mass Density<br>  Mass Size<br>  Halo Sign<br>  Tumor Location<br><br><br><br>Calcification<br>  Calcification Cluster Shape<br>  Number of Calcifications in Cluster<br>  Calcification Shape<br><br>  Calcification Density<br>  Calcification Arrangement<br>  Calcification Size (mm) | malignant, benign, none<br>spiculated, irregular, relatively well-defined, NA<br>high, low, NA<br>inSitu, <=5, 6-10, 11-20, >20, multiFocal, NA<br>present, absent, NA<br>upper outer (UO), upper inner (UI), lower outer (LO), lower inner (LI), retroareolar (RA), not available (NA)<br><br>malignant, benign, none<br>punctate, round, linear, variable, NA<br><br><=5, 6-10, 11-15, 16-25, 26-50, >50, NA<br><br>linear branching, irregular, indeterminate, round, NA<br>1-2, 1-3, 2-3, 3-4, NA<br>scattered, clustered, scattered & clustered, single, NA<br>0.05-0.1, 0.05-2, 0.01-1, 0.01-2, 1-3, NA |

FIG. 4

| P(BREAST CANCER) | | AGE | MENARCHE AGE | 1ST BIRTH AGE | # OF RELATIVES |
|---|---|---|---|---|---|
| PRESENT | ABSENT | | | | |
| 0.00005100 | 0.99994900 | 20-24 | >=14 | <20 | 0 |
| 0.00013296 | 0.99986704 | | | | 1 |
| 0.00034670 | 0.99965330 | | | | 2 |
| 0.00006344 | 0.99993656 | | | 20-24 | 0 |
| 0.00013673 | 0.99986327 | | | | 1 |
| 0.00029452 | 0.99970548 | | | | 2 |
| 0.00007895 | 0.99992105 | | | 25-29 | 0 |
| 0.00014055 | 0.99985945 | | | | 1 |
| 0.00025025 | 0.99974975 | | | | 2 |
| 0.00009828 | 0.99990172 | | | >=30 | 0 |
| 0.00014453 | 0.99985547 | | | | 1 |
| 0.00021262 | 0.99978738 | | | | 2 |
| 0.00005605 | 0.99994395 | | 12-13 | <20 | 0 |
| 0.00014612 | 0.99985388 | | | | 1 |
| 0.00038102 | 0.99961898 | | | | 2 |
| 0.00006972 | 0.99993028 | | | 20-24 | 0 |
| 0.00015027 | 0.99984973 | | | | 1 |
| 0.00032368 | 0.99967632 | | | | 2 |
| 0.00008676 | 0.99991324 | | | 25-29 | 0 |
| 0.00015447 | 0.99984553 | | | | 1 |
| 0.00027503 | 0.99972497 | | | | 2 |
| 0.00010801 | 0.99989199 | | | >=30 | 0 |
| 0.00015884 | 0.99984116 | | | | 1 |
| 0.00023367 | 0.99976633 | | | | 2 |
| 0.00006156 | 0.99993844 | | <12 | <20 | 0 |
| 0.00016048 | 0.99983952 | | | | 1 |
| 0.00041846 | 0.99958154 | | | | 2 |
| 0.00007658 | 0.99992342 | | | 20-24 | 0 |
| 0.00016503 | 0.99983497 | | | | 1 |
| 0.00035549 | 0.99964451 | | | | 2 |
| 0.00009529 | 0.99990471 | | | 25-29 | 0 |
| 0.00016965 | 0.99983035 | | | | 1 |
| 0.00030206 | 0.99969794 | | | | 2 |
| 0.00011862 | 0.99988138 | | | >=30 | 0 |
| 0.00017445 | 0.99982555 | | | | 1 |
| 0.00025663 | 0.99974337 | | | | 2 |
| 0.00039604 | 0.99960396 | 25-29 | >=14 | <20 | 0 |
| 0.00103248 | 0.99896752 | | | | 1 |
| 0.00269228 | 0.99730772 | | | | 2 |
| 0.00049267 | 0.99950733 | | | 20-24 | 0 |
| 0.00106178 | 0.99893822 | | | | 1 |
| 0.00228713 | 0.99771287 | | | | 2 |

FIG. 5A

| | | | | | |
|---|---|---|---|---|---|
| 0.00061307 | 0.99938693 | | | 25-29 | 0 |
| 0.00109149 | 0.99890851 | | | | 1 |
| 0.00194337 | 0.99805663 | | | | 2 |
| 0.00076317 | 0.99923683 | | | >=30 | 0 |
| 0.00112238 | 0.99887762 | | | | 1 |
| 0.00165109 | 0.99834891 | | | | 2 |
| 0.00043525 | 0.99956475 | | 12-13 | <20 | 0 |
| 0.00113469 | 0.99886531 | | | | 1 |
| 0.00295881 | 0.99704119 | | | | 2 |
| 0.00054145 | 0.99945855 | | | 20-24 | 0 |
| 0.00116690 | 0.99883310 | | | | 1 |
| 0.00251355 | 0.99748645 | | | | 2 |
| 0.00067376 | 0.99932624 | | | 25-29 | 0 |
| 0.00119954 | 0.99880046 | | | | 1 |
| 0.00213576 | 0.99786424 | | | | 2 |
| 0.00083872 | 0.99916128 | | | >=30 | 0 |
| 0.00123349 | 0.99876651 | | | | 1 |
| 0.00181455 | 0.99818545 | | | | 2 |
| 0.00047802 | 0.99952198 | | <12 | <20 | 0 |
| 0.00124620 | 0.99875380 | | | | 1 |
| 0.00324958 | 0.99675042 | | | | 2 |
| 0.00059466 | 0.99940534 | | | 20-24 | 0 |
| 0.00128157 | 0.99871843 | | | | 1 |
| 0.00276056 | 0.99723944 | | | | 2 |
| 0.00073997 | 0.99926003 | | | 25-29 | 0 |
| 0.00131742 | 0.99868258 | | | | 1 |
| 0.00234564 | 0.99765436 | | | | 2 |
| 0.00092114 | 0.99907886 | | | >=30 | 0 |
| 0.00135471 | 0.99864529 | | | | 1 |
| 0.00199286 | 0.99800714 | | | | 2 |
| 0.00160772 | 0.99839228 | 30-34 | >=14 | <20 | 0 |
| 0.00419132 | 0.99580868 | | | | 1 |
| 0.01092926 | 0.98907074 | | | | 2 |
| 0.00200000 | 0.99800000 | | | 20-24 | 0 |
| 0.00431029 | 0.99568971 | | | | 1 |
| 0.00928457 | 0.99071543 | | | | 2 |
| 0.00248875 | 0.99751125 | | | 25-29 | 0 |
| 0.00443087 | 0.99556913 | | | | 1 |
| 0.00788907 | 0.99211093 | | | | 2 |
| 0.00309807 | 0.99690193 | | | >=30 | 0 |
| 0.00455627 | 0.99544373 | | | | 1 |
| 0.00670257 | 0.99329743 | | | | 2 |
| 0.00176688 | 0.99823312 | | 12-13 | <20 | 0 |
| 0.00460626 | 0.99539374 | | | | 1 |
| 0.01201126 | 0.98798874 | | | | 2 |
| 0.00219800 | 0.99780200 | | | 20-24 | 0 |
| 0.00473701 | 0.99526299 | | | | 1 |

FIG. 5B

| | | | | | |
|---|---|---|---|---|---|
| 0.01020374 | 0.98979626 | | | | 2 |
| 0.00273513 | 0.99726487 | | | 25-29 | 0 |
| 0.00486952 | 0.99513048 | | | | 1 |
| 0.00867009 | 0.99132991 | | | | 2 |
| 0.00340478 | 0.99659522 | | | >=30 | 0 |
| 0.00500734 | 0.99499266 | | | | 1 |
| 0.00736613 | 0.99263387 | | | | 2 |
| 0.00194051 | 0.99805949 | | <12 | <20 | 0 |
| 0.00505892 | 0.99494108 | | | | 1 |
| 0.01319162 | 0.98680838 | | | | 2 |
| 0.00241400 | 0.99758600 | | | 20-24 | 0 |
| 0.00520252 | 0.99479748 | | | | 1 |
| 0.01120647 | 0.98879353 | | | | 2 |
| 0.00300392 | 0.99699608 | | | 25-29 | 0 |
| 0.00534806 | 0.99465194 | | | | 1 |
| 0.00952210 | 0.99047790 | | | | 2 |
| 0.00373937 | 0.99626063 | | | >=30 | 0 |
| 0.00549942 | 0.99450058 | | | | 1 |
| 0.00809000 | 0.99191000 | | | | 2 |
| 0.00460829 | 0.99539171 | 35-39 | >=14 | <20 | 0 |
| 0.01201382 | 0.98798618 | | | | 1 |
| 0.03132719 | 0.96867281 | | | | 2 |
| 0.00573272 | 0.99426728 | | | 20-24 | 0 |
| 0.01235484 | 0.98764516 | | | | 1 |
| 0.02661290 | 0.97338710 | | | | 2 |
| 0.00713364 | 0.99286636 | | | 25-29 | 0 |
| 0.01270046 | 0.98729954 | | | | 1 |
| 0.02261290 | 0.97738710 | | | | 2 |
| 0.00888018 | 0.99111982 | | | >=30 | 0 |
| 0.01305991 | 0.98694009 | | | | 1 |
| 0.01921198 | 0.98078802 | | | | 2 |
| 0.00506452 | 0.99493548 | | 12-13 | <20 | 0 |
| 0.01320319 | 0.98679681 | | | | 1 |
| 0.03442858 | 0.96557142 | | | | 2 |
| 0.00630026 | 0.99369974 | | | 20-24 | 0 |
| 0.01357797 | 0.98642203 | | | | 1 |
| 0.02924758 | 0.97075242 | | | | 2 |
| 0.00783987 | 0.99216013 | | | 25-29 | 0 |
| 0.01395781 | 0.98604219 | | | | 1 |
| 0.02485158 | 0.97514842 | | | | 2 |
| 0.00975932 | 0.99024068 | | | >=30 | 0 |
| 0.01435284 | 0.98564716 | | | | 1 |
| 0.02111397 | 0.97888603 | | | | 2 |
| 0.00556221 | 0.99443779 | | <12 | <20 | 0 |
| 0.01450069 | 0.98549931 | | | | 1 |
| 0.03781192 | 0.96218808 | | | | 2 |
| 0.00691939 | 0.99308061 | | | 20-24 | 0 |

FIG. 5C

| | | | | | |
|---|---|---|---|---|---|
| 0.01491229 | 0.98508771 | | | | 1 |
| 0.03212177 | 0.96787823 | | | | 2 |
| 0.00861030 | 0.99138970 | | | 25-29 | 0 |
| 0.01532946 | 0.98467054 | | | | 1 |
| 0.02729377 | 0.97270623 | | | | 2 |
| 0.01071838 | 0.98928162 | | | >=30 | 0 |
| 0.01576331 | 0.98423669 | | | | 1 |
| 0.02318886 | 0.97681114 | | | | 2 |
| 0.01075269 | 0.98924731 | 40-44 | >=14 | <20 | 0 |
| 0.02803226 | 0.97196774 | | | | 1 |
| 0.07309677 | 0.92690323 | | | | 2 |
| 0.01337634 | 0.98662366 | | | 20-24 | 0 |
| 0.02882796 | 0.97117204 | | | | 1 |
| 0.06209677 | 0.93790323 | | | | 2 |
| 0.01664516 | 0.98335484 | | | 25-29 | 0 |
| 0.02963441 | 0.97036559 | | | | 1 |
| 0.05276344 | 0.94723656 | | | | 2 |
| 0.02072043 | 0.97927957 | | | >=30 | 0 |
| 0.03047312 | 0.96952688 | | | | 1 |
| 0.04482796 | 0.95517204 | | | | 2 |
| 0.01181720 | 0.98818280 | | 12-13 | <20 | 0 |
| 0.03080745 | 0.96919255 | | | | 1 |
| 0.08033335 | 0.91966665 | | | | 2 |
| 0.01470060 | 0.98529940 | | | 20-24 | 0 |
| 0.03168192 | 0.96831808 | | | | 1 |
| 0.06824435 | 0.93175565 | | | | 2 |
| 0.01829303 | 0.98170697 | | | 25-29 | 0 |
| 0.03256822 | 0.96743178 | | | | 1 |
| 0.05798702 | 0.94201298 | | | | 2 |
| 0.02277175 | 0.97722825 | | | >=30 | 0 |
| 0.03348996 | 0.96651004 | | | | 1 |
| 0.04926592 | 0.95073408 | | | | 2 |
| 0.01297849 | 0.98702151 | | <12 | <20 | 0 |
| 0.03383494 | 0.96616506 | | | | 1 |
| 0.08822781 | 0.91177219 | | | | 2 |
| 0.01614525 | 0.98385475 | | | 20-24 | 0 |
| 0.03479534 | 0.96520466 | | | | 1 |
| 0.07495081 | 0.92504919 | | | | 2 |
| 0.02009071 | 0.97990929 | | | 25-29 | 0 |
| 0.03576873 | 0.96423127 | | | | 1 |
| 0.06368547 | 0.93631453 | | | | 2 |
| 0.02500956 | 0.97499044 | | | >=30 | 0 |
| 0.03678105 | 0.96321895 | | | | 1 |
| 0.05410734 | 0.94589266 | | | | 2 |
| 0.02000000 | 0.98000000 | 45-49 | >=14 | <20 | 0 |
| 0.05214000 | 0.94786000 | | | | 1 |
| 0.13596000 | 0.86404000 | | | | 2 |

FIG. 5D

| | | | | | |
|---|---|---|---|---|---|
| 0.02488000 | 0.97512000 | | | 20-24 | 0 |
| 0.05362000 | 0.94638000 | | | | 1 |
| 0.11550000 | 0.88450000 | | | | 2 |
| 0.03096000 | 0.96904000 | | | 25-29 | 0 |
| 0.05512000 | 0.94488000 | | | | 1 |
| 0.09814000 | 0.90186000 | | | | 2 |
| 0.03854000 | 0.96146000 | | | >=30 | 0 |
| 0.05668000 | 0.94332000 | | | | 1 |
| 0.08338000 | 0.91662000 | | | | 2 |
| 0.02198000 | 0.97802000 | | 12-13 | <20 | 0 |
| 0.05730186 | 0.94269814 | | | | 1 |
| 0.14942004 | 0.85057996 | | | | 2 |
| 0.02734312 | 0.97265688 | | | 20-24 | 0 |
| 0.05892838 | 0.94107162 | | | | 1 |
| 0.12693450 | 0.87306550 | | | | 2 |
| 0.03402504 | 0.96597496 | | | 25-29 | 0 |
| 0.06057688 | 0.93942312 | | | | 1 |
| 0.10785586 | 0.89214414 | | | | 2 |
| 0.04235546 | 0.95764454 | | | >=30 | 0 |
| 0.06229132 | 0.93770868 | | | | 1 |
| 0.09163462 | 0.90836538 | | | | 2 |
| 0.02414000 | 0.97586000 | | <12 | <20 | 0 |
| 0.06293298 | 0.93706702 | | | | 1 |
| 0.16410372 | 0.83589628 | | | | 2 |
| 0.03003016 | 0.96996984 | | | 20-24 | 0 |
| 0.06471934 | 0.93528066 | | | | 1 |
| 0.13940850 | 0.86059150 | | | | 2 |
| 0.03736872 | 0.96263128 | | | 25-29 | 0 |
| 0.06652984 | 0.93347016 | | | | 1 |
| 0.11845498 | 0.88154502 | | | | 2 |
| 0.04651778 | 0.95348222 | | | >=30 | 0 |
| 0.06841276 | 0.93158724 | | | | 1 |
| 0.10063966 | 0.89936034 | | | | 3 |
| 0.03030303 | 0.96969697 | 50-54 | >=14 | <20 | 0 |
| 0.07900000 | 0.92100000 | | | | 1 |
| 0.20600000 | 0.79400000 | | | | 2 |
| 0.03769697 | 0.96230303 | | | 20-24 | 0 |
| 0.08124242 | 0.91875758 | | | | 1 |
| 0.17500000 | 0.82500000 | | | | 2 |
| 0.04690909 | 0.95309091 | | | 25-29 | 0 |
| 0.08351515 | 0.91648485 | | | | 1 |
| 0.14869697 | 0.85130303 | | | | 2 |
| 0.05839394 | 0.94160606 | | | >=30 | 0 |
| 0.08587879 | 0.91412121 | | | | 1 |
| 0.12633333 | 0.87366667 | | | | 2 |
| 0.03330303 | 0.96669697 | | 12-13 | <20 | 0 |
| 0.08682100 | 0.91317900 | | | | 1 |

FIG. 5E

| | | | | | |
|---|---|---|---|---|---|
| 0.22639400 | 0.77360600 | | | | 2 |
| 0.04142897 | 0.95857103 | | | 20-24 | 0 |
| 0.08928542 | 0.91071458 | | | | 1 |
| 0.19232500 | 0.80767500 | | | | 2 |
| 0.05155309 | 0.94844691 | | | 25-29 | 0 |
| 0.09178315 | 0.90821685 | | | | 1 |
| 0.16341797 | 0.83658203 | | | | 2 |
| 0.06417494 | 0.93582506 | | | >=30 | 0 |
| 0.09438079 | 0.90561921 | | | | 1 |
| 0.13884033 | 0.86115967 | | | | 2 |
| 0.03657576 | 0.96342424 | | <12 | <20 | 0 |
| 0.09535300 | 0.90464700 | | | | 1 |
| 0.24864200 | 0.75135800 | | | | 2 |
| 0.04550024 | 0.95449976 | | | 20-24 | 0 |
| 0.09805961 | 0.90194039 | | | | 1 |
| 0.21122500 | 0.78877500 | | | | 2 |
| 0.05661927 | 0.94338073 | | | 25-29 | 0 |
| 0.10080279 | 0.89919721 | | | | 1 |
| 0.17947724 | 0.82052276 | | | | 2 |
| 0.070481 | 0.929519 | | | >=30 | 0 |
| 0.103655 | 0.896345 | | | | 1 |
| 0.15248433 | 0.84751567 | | | | 2 |
| 0.04166667 | 0.95833333 | 55-59 | >=14 | <20 | 0 |
| 0.10862500 | 0.89137500 | | | | 1 |
| 0.28325000 | 0.71675000 | | | | 2 |
| 0.05183333 | 0.94816667 | | | 20-24 | 0 |
| 0.11170833 | 0.88829167 | | | | 1 |
| 0.24062500 | 0.75937500 | | | | 2 |
| 0.06450000 | 0.93550000 | | | 25-29 | 0 |
| 0.11483333 | 0.88516667 | | | | 1 |
| 0.20445833 | 0.79554167 | | | | 2 |
| 0.08029167 | 0.91970833 | | | >=30 | 0 |
| 0.11808333 | 0.88191667 | | | | 1 |
| 0.17370833 | 0.82629167 | | | | 2 |
| 0.04579167 | 0.95420833 | | 12-13 | <20 | 0 |
| 0.11937887 | 0.88062113 | | | | 1 |
| 0.31129175 | 0.68870825 | | | | 2 |
| 0.05696483 | 0.94303517 | | | 20-24 | 0 |
| 0.12276746 | 0.87723254 | | | | 1 |
| 0.26444687 | 0.73555313 | | | | 2 |
| 0.07088550 | 0.92911450 | | | 25-29 | 0 |
| 0.12620183 | 0.87379817 | | | | 1 |
| 0.22469971 | 0.77530029 | | | | 2 |
| 0.08824054 | 0.91175946 | | | >=30 | 0 |
| 0.12977358 | 0.87022642 | | | | 1 |
| 0.19090546 | 0.80909454 | | | | 2 |
| 0.05029167 | 0.94970833 | | <12 | <20 | 0 |

FIG. 5F

| | | | | | |
|---|---|---|---|---|---|
| 0.13111038 | 0.86888962 | | | | 1 |
| 0.34188275 | 0.65811725 | | | | 2 |
| 0.06256283 | 0.93743717 | | | 20-24 | 0 |
| 0.13483196 | 0.86516804 | | | | 1 |
| 0.29043438 | 0.70956562 | | | | 2 |
| 0.07785150 | 0.92214850 | | | 25-29 | 0 |
| 0.13860383 | 0.86139617 | | | | 1 |
| 0.24678121 | 0.75321879 | | | | 2 |
| 0.09691204 | 0.90308796 | | | >=30 | 0 |
| 0.14252658 | 0.85747342 | | | | 1 |
| 0.20966596 | 0.79033404 | | | | 2 |
| 0.05882353 | 0.94117647 | 60-64 | >=14 | <20 | 0 |
| 0.15335294 | 0.84664706 | | | | 1 |
| 0.39988235 | 0.60011765 | | | | 2 |
| 0.07317647 | 0.92682353 | | | 20-24 | 0 |
| 0.15770588 | 0.84229412 | | | | 1 |
| 0.33970588 | 0.66029412 | | | | 2 |
| 0.09105882 | 0.90894118 | | | 25-29 | 0 |
| 0.16211765 | 0.83788235 | | | | 1 |
| 0.28864706 | 0.71135294 | | | | 2 |
| 0.11335294 | 0.88664706 | | | >=30 | 0 |
| 0.16670588 | 0.83329412 | | | | 1 |
| 0.24523529 | 0.75476471 | | | | 2 |
| 0.06464706 | 0.93535294 | | 12-13 | <20 | 0 |
| 0.16853488 | 0.83146512 | | | | 1 |
| 0.43947071 | 0.56052929 | | | | 2 |
| 0.08042094 | 0.91957906 | | | 20-24 | 0 |
| 0.17331876 | 0.82668124 | | | | 1 |
| 0.37333676 | 0.62666324 | | | | 2 |
| 0.10007365 | 0.89992635 | | | 25-29 | 0 |
| 0.17816729 | 0.82183271 | | | | 1 |
| 0.31722312 | 0.68277688 | | | | 2 |
| 0.12457488 | 0.87542512 | | | >=30 | 0 |
| 0.18320976 | 0.81679024 | | | | 1 |
| 0.26951359 | 0.73048641 | | | | 2 |
| 0.07100000 | 0.92900000 | | <12 | <20 | 0 |
| 0.18509700 | 0.81490300 | | | | 1 |
| 0.48265800 | 0.51734200 | | | | 2 |
| 0.08832400 | 0.91167600 | | | 20-24 | 0 |
| 0.19035100 | 0.80964900 | | | | 1 |
| 0.41002500 | 0.58997500 | | | | 2 |
| 0.10990800 | 0.89009200 | | | 25-29 | 0 |
| 0.19567600 | 0.80432400 | | | | 1 |
| 0.34839700 | 0.65160300 | | | | 2 |
| 0.13681700 | 0.86318300 | | | >=30 | 0 |
| 0.20121400 | 0.79878600 | | | | 1 |
| 0.29599900 | 0.70400100 | | | | 2 |

FIG. 5G

| | | | | | |
|---|---|---|---|---|---|
| 0.07142857 | 0.92857143 | 65-69 | >=14 | <20 | 0 |
| 0.18621429 | 0.81378571 | | | | 1 |
| 0.48557143 | 0.51442857 | | | | 2 |
| 0.08885714 | 0.91114286 | | | 20-24 | 0 |
| 0.19150000 | 0.80850000 | | | | 1 |
| 0.41250000 | 0.58750000 | | | | 2 |
| 0.11057143 | 0.88942857 | | | 25-29 | 0 |
| 0.19685714 | 0.80314286 | | | | 1 |
| 0.35050000 | 0.64950000 | | | | 2 |
| 0.13764286 | 0.86235714 | | | >=30 | 0 |
| 0.20242857 | 0.79757143 | | | | 1 |
| 0.29778571 | 0.70221429 | | | | 2 |
| 0.07850000 | 0.92150000 | | 12-13 | <20 | 0 |
| 0.20464950 | 0.79535050 | | | | 1 |
| 0.53364300 | 0.46635700 | | | | 2 |
| 0.09765400 | 0.90234600 | | | 20-24 | 0 |
| 0.21045850 | 0.78954150 | | | | 1 |
| 0.45333750 | 0.54666250 | | | | 2 |
| 0.12151800 | 0.87848200 | | | 25-29 | 0 |
| 0.21634600 | 0.78365400 | | | | 1 |
| 0.38519950 | 0.61480050 | | | | 2 |
| 0.15126950 | 0.84873050 | | | >=30 | 0 |
| 0.22246900 | 0.77753100 | | | | 1 |
| 0.32726650 | 0.67273350 | | | | 2 |
| 0.08621429 | 0.91378571 | | <12 | <20 | 0 |
| 0.22476064 | 0.77523936 | | | | 1 |
| 0.58608471 | 0.41391529 | | | | 2 |
| 0.10725057 | 0.89274943 | | | 20-24 | 0 |
| 0.23114050 | 0.76885950 | | | | 1 |
| 0.49788750 | 0.50211250 | | | | 2 |
| 0.13345971 | 0.86654029 | | | 25-29 | 0 |
| 0.23760657 | 0.76239343 | | | | 1 |
| 0.42305350 | 0.57694650 | | | | 2 |
| 0.16613493 | 0.83386507 | | | >=30 | 0 |
| 0.24433129 | 0.75566871 | | | | 1 |
| 0.35942736 | 0.64057264 | | | | 2 |
| 0.09090909 | 0.90909091 | 70-74 | >=14 | <20 | 0 |
| 0.23700000 | 0.76300000 | | | | 1 |
| 0.61800000 | 0.38200000 | | | | 2 |
| 0.11309091 | 0.88690909 | | | 20-24 | 0 |
| 0.24372727 | 0.75627273 | | | | 1 |
| 0.52500000 | 0.47500000 | | | | 2 |
| 0.14072727 | 0.85927273 | | | 25-29 | 0 |
| 0.25054545 | 0.74945455 | | | | 1 |
| 0.44609091 | 0.55390909 | | | | 2 |
| 0.17518182 | 0.82481818 | | | >=30 | 0 |
| 0.25763636 | 0.74236364 | | | | 1 |

FIG. 5H

| | | | | | |
|---|---|---|---|---|---|
| 0.37900000 | 0.62100000 | | | | 2 |
| 0.09990909 | 0.90009091 | | 12-13 | <20 | 0 |
| 0.26046300 | 0.73953700 | | | | 1 |
| 0.67918200 | 0.32081800 | | | | 2 |
| 0.12428691 | 0.87571309 | | | 20-24 | 0 |
| 0.26785627 | 0.73214373 | | | | 1 |
| 0.57697500 | 0.42302500 | | | | 2 |
| 0.15465927 | 0.84534073 | | | 25-29 | 0 |
| 0.27534945 | 0.72465055 | | | | 1 |
| 0.49025391 | 0.50974609 | | | | 2 |
| 0.19252482 | 0.80747518 | | | >=30 | 0 |
| 0.28314236 | 0.71685764 | | | | 1 |
| 0.41652100 | 0.58347900 | | | | 2 |
| 0.10972727 | 0.89027273 | | <12 | <20 | 0 |
| 0.28605900 | 0.71394100 | | | | 1 |
| 0.74592600 | 0.25407400 | | | | 2 |
| 0.13650073 | 0.86349927 | | | 20-24 | 0 |
| 0.29417882 | 0.70582118 | | | | 1 |
| 0.63367500 | 0.36632500 | | | | 2 |
| 0.16985782 | 0.83014218 | | | 25-29 | 0 |
| 0.30240836 | 0.69759164 | | | | 1 |
| 0.53843173 | 0.46156827 | | | | 2 |
| 0.21144445 | 0.78855555 | | | >=30 | 0 |
| 0.31096709 | 0.68903291 | | | | 1 |
| 0.45745300 | 0.54254700 | | | | 2 |
| 0.10000000 | 0.90000000 | 75-79 | >=14 | <20 | 0 |
| 0.26070000 | 0.73930000 | | | | 1 |
| 0.67980000 | 0.32020000 | | | | 2 |
| 0.12440000 | 0.87560000 | | | 20-24 | 0 |
| 0.26810000 | 0.73190000 | | | | 1 |
| 0.57750000 | 0.42250000 | | | | 2 |
| 0.15480000 | 0.84520000 | | | 25-29 | 0 |
| 0.27560000 | 0.72440000 | | | | 1 |
| 0.49070000 | 0.50930000 | | | | 2 |
| 0.19270000 | 0.80730000 | | | >=30 | 0 |
| 0.28340000 | 0.71660000 | | | | 1 |
| 0.41690000 | 0.58310000 | | | | 2 |
| 0.10990000 | 0.89010000 | | 12-13 | <20 | 0 |
| 0.28650930 | 0.71349070 | | | | 1 |
| 0.74710020 | 0.25289980 | | | | 2 |
| 0.13671560 | 0.86328440 | | | 20-24 | 0 |
| 0.29464190 | 0.70535810 | | | | 1 |
| 0.63467250 | 0.36532750 | | | | 2 |
| 0.17012520 | 0.82987480 | | | 25-29 | 0 |
| 0.30288440 | 0.69711560 | | | | 1 |
| 0.53927930 | 0.46072070 | | | | 2 |
| 0.21177730 | 0.78822270 | | | >=30 | 0 |

FIG. 5I

| | | | | | |
|---|---|---|---|---|---|
| 0.31145660 | 0.68854340 | | | | 1 |
| 0.45817310 | 0.54182690 | | | | 2 |
| 0.12070000 | 0.87930000 | | <12 | <20 | 0 |
| 0.31466490 | 0.68533510 | | | | 1 |
| 0.82051860 | 0.17948140 | | | | 2 |
| 0.15015080 | 0.84984920 | | | 20-24 | 0 |
| 0.32359670 | 0.67640330 | | | | 1 |
| 0.69704250 | 0.30295750 | | | | 2 |
| 0.18684360 | 0.81315640 | | | 25-29 | 0 |
| 0.33264920 | 0.66735080 | | | | 1 |
| 0.59227490 | 0.40772510 | | | | 2 |
| 0.23258890 | 0.76741110 | | | >=30 | 0 |
| 0.34206380 | 0.65793620 | | | | 1 |
| 0.50319830 | 0.49680170 | | | | 2 |

FIG. 5J

| P(AGE) | AGE-RANGE IN YEARS |
|---|---|
| 0.1025 | 20-24 |
| 0.1107 | 25-29 |
| 0.1235 | 30-34 |
| 0.1185 | 35-39 |
| 0.1067 | 40-44 |
| 0.0874 | 45-49 |
| 0.0706 | 50-54 |
| 0.0616 | 55-59 |
| 0.0610 | 60-64 |
| 0.0612 | 65-69 |
| 0.0536 | 70-74 |
| 0.0427 | 75-79 |

FIG. 6

| P(AGE OF MENARCHE) | AGE-RANGE IN YEARS |
|---|---|
| 0.350 | >=14 |
| 0.514 | 12-13 |
| 0.136 | <12 |

FIG. 7

| P(AGE OF FIRST BIRTH) | AGE RANGE IN YEARS |
|---|---|
| 0.2595 | <20 |
| 0.374 | 20-24 |
| 0.255 | 25-29 |
| 0.1115 | >=30 |

FIG. 8

| P(NUMBER OF RELATIVES) | NUMBER OF RELATIVES |
|---|---|
| 0.6 | 0 |
| 0.3 | 1 |
| 0.1 | >=2 |

FIG. 9

| P(PREVIOUS BIOPSY) | STATE |
|---|---|
| 0.2 | PRESENT |
| 0.8 | ABSENT |

FIG. 10

| P(ARCHITECTURAL DISTORTION) | | BREAST CANCER STATE | PREVIOUS BIOPSY STATE |
|---|---|---|---|
| PRESENT | ABSENT | | |
| 99/100 | 1/100 | PRESENT | PRESENT |
| 26/300 | 274/300 | PRESENT | ABSENT |
| 99/100 | 1/100 | ABSENT | PRESENT |
| 1/1000 | 999/1000 | ABSENT | ABSENT |

FIG. 11

| P(ASYMMETRY) | | BREAST CANCER STATE |
|---|---|---|
| PRESENT | ABSENT | |
| 8/300 | 292/300 | PRESENT |
| 1/1000 | 999/1000 | ABSENT |

FIG. 12

| P(DEVELOPING DENSITY) | | BREAST CANCER STATE |
|---|---|---|
| PRESENT | ABSENT | |
| 19/300 | 281/300 | PRESENT |
| 1/1000 | 999/1000 | ABSENT |

FIG. 13

| P(DILATED DUCT) | | BREAST CANCER STATE |
|---|---|---|
| PRESENT | ABSENT | |
| 4/57 | 53/57 | PRESENT |
| 1/100 | 99/100 | ABSENT |

FIG. 14

| P(MASS) | | | BREAST CANCER STATE |
|---|---|---|---|
| MALIGNANT | BENIGN | NONE | |
| 0.40 | 0.0 | 0.60 | PRESENT |
| 0.0 | 0.1 | 0.9 | ABSENT |

FIG. 15

| P(CALCIFICATION) | | | BREAST CANCER STATE |
|---|---|---|---|
| MALIGNANT | BENIGN | NONE | |
| 0.20 | 0.0 | 0.80 | PRESENT |
| 0.0 | 0.1 | 0.9 | ABSENT |

FIG. 16

| P(TUMOR LOCATION) | | | | | | MASS STATE |
|---|---|---|---|---|---|---|
| UO | UI | LO | LI | RA | NA | |
| 0.52 | 0.143 | 0.143 | 0.05 | 0.144 | 0.00 | MALIGNANT |
| 0.54 | 0.14 | 0.10 | 0.07 | 0.15 | 0.00 | BENIGN |
| 0.00 | 0.0 | 0.00 | 0.00 | 0.00 | 1.00 | NONE |

FIG. 17

| P(MASS MARGIN) | | | | MASS STATE |
|---|---|---|---|---|
| SPICULATED | IRREGULAR | RWDEFINED | NA | |
| 49/118 | 57/118 | 12/118 | 0.0 | MALIGNANT |
| 1/1000 | 1/1000 | 998/100 | 0.0 | BENIGN |
| 0 | 0.0 | 0.0 | 1.0 | NONE |

FIG. 18

| P(MASS DENSITY) | | | MASS STATE |
|---|---|---|---|
| LOW DENSITY | HIGH DENSITY | NA | |
| 21/40 | 19/40 | 0.0 | MALIGNANT |
| 41/51 | 10/51 | 0.0 | BENIGN |
| 0.0 | 0.0 | 1.0 | NONE |

FIG. 19

| P(HALO SIGN) | | | MASS STATE |
|---|---|---|---|
| PRESENT | ABSENT | NA | |
| 25/1000 | 975/1000 | 0 | MALIGNANT |
| 0.3 | 0.7 | 0 | BENIGN |
| 0 | 0 | 1 | NONE |

FIG. 20

| P(MASS SIZE) | | | | | | | MASS STATE |
|---|---|---|---|---|---|---|---|
| INSITU | <=5 | 6-10 | 11-20 | >20 | MULTIFOCAL | NA | |
| 84/300 | 20/300 | 78/300 | 67/300 | 7/300 | 44/300 | 0 | MALIGNANT |
| 8/200 | 60/200 | 10/200 | 14/200 | 90/200 | 18/200 | 0 | BENIGN |
| 0 | 0 | 0 | 0 | 0 | 0 | 1 | NONE |

FIG. 21

| P(CALCIFICATION SHAPE) | | | | | CALCIFICATION STATE |
|---|---|---|---|---|---|
| LINEAR BRANCHING | IRREGULAR | INDETERMINATE | ROUND | NA | |
| 68/125 | 8/125 | 49/125 | 0.0 | 0.0 | MALIGNANT |
| 1/100 | 1/100 | 1/100 | 97/100 | 0.0 | BENIGN |
| 0.0 | 0.0 | 0.0 | 0.0 | 0.0 | NONE |

FIG. 22

| P(NUMBER IN CLUSTER) | | | | | | | CALCIFICATION STATE |
|---|---|---|---|---|---|---|---|
| <=5 | 6-10 | 11-15 | 16-25 | 26-50 | >50 | NA | |
| 0 | 0.16 | 0.14 | 0.20 | 0.32 | 0.18 | 0.0 | MALIGNANT |
| 0.04 | 0.42 | 0.30 | 0.10 | 0.02 | 0.12 | 0.0 | BENIGN |
| 0.0 | 0.0 | 0.0 | 0.0 | 0.0 | 0.0 | 1.0 | NONE |

FIG. 23

| P(CALCIFICATION CLUSTER SHAPE) | | | | | CALCIFICATION STATE |
|---|---|---|---|---|---|
| PUNCTATE | ROUND | LINEAR | VARIABLE | NA | |
| 0.36 | 0.08 | 0.02 | 0.54 | 0.0 | MALIGNANT |
| 0.64 | 0.14 | 0.04 | 0.18 | 0.0 | BENIGN |
| 0.0 | 0.0 | 0.0 | 0.0 | 1.0 | NONE |

FIG. 24

| P(CALCIFICATION DENSITY) | | | | | CALCIFICATION STATE |
|---|---|---|---|---|---|
| 1-2 | 1-3 | 2-3 | 3-4 | NA | |
| 0.18 | 0.76 | 0.04 | 0.02 | 0.0 | MALIGNANT |
| 0.12 | 0.48 | 0.26 | 0.14 | 0.0 | BENIGN |
| 0.0 | 0.0 | 0.0 | 0.0 | 1.0 | NONE |

FIG. 25

| P(CALCIFICATION SIZE) | | | | | | CALCIFICATION STATE |
|---|---|---|---|---|---|---|
| 0.05-0.1 | 0.05-2 | 0.01-1 | 0.01-2 | 1-3 | NA | |
| 0.29 | 0.33 | 0.28 | 0.10 | 0.00 | 0.0 | MALIGNANT |
| 0.12 | 0.10 | 0.75 | 0.06 | 0.02 | 0.0 | BENIGN |
| 0.0 | 0.0 | 0.0 | 0.0 | 0.0 | 1.0 | NONE |

FIG. 26

| P(CALCIFICATION ARRANGEMENT) | | | | | CALCIFICATION STATE |
|---|---|---|---|---|---|
| SCATTERED | CLUSTERED | SCATTERED & CLUSTERED | SINGLE | NA | |
| 78/281 | 109/281 | 66/281 | 30/281 | 0 | MALIGNANT |
| 203/514 | 130/514 | 139/514 | 42/514 | 0 | BENIGN |
| 0.0 | 0.0 | 0.0 | 0.0 | 1.0 | NONE |

FIG. 27

| P(PAIN) | | BREAST CANCER STATE |
|---|---|---|
| PRESENT | ABSENT | |
| 3/65 | 62/65 | PRESENT |
| 9/379 | 370/379 | ABSENT |

FIG. 28

| P(NIPPLE DISCHARGE) | | BREAST CANCER STATE |
|---|---|---|
| PRESENT | ABSENT | |
| 1/65 | 64/65 | PRESENT |
| 3/379 | 376/379 | ABSENT |

FIG. 29

| P(PALPABLE MASS) | | | MASS STATE |
|---|---|---|---|
| PRESENT | ABSENT | NA | |
| 0.62 | 0.38 | 0.0 | MALIGNANT |
| 0.43 | 0.57 | 0.0 | BENIGN |
| 0.0 | 0.0 | 1.0 | NONE |

FIG. 30

| FIELD POSITION | FIELD NAME | DEFAULT VALUE | RANGE OF VALUES | CORRESPONDING NODE NUMBER |
|---|---|---|---|---|
| 0 | AGE | 0 | 0-12 | 0 |
| 1 | AGE OF MENARCHE | 0 | 0-3 | 1 |
| 2 | AGE OF FIRST LIFE BIRTH | 0 | 0-4 | 2 |
| 3 | NUMBER OF RELATIVES | 0 | 0-3 | 3 |
| 4 | BREAST CANCER | | | 4 |
| 5 | MASS | | | 5 |
| 6 | CALCIFICATION | | | 6 |
| 7 | ASYMMETRY | 0 | 0-2 | 7 |
| 8 | DEVELOPING DENSITY | 0 | 0-2 | 8 |
| 9 | DILATED DUCT | 0 | 0-2 | 9 |
| 10 | PAIN | 0 | 0-2 | 10 |
| 11 | NIPPLE DISCHARGE | 0 | 0-2 | 11 |
| 12 | ARCHITECTURAL DISTORTION | 0 | 0-2 | 12 |
| 13 | PREVIOUS BIOPSY | 0 | 0-2 | 13 |
| 14 | TUMOR LOCATION | 0 | 0-6 | 14 |
| 15 | MASS MARGIN | 0 | 0-4 | 15 |
| 16 | MASS DENSITY | 0 | 0-3 | 16 |
| 17 | HALO SIGN | 0 | 0-3 | 17 |
| 18 | MASS SIZE | 0 | 0-7 | 18 |
| 19 | PALPABLE MASS | 0 | 0-2 | 19 |
| 20 | CALCIFICATION SHAPE | 0 | 0-5 | 20 |
| 21 | NUMBER OF CALCIFICATIONS IN CLUSTER | 0 | 0-7 | 21 |
| 22 | CALCIFICATION CLUSTER SHAPE | 0 | 0-5 | 22 |
| 23 | CALCIFICATION DENSITY | 0 | 0-5 | 23 |
| 24 | CALCIFICATION SIZE | 0 | 0-6 | 24 |
| 25 | CALCIFICATION ARRANGEMENT | 0 | 0-5 | 25 |

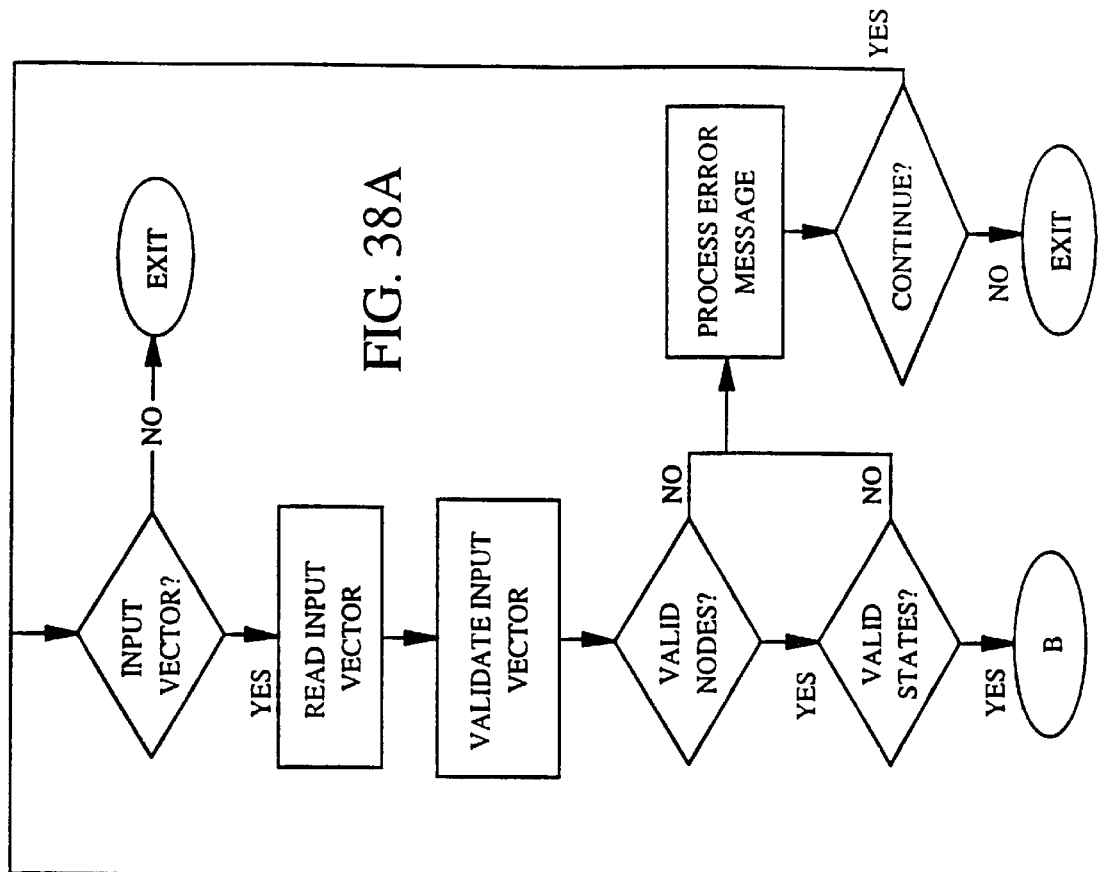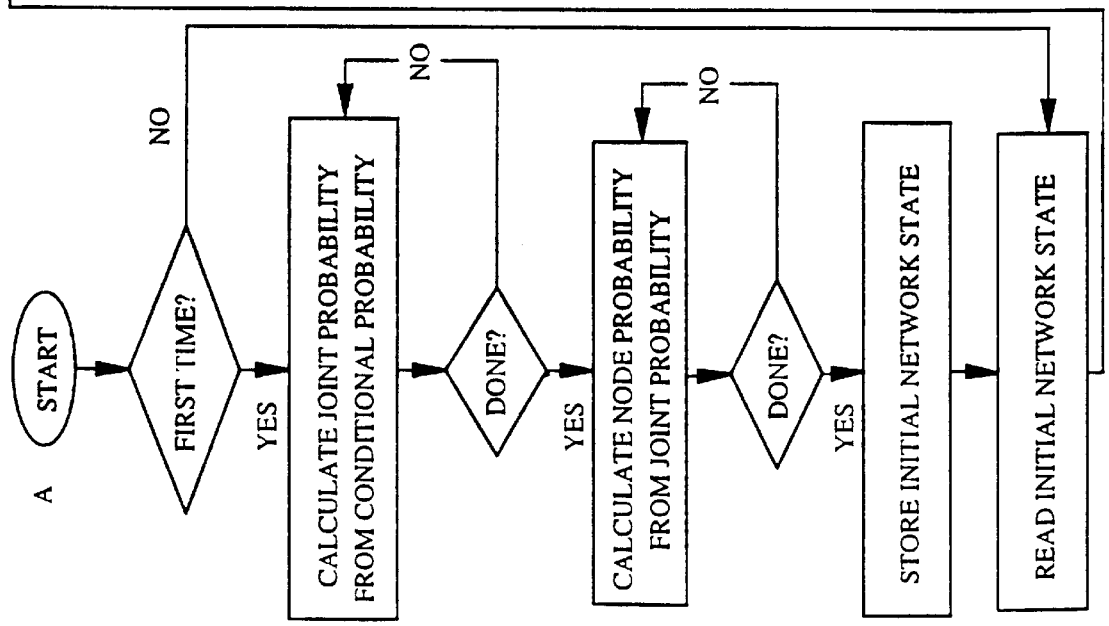
FIG. 38A

| Statement Type Token | Statement Type Description |
|---|---|
| INFORMATION_STATEMENT | System-created information statement for user |
| WELCOME_BANNER | System-created welcome banner |
| GENERAL_EXPLAIN_COMMAND | System identified a general request for an explanation |
| SPECIFIC_EXPLAIN_COMMAND | System identified a specific request for an explanation |
| GENERAL_CONCERN_QUERY | System identified a general request for concern |
| SPECIFIC_CONCERN_QUERY | System identified a specific request for concern |
| GENERAL_DEMO_COMMAND | System identified a general request for demonstration |
| SPECIFIC_DEMO_COMMAND | System identified a specific request for demonstration |
| YES_COMMAND | System identified an affirmation |
| NO_COMMAND | System identified |
| COMMAND_UNKNOWN | System was unable to determine user request |
| CONCEPT_NOUN_AGE_MENARCHE | System identified topic Age at Menarche |
| CONCEPT_NOUN_AGE_FIRST_LIVE_BIRTH | System identified topic Age at First Live Birth |
| CONCEPT_NOUN_NUM_RELATIVES_HX_CANCER | System identified topic Number of Relatives with Hx BCa |
| CONCEPT_NOUN_PREVIOUS_BIOPSY | System identified topic Previous Biopsy at Same Site |
| CONCEPT_NOUN_PAIN | System identified topic Breast Pain |
| CONCEPT_NOUN_NIPPLE_DISCHARGE | System identified topic Nipple Discharge |
| CONCEPT_NOUN_PALPABLE_MASS | System identified topic Palpable Mass |
| CONCEPT_NOUN_ARCHITECTURAL_DISTORTION | System identified topic Architectural distortion |
| CONCEPT_NOUN_ASYMMETRY | System identified topic Asymmetry |
| CONCEPT_NOUN_DEVELOPING_DENSITY | System identified topic Developing Density |
| CONCEPT_NOUN_DILATED_DUCT | System identified topic Dilated Duct |
| CONCEPT_NOUN_MASS_MARGIN | System identified topic Mass Margin |
| CONCEPT_NOUN_MASS_DENSITY | System identified topic Mass Density |
| CONETP_NOUN_MASS_SIZE | System identified topic Mass Size |
| CONCEPT_NOUN_HALO_SIGN | System identified topic Halo Sign |
| CONCEPT_NOUN_TUMOR_LOCATION | System identified topic Tumor Location |
| CONCEPT_NOUN_CALC_CLUSTER_SHAPE | System identified topic Calcification Cluster Shape |
| CONCEPT_NOUN_NUMBER_CALCS_IN_CLUSTER | System identified topic Number of Calcifications in Cluster |
| CONCETP_NOUN_CALCIFICATION_SHAPE | System identified topic Calcification Shape |
| CONCEPT_NOUN_CALCIFICATION_DENSITY | System identified topic Calcification Density |
| CONCEPT_NOUN_CALC_ARRANGEMENT | System identified topic Calcification Arrangement |
| CONCEPT_NOUN_CALCIFICATION_SIZE | System identified topic Calcification Size |

FIG. 40

| Modality Type | Modality Type Description |
| --- | --- |
| TYPED_KEYBOARD | User typed utterance at keyboard |
| RIGHT_MOUSE_CLICK | User single-clicked right mouse button |
| LEFT_MOUSE_CLICK | User single-clicked left mouse button |
| DOUBLE_CLICK | User double-clicked mouse button |
| DISPLAYED_GRAHPICS | System displayed graphics on screen |
| DISPLAYED_TEXT | System displayed text on screen |

FIG. 41

| Statement Context | Statement Context Description |
|---|---|
| INFORMATION_CONTEXT | System participants are engaged in information sharing |
| WELCOME_CONTEXT | System participants are engaged in welcome |
| GENERAL_EXPLAIN | System participants are engaged in general explanation processing |
| SPECIFIC_EXPLAIN | System participants are engaged in specific explanation processing |
| GENERAL_CONCERN | System participants are engaged in general concern processing |
| SPECIFIC_CONCERN | System participants are engaged in specific concern processing |
| GENERAL_DEMO | System participants are engaged in general demo processing |
| SPECIFIC_DEMO | System participants are engaged in specific demo processing |
| YES_CONTEXT | System participants are engaged in affirmative processing |
| NO_CONTEXT | System participants are engaged in negative processing |
| CONCEPT_UNKNOWN | System participants are engaged in ambiguity resolution |
| SPECIFIC_CONCERN_AGE_MENARCHE | System participants are engaged in age of menarche processing |
| SPECIFIC_CONCERN_AGE_FIRST_LIVE_BIRTH | System participants are engaged in age at first live birth processing |
| SPECIFIC_CONCERN_NUM_RELATIVES_HX_BCa | System participants are engaged in number of relatives with Hx Bca processing |
| SPECIFIC_CONCERN_PREV_BIOPSY | System participants are engaged in previous biopsy processing |
| SPECIFIC_CONCERN_PAIN | System participants are engaged in breast pain processing |
| SPECIFIC_CONCERN_NIPPLE_DISCHARGE | System participants are engaged in nipple discharge processing |
| SPECIFIC_CONCERN_PALPABLE_MASS | System participants are engaged in palpable mass processing |
| SPECIFIC_CONCERN_ARCHITECT_DISTORTION | System participants are engaged in architectural distortion processing |
| SPECIFIC_CONCERN_ASYMMETRY | System participants are engaged in asymmetry processing |
| SPECIFIC_CONCERN_DEVELOPING_DENSITY | System participants are engaged in developing density processing |
| SPECIFIC_CONCERN_DILATED_DUCT | System participants are engaged in dilated duct processing |
| SPECIFIC_CONCERN_MASS_MARGIN | System participants are engaged in mass margin processing |
| SPECIFIC_CONCERN_MASS_DENSITY | System participants are engaged in mass density processing |
| SPECIFIC_CONCERN_MASS_SIZE | System participants are engaged in mass size processing |
| SPECIFIC_CONCERN_HALO_SIGN | System participants are engaged in halo sign processing |
| SPECIFIC_CONCERN_TUMOR_LOCATION | System participants are engaged in tumor location processing |
| SPECIFIC_CONCERN_CALC_CLUSTER_SHAPE | System participants are engaged in calcification cluster shape processing |
| SPECIFIC_CONCERN _NUM_CALCS_IN_CLUSTER | System participants are engaged in number of calcification in cluster processing |
| SPECIFIC_CONCERN_CALCIFICATION_SHAPE | System participants are engaged in calcification shape processing |
| SPECIFIC_CONCERN_CALCIFICATION_DENSITY | System participants are engaged in calcification density processing |
| SPECIFIC_CONCERN_CALC_ARRANGEMENT | System participants are engaged in calcification arrangement |
| SPECIFIC_CONCERN_CALCIFICATION_SIZE | System participants are engaged in calcification size |

FIG. 42

| Semantic Type | Semantic Type Description |
|---|---|
| GENERAL_VERB | Action word such as explain, show, etc. |
| EXPLAIN_VERB | word or word phrases that express a desire to clarify, i.e., tell, explain, clarify |
| CONCERN_VERB | word or word phrases that express a concern, i.e., worry, concerned about. |
| DEMO_VERB | word or word phrases that express a desire to demonstrate or show, i.e. 'tell me', 'show me' |
| GENERAL_NOUN | Word or word phrase describing a person, place, or thing, such as 'breast cancer', 'age of menarche', 'in situ', 'patient', etc |
| RISK_FACTOR_NOUN | word or word phrase that describes a risk factor |
| PHYSICAL_HISTORY_NOUN | word or word phrase that describes a physical history item, 'breast pain' |
| MASS_NOUN | word or word phrase that describes a mammographic mass indication description, i.e., margin, size |
| CLACIFICATION_NOUN | word or word phrase that describes a mammographic calcification indication description |
| INDIRECT_NOUN | word or word phrase that describes a mammographic indirect indication description |
| ADJECTIVE | Descriptive word enhancing nouns such as faint, irregular, spiculated |
| RF_AGE_ADJECTIVE | word or word phrase that describes the risk factor age, i.e., young, middle-aged, 'years old' |
| RF_AGE_MENARCHE_ADJECTIVE | word or word phrases that describe the risk factor age of menarche, i.e., 'early menstruation', 'late onset' |
| RF_FAMILY_HISTORY_BREAST_CANCER | word or word phrases that describe the risk factor family history of breast cancer, 'strong family history', 'no family history' |
|  |  |
|  |  |
| ADVERB | Descriptive word enhancing verbs such as densely, |
| PRONOUN | I, you, me |
| HOW_QUESTION | Query word such as 'how' |
| WHAT_QUESTION | Query word such as 'what' |
| WHY_QUESTION | Query word such as 'why' |
| IF_QUESTION | Query word such as 'if' |
| AFFIRMATIVE | Affirmative word such as yes, alright, ok |
| NEGATIVE | Negation word such as no, not, never, none |
| DISJUNCTION | or |
| CONJUNCTION | and |

FIG. 43

EXPLANATION GENERATION SYSTEM FOR A DIAGNOSIS SUPPORT TOOL EMPLOYING AN INFERENCE SYSTEM

CROSS-REFERENCE TO RELATED APPLICATION

This application is a continuation-in-part of U.S. nonprovisional application Ser. No. 08/998,494, filed Dec. 26, 1997, now U.S. Pat. No. 6,056,690. The '494 application claims priority to provisional application Ser. No. 60/034,383 filed Dec. 27, 1996.

BACKGROUND OF THE INVENTION a. Field of the Invention

The instant invention is directed toward an explanation generation system for a computer-aided decision support tool employing an inference system. More specifically, it relates to a computer-aided diagnosis support tool employing an inference system and an interactive multimodal explanation generation system therefor. The explanation generation system produces interactive multimodal explanations for the results generated by the inference system in the diagnostic support tool.

b. Background Art

A woman has a 1 in 8 chance of developing breast cancer in her lifetime. In 1995, an estimated 183,400 women in the United States were newly diagnosed with breast cancer, and 46,240 died of the disease. Screening mammography effectively detects early breast cancers and can increase the likelihood of cure and long-term survival. Differentiating between benign and malignant mammographic findings, however, is difficult, with approximately 75% of mammograms classified "indeterminate."

Successful diagnosis depends on the ability of a physician to detect mammographic abnormalities and to integrate clinical information such as risk factors and physical findings to determine the likelihood of breast cancer. Only 15%–30% of biopsies performed on nonpalpable but mammographically suspicious lesions prove malignant. Unnecessary biopsies are costly in terms of physical and emotional discomfort to the patient. Subsequent radiographic abnormalities from biopsies can be mistaken for cancer. Thus, the cost of screening mammography is increased.

Computer technology in the form of a clinical decision-support tool can be employed to improve the diagnostic accuracy and cost-effectiveness of screening mammography. Automated classification of mammographic findings using discriminant analysis and artificial neural networks (ANNs) has already indicated the potential usefulness of computer-aided diagnosis. ANNs learn directly from observations with a knowledge base of impenetrable numerical connection values. Although they perform well, ANNs do not provide for meaningful explanation generation.

Bayesian networks—also called belief networks or causal probabilistic networks—use probability theory as an underpinning for reasoning under uncertainty. One could use Bayesian networks as the formalism to construct a decision support tool. This tool integrated with a clinical database would provide accurate, reliable, and consistent diagnoses. A Bayesian network could perform a differential diagnosis by specifying the observed symptoms and computing the posterior probability of the various diagnoses using standard probability formulas.

Bayesian Networks provide a number of powerful capabilities for representing uncertain knowledge. Their flexible representation allows one to specify dependence and independence of variables in a natural way through a network topology. Because dependencies are expressed qualitatively as links between nodes, one can structure the domain knowledge qualitatively before any numeric probabilities need be assigned. The graphical representation also makes explicit the structure of the domain model: a link indicates a causal relation or known association. The encoding of independencies in the network topology admits the design of efficient procedures for performing computations over the network. A further advantage of the graphical representation is the perspicuity of the resulting domain model. Finally, since Bayesian networks represent uncertainty using standard probability, one can collect the necessary data for the domain model by drawing directly on published statistical studies.

A Bayesian belief network—a graphical representation of probabilistic information—is a directed acyclic graph. The graph is "directed" in that the links between nodes have directionality, that is, they are "one way." The graph is "acyclic" in that it cannot contain cycles or "feedback" loops. The nodes of the network represent random variables (stochastic)—uncertain quantities—which take on two or more possible values or states. The states of a node define the set of possible values a node can be in at any one time. Each state is associated with a probability value; for each node, these probability values sum to 1. The states for any node are mutually exclusive and completely exhaustive. The directed links signify the existence of direct causal influences or class-property relationships between the connected nodes. The strengths of these nodes are quantified by conditional probabilities. In this formalism, variables are given numerical probability values signifying the degree of belief accorded them, and the values are combined and manipulated according to the rules of standard probability theory.

A Bayesian network contains two types of nodes: nodes with parents and nodes without. A node with at least one parent is represented graphically with a directed link connecting the parent node to the child node. In Bayesian terminology the parent node influences the child node. A node with a set of parents is conditioned on that parent set. A node with no parents is represented graphically with no directed links coming into the node. This latter type of node represents a prior probability assessment and is represented or quantified by an unconditioned prior probability representing prior knowledge.

The strengths of influences between the nodes are represented with conditional-probability matrices associated with the connecting links. For example, if node Z has two parent nodes X and Y, the conditional probability matrix specifies the probabilities of the possible values that Z can assume given all possible combinations of values that X and Y can assume.

The prior and conditional probability values used to build a Bayesian network can be derived directly from published values of sensitivity and specificity and collected from expert opinion.

The primary operation of a Bayesian network is the computation of posterior probabilities. A posterior probability of a variable is the probability distribution for this variable given all its conditioning variables. This inference operation consists of specifying values for observed variables, e.g., setting a node state to one, and computing the posterior probabilities of the remaining variables. The mathematics used in a Bayesian network is described as follows:

Let X be a random variable with n possible states, $x_1, \ldots, x_n$. Let Y be a random variable with m possible states, $y_1, \ldots, y_m$. The probability of a variable X, P(X), is a real number in the interval 0 to 1. P(X)=1 if and only if the event X is certain.

The probability of any event X being in state $x_i$ is denoted by $P(X=x_i)=p$, where $p$ is the degree of belief accorded to $X$ being in state $x_i$.

The conditional probability of any event X being in state $x_i$ given a context Y is denoted by $P(X=x_i|Y)=p$, where $p$ is the degree of belief accorded to $X$ given the context $Y$.

The joint probability of any events X being in state $x_i$ and Y being in state $y_j$ is denoted by $P(X=x_i, Y=y_j)=p$, where $p$ is the degree of belief accorded to $X=x_i$ and $Y=y_j$.

The probability distribution of a node X with possible states $x_1, x_2, \ldots, x_n$, is denoted by $P(X)=(x_1, x_2, \ldots, x_n)$, given $x_i \geq 0$ and $\Sigma x_i = 1$, where $x_i$ is the probability of $X$ being in state $x_i$.

The product rule in probability is denoted by $$P(X|Y) \cdot P(Y) = P(X,Y). \qquad [1]$$

The probability distribution of X can be calculated from the joint probability distribution, P(X,Y), by summing over the partitions as denoted by $$P(X) = \sum_{j=1}^{m} P(X, Y). \qquad [2]$$

The inversion formula (Bayes Theorem) in probability is denoted by $P(Y|X=e)=P(X=e|Y) \cdot P(Y)/P(X=e)$, where $e$ is user-observed evidence. [3]

A conditional probability distribution is all combinations of the variable X conditioned on its conditioning variable Y. The distribution will contain (number of possible states in X)·(number of possible states in Y) entries. For example, if X is a node with two possible states $x_1$, $x_2$ and Y is a node with three possible states $y_1$, $y_2$, $y_3$, then P(X|Y) is the conditional probability table (vector) of size 2·3=6 containing the real numbers $P(x_i|y_j)$ denoted as shown in FIG. 1. For each state $y_j$ of Y, where i=1, ..., n and j=1, ..., m $$\sum_{i=1,\ldots,n} p(x_i | y_j) = 1.$$

A joint probability distribution is all combinations of the variable X and the variable Y. The distribution will contain (number of possible states in X)·(number of possible states in Y) entries. The joint probability P(X,Y) is calculated using the product rule $P(X|Y) \cdot P(Y) = P(X,Y)$ as shown in FIG. 2. In FIG. 2, each value $p(x_i, y_j)$ is $p(x_i, y_j) \cdot p(y_j)$, for i=1, ..., n and j=1, ..., m The sum of all the joint combinations equals 1.

$$\sum_{i=1, j=1}^{n,m} P(X, Y) = 1$$

A shortcoming of Bayesian networks in automated medical reasoning is the difficulty users have understanding and trusting the systems. Physicians generally will not accept and act on a computer system's advice without knowing the basis for the system's decision. The users' trust in these systems depends upon their ability to interact with the system and their ability to obtain understandable explanations. Although Bayesian networks are capable of "explaining" their reasoning, which is an important advantage over ANNs, Bayesian networks are difficult to understand because they are composed of large numbers of numeric relationships that interact in nonintuitive ways. For any node N, each of its state values S can at once serve two purposes. It can represent a conclusion to be evaluated given some evidence E; P (N=S|E). It also can represent evidence for some other conclusion H; P (H|N=S). What emerge are chains of influence, corresponding to systems of conditional probability equations through which changes to probability values propagate. Additionally, numerical relations alone do not provide information about their origin. Thus, an effective computer-aided decision support tool employing an inference system must be able to generate explanations of its reasoning for the physicians and patients who use it.

SUMMARY OF THE INVENTION

It is desirable to be able to make medical diagnoses using an inference system that provides a meaningful explanation of its reasoning, preferably using an interactive multimodal explanation generation system.

Thus, the instant invention is a computer-aided decision support system including a reasoning component and an interactive multimodal explanation generation system. In one form, the reasoning component is a Bayesian network inference engine, and the interactive multimodal explanation generation system includes a multimodal interactive user interface for receiving multimodal inputs from a user and for presenting multimodal outputs to the user; a knowledge representation module in communication with the multimodal interactive user interface and with the Bayesian network inference engine; and a multimodal discourse module in communication with the knowledge representation module and with the multimodal interactive user interface. In another form, the multimodal discourse module comprises an explicit discourse history structure and an explanation component. In still another form, the multimodal interactive user interface comprises an input module and an output module, the input module in communication with the knowledge representation module, and the output module in communication with the multimodal discourse module.

In another form, the instant invention comprises a method of generating interactive multimodal explanations in a diagnostic support tool using a Bayesian network inference engine. In this form, the invention comprising the steps of waiting for an utterance from a user; constructing an input object from the utterance, the input object identifying a modality, a sequence, and a content of the utterance; inserting the input object into an input stream; sending the input stream to a knowledge representation module; and parsing and encoding the input object in the knowledge representation module into an abstract statement. In one form of this invention, the parsing and encoding step includes the steps of defining a statement type, defining a statement origin, defining a statement modality, and defining a statement context for each input object. The may then be communicated to a multimodal discourse module and stored in a discourse history structure. In yet another form, the invention further comprises the steps of generating an inquiry in the multimodal discourse module; communicating the inquiry to the knowledge representation module; processing the inquiry in the knowledge representation module; requesting probability calculations from the Bayesian network inference engine via the knowledge representation module based upon the processed inquiry; and passing the probability calculations to the multimodal discourse module.

In a third form, the instant invention comprises a method of generating interactive multimodal explanations during a dialog between system participants, including a decision support tool and a user, the decision support tool using a Bayesian network inference engine. In this form, the invention comprising the steps (A) receiving multimodal inputs from a user; (B) synthesizing the multimodal inputs into a single sequenced stream of events; (C) communicating the sequenced stream of events to a knowledge representation module; (D) generating, within the knowledge representation module, an abstract statement from the sequenced stream of events; and (E) storing the abstract statement into an explicit discourse history structure comprising part of a multimodal discourse module. In this form of the invention, step (D) may further comprise the steps of (i) syntactically processing the sequenced stream of events; (ii) semantically processing the sequenced stream of events; and (iii) contextually processing the sequenced stream of events. Alternatively, step (D) may further comprises the steps of (i) reading a lexicon file, comprising lexicon words and corresponding lexicon semantic word types; (ii) storing the lexicon words and corresponding lexicon semantic word types in a lexicon structure; (iii) parsing the sequenced stream of events into noun phrases and verb phrases; (iv) assigning a semantic type to each parsed phrase; (v) storing the parsed phrases and their assigned semantic phrase types in a chart data structure; (vi) comparing each stored parsed phrase and its assigned semantic phrase type from the chart data structure to the lexicon words and corresponding lexicon semantic word types stored in the lexicon structure trying to match patterns; and (vii) generating the abstract statement for matched patterns.

In a third form, the instant invention comprises a method of generating interactive multimodal explanations comprising the steps of receiving multimodal inputs from a user; synthesizing the multimodal inputs into a single sequenced stream of events; communicating the sequenced stream of events to a knowledge representation module; parsing and encoding the sequenced stream of events into an abstract statement; and using the abstract statement in reasoning tasks. The parsing and encoding step may further comprises the steps of syntactically, semantically, and contextually processing the abstract statement.

In a fifth form, the instant invention comprises a method of providing computer-aided decision support including the steps of initializing an inference engine; initializing a semantic network structure; initializing a discourse structure; initializing a parser; reading a lexicon file; waiting for user input; receiving multimodal inputs from a user; determining a type of input received; and processing the input based upon the determined type. If the type of input is evidence, it is processed by storing the evidence in an inference engine evidence vector; storing the evidence in a semantic network structure; determining a sensitivity based upon the evidence; and storing the determined sensitivity in the semantic network structure. If, on the other hand, the type of input is a Professor question, it is processed by determining which node is under consideration; interrogating the semantic network structure for node information; preparing the information for display; and constructing display specifications for displaying the information. Finally, if the type of input is a user question, it is processed by first determining whether the input is understood. If it is not understood, the input is processed by interrogating the discourse structure for context; formulating a clarifying question; and the clarifying question to the user. If, on the other hand, the question is understood, the input is processed by generating an abstract concept; storing the abstract concept in a discourse structure; and determining an action to take based upon the abstract concept. If risk information is desired, the system calculates the risk, displays it, and offers an explanation of the displayed result. If an explanation is desired, the system interrogates the discourse structure for context; interrogates the semantic network structure for an answer; constructs an explanation; and constructs display specifications for displaying the explanation.

A more detailed explanation of the invention is provided in the following description and claims, and is illustrated in the accompanying figures.

BRIEF DESCRIPTION OF THE DRAWINGS

FIG. 1 is a conditional probability, $P(X|Y)$, vector;

FIG. 2 is a joint probability, $P(X, Y)$, vector;

FIG. 4 is the definitions of network's nodes and their possible states;

FIGS. 5A–5J is the demographic risk factor, conditional probability of breast cancer given age, age of menarche, age of first birth, and number of relatives with a history of breast cancer;

FIG. 6 is the demographic risk factor, prior probability for age;

FIG. 7 is the demographic risk factor, prior probability for age of menarche;

FIG. 8 is the demographic risk factor, prior probability for age of first birth;

FIG. 9 is the demographic risk factor, prior probability for number of relatives with a history of breast cancer;

FIG. 10 is the demographic risk factor, prior probability for previous biopsy at same site;

FIG. 11 is an indirect mammographic indication, conditional probability of architectural distortion given breast cancer and previous biopsy at same site;

FIG. 12 is an indirect mammographic indication, conditional probability of asymmetry given breast cancer;

FIG. 13 an indirect mammographic indication, conditional probability of developing density given breast cancer;

FIG. 14 is an indirect mammographic indication, conditional probability of dilated duct given breast cancer;

FIG. 15 is a direct mammographic indication, conditional probability of mass given breast cancer;

FIG. 16 is a direct mammographic indication, conditional probability of calcification given breast cancer;

FIG. 17 is a direct mammographic indication, conditional probability of tumor location given mass;

FIG. 18 is a direct mammographic indication, conditional probability of mass margin given mass;

FIG. 19 is a direct mammographic indication, conditional probability of mass density given mass;

FIG. 20 is a direct mammographic indication, conditional probability of halo sign given mass;

FIG. 21 is a direct mammographic indication, conditional probability of mass size given mass;

FIG. 22 is a direct mammographic indication, conditional probability of calcification shape given calcification;

FIG. 23 is a direct mammographic indication, conditional probability of number in cluster given calcification;

FIG. 24 is a direct mammographic indication, conditional probability of cluster shape given calcifications;

FIG. 25 is a direct mammographic indication, conditional probability of calcification density given calcification;

FIG. 26 is a direct mammographic indication, conditional probability of calcification size given calcification;

FIG. 27 is a direct mammographic indication, conditional probability of calcification arrangement given calcification;

FIG. 28 is a physical indication, conditional probability of pain given breast cancer;

FIG. 29 is a physical indication, conditional probability of nipple discharge given breast cancer;

FIG. 30 is a physical indication, conditional probability of palpable mass given mass;

FIG. 31 depicts the format of an evidence vector;

Figure 32:
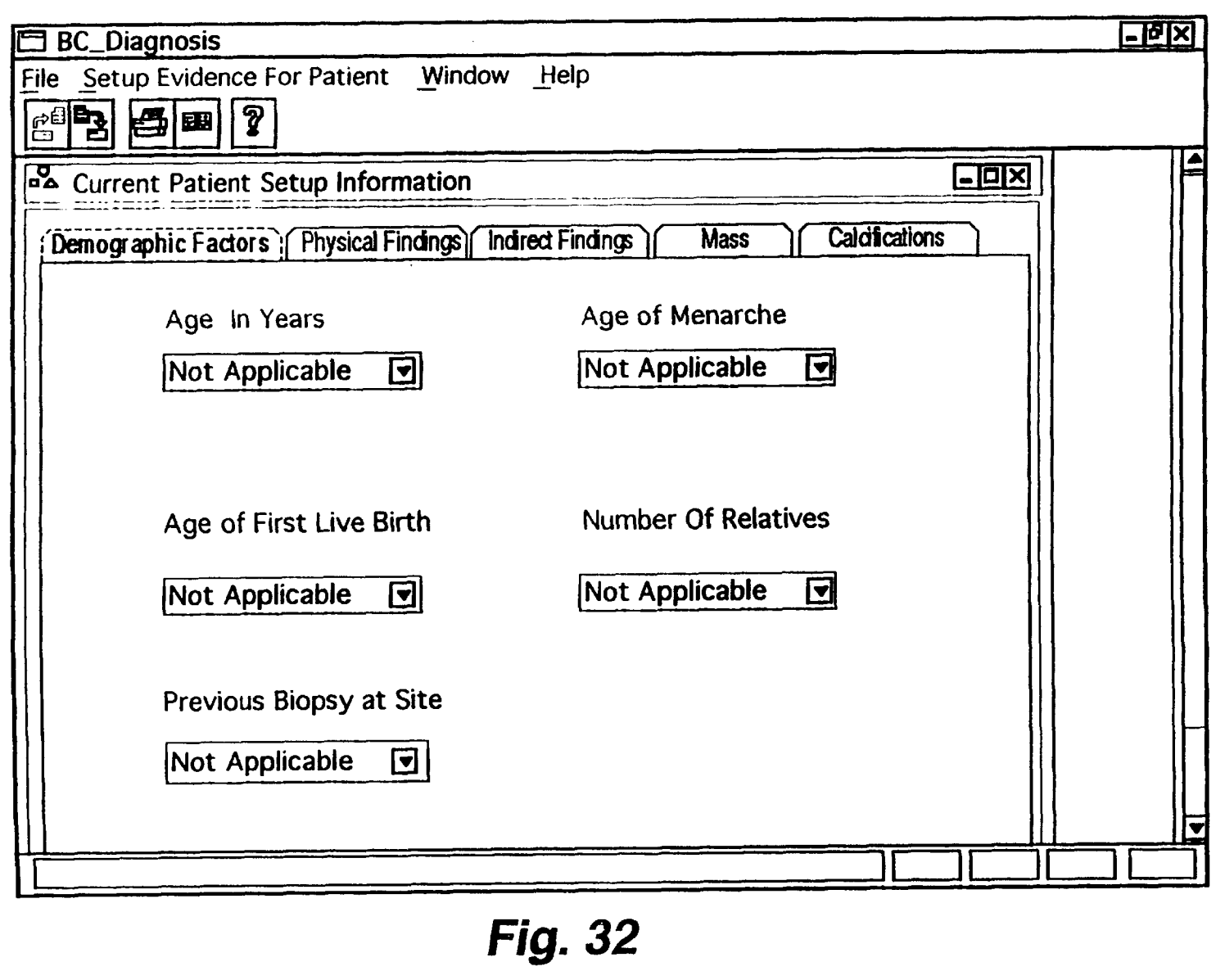

FIG. 32 is a sample data entry screen for demographic factors;

FIGS. 38A and 38B depict the general logic flow of the inference system;

FIG. 40 is a table providing a partial list of possible statement types with descriptions;

FIG. 41 is a table of possible modality types;

FIG. 42 is a table providing a partial list of possible statement contexts with descriptions;

FIG. 43 is a table providing a partial list of possible semantic types with descriptions;

DESCRIPTION OF THE PREFERRED EMBODIMENT

Bayesian networks used in the medical field can express the relationships between diagnoses, physical findings, laboratory test results, and imaging study findings. Physicians can determine the a priori ("pre-test") probability of a disease, and then incorporate laboratory and imaging results to calculate the a posteriori ("post-test") probability. This invention employs a Bayesian network in a decision support tool used in the interpretation of mammograms for the differentiation between benign and malignant lesions of the breast, i.e., detecting breast cancer.

The inference system is logically divided into two components. The first is the knowledge base, and the second is the logic that performs the belief updating when evidence is entered. The invention assumes all the evidence pertains to one particular site identified by mammography. The invention infers the posterior probability of breast cancer at that site based on the available evidence.

System Knowledge Base

Figure 3:
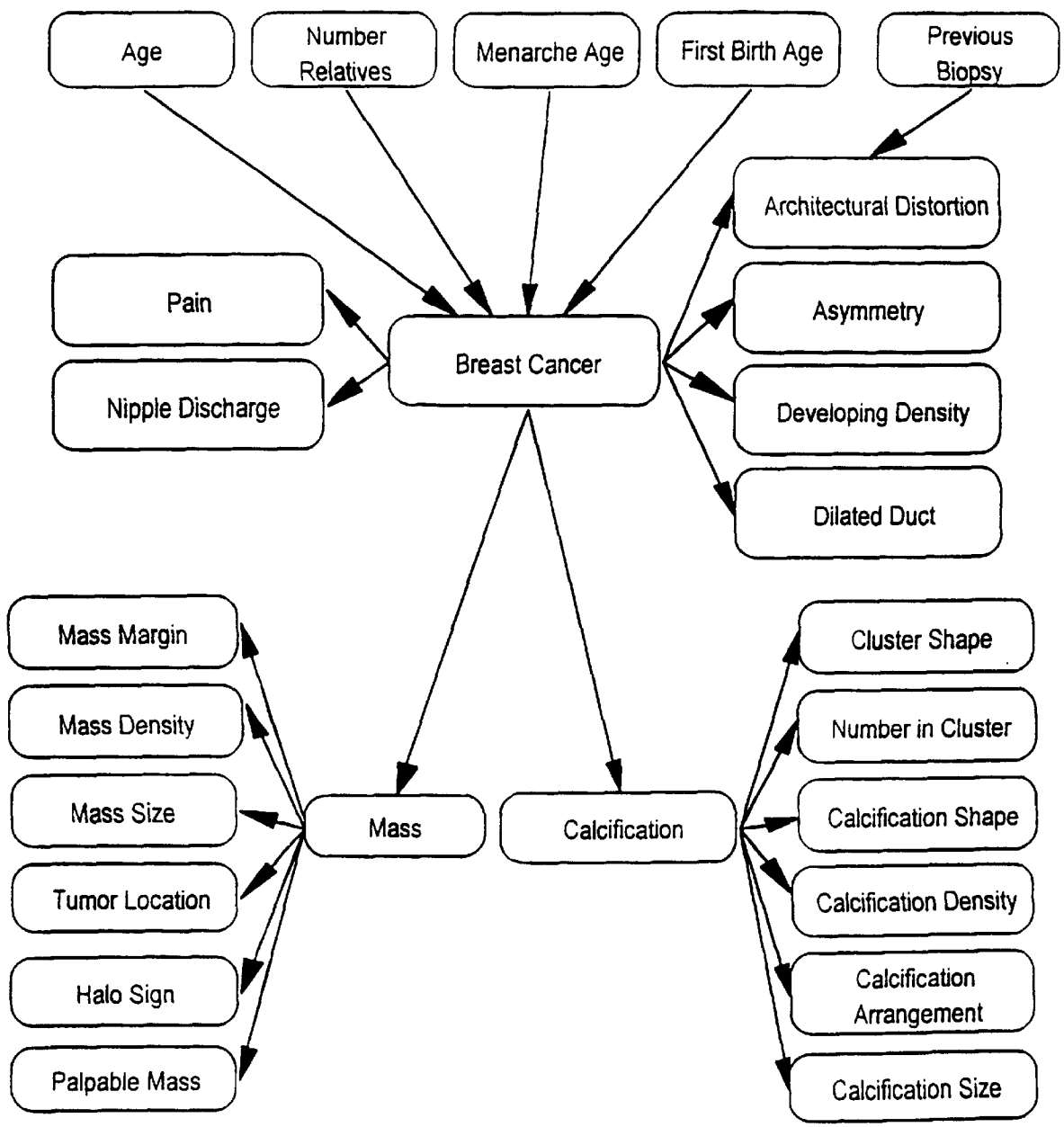
FIG. 3 is a spider chart showing the relationships between the 26 nodes.
Figure 33:
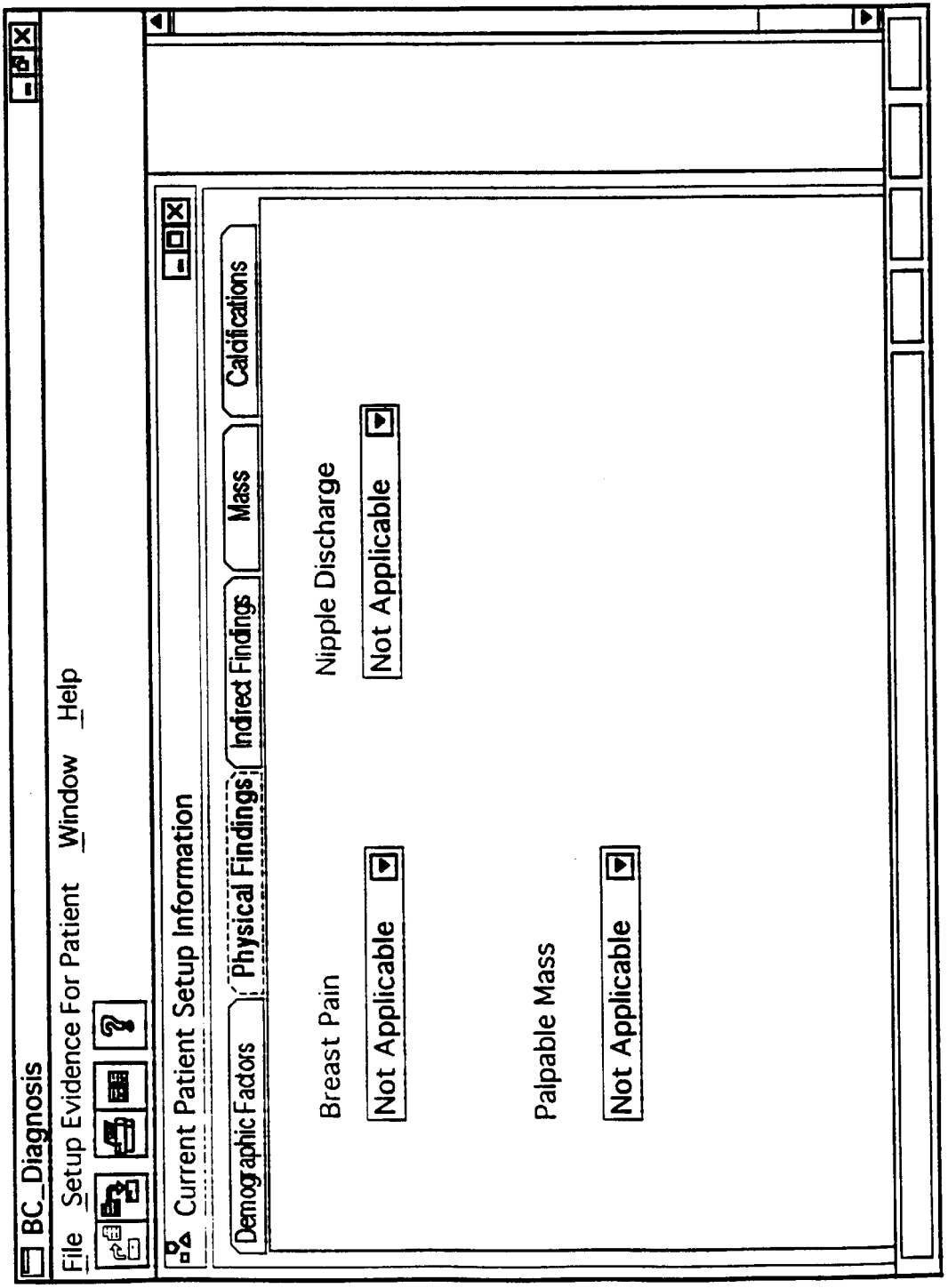
FIG. 33 is a sample data entry screen for physical findings.
Figure 34:
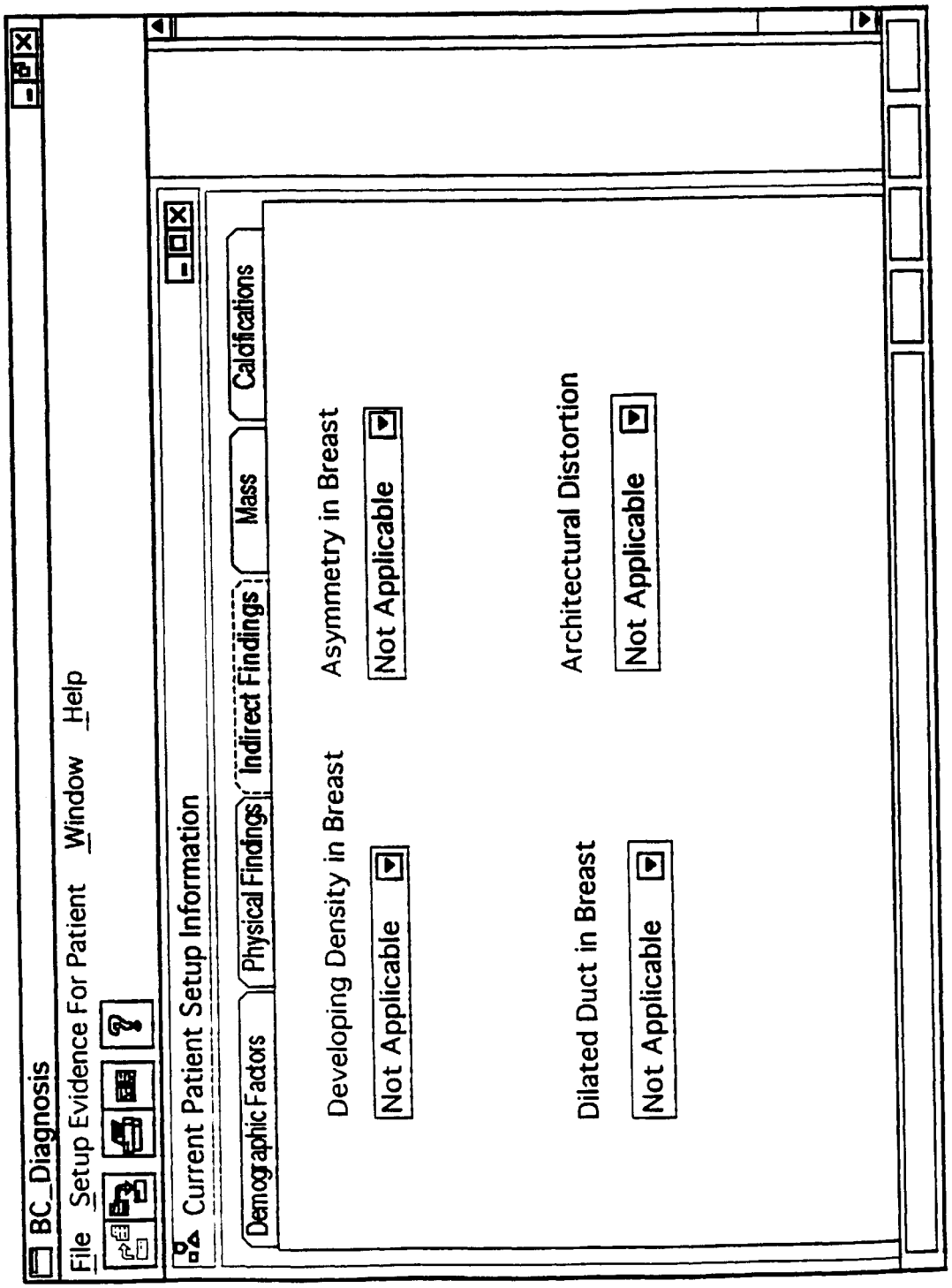
FIG. 34 is a sample data entry screen for indirect mammographic findings.
Figure 35:
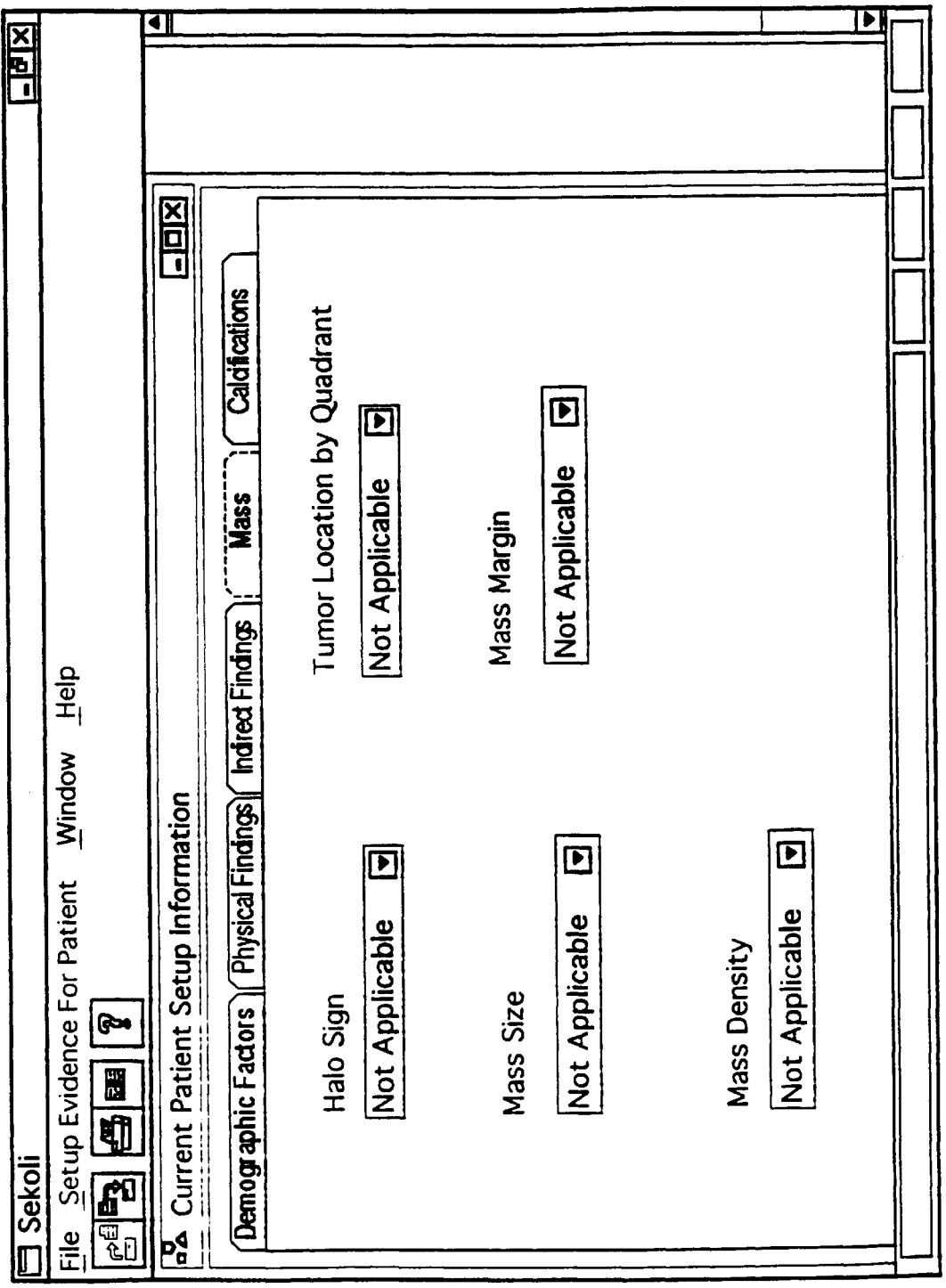
FIG. 35 is a sample data entry screen for direct mammographic mass findings.
Figure 36:
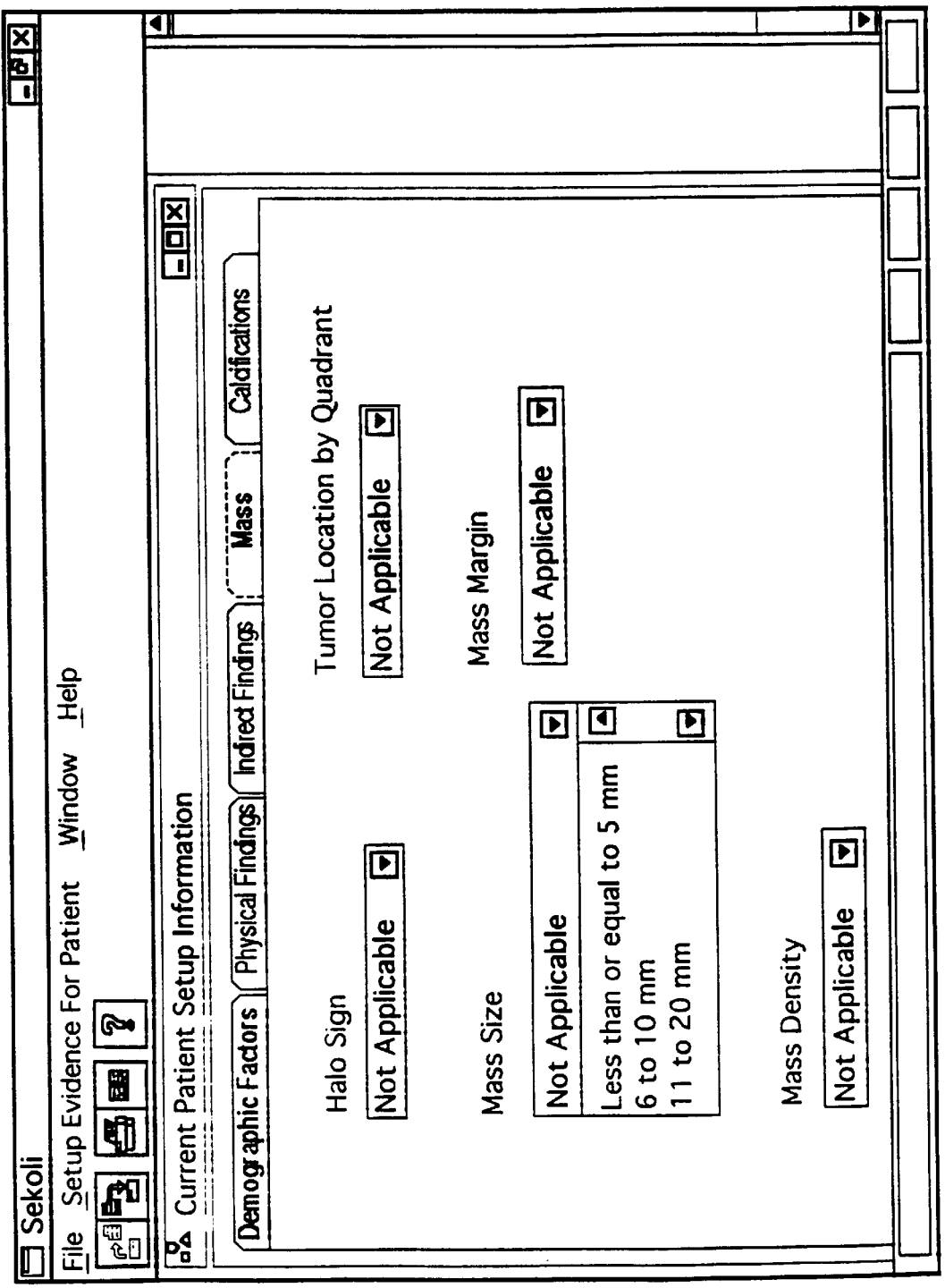
FIG. 36 is a second sample data entry screen for direct mammographic mass findings, shown with the Mass Size drop-down box open.
Figure 37:
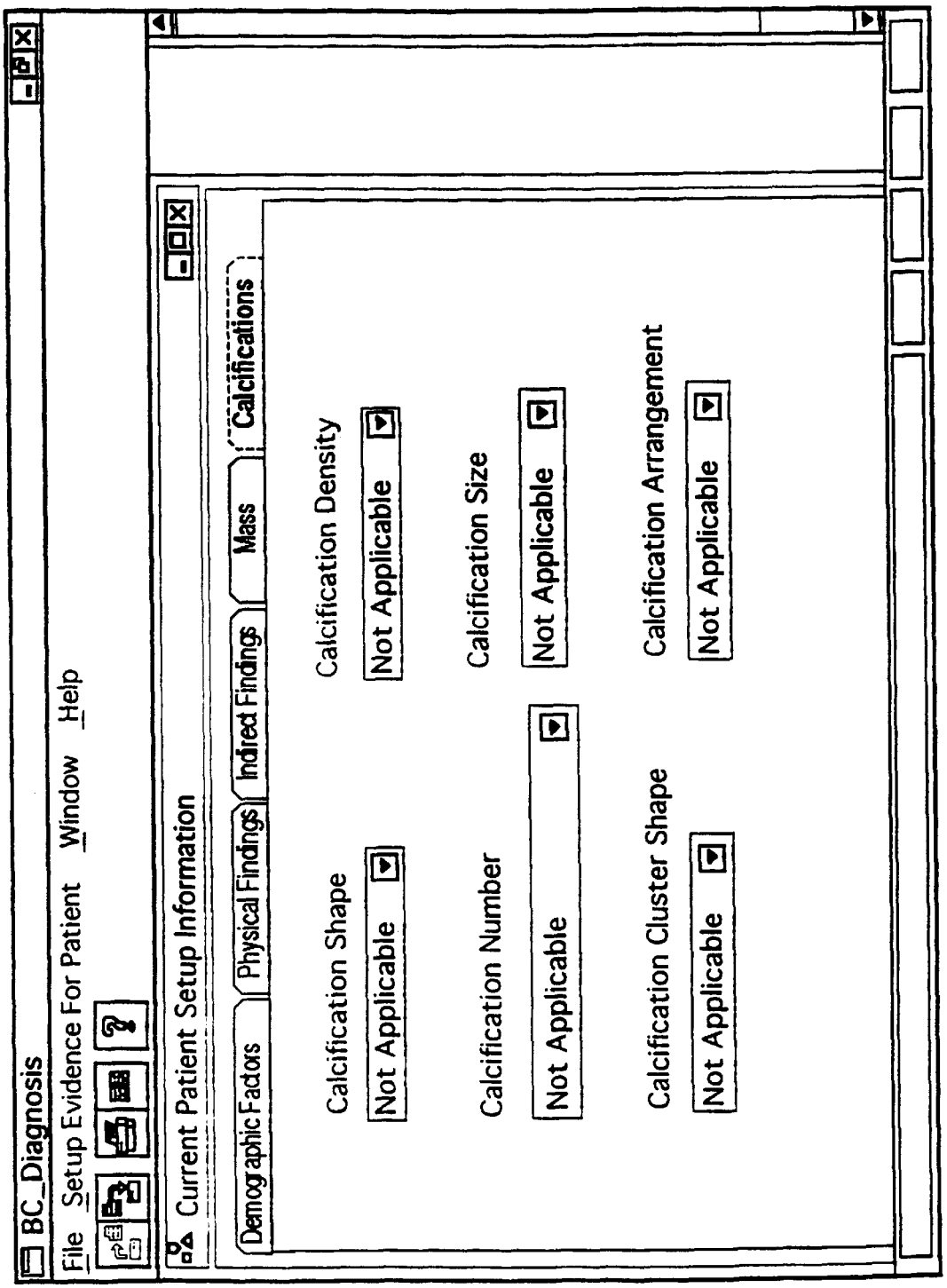
FIG. 37 is a sample data entry screen for direct mammographic calcification findings.

The knowledge base is an encoding of the breast cancer domain in the format of a Bayesian network and contains information used by physicians in diagnosing breast cancer. The topology of the network is presented graphically in FIG. 3. One of the twenty-six nodes of the network is the hypothesis node (i.e., Breast Cancer), which is an inferred node that does not receive direct input from the user. The Mass and Calcification nodes in the center of FIG. 3 are also inferred nodes that do not receive direct input from the user. The remaining twenty-three nodes represent observable evidence. Wherever possible, standardized terminology as proposed in the American College of Radiology's Breast Imaging Reporting and Data Systems lexicon is used.

Breast pain, nipple discharge, and skin thickening are reported by women with breast cancer, but few early-stage cancers are detected by these indicators. The risk factors and physical findings alone are not sufficiently sensitive for malignancy determinations; thus, the use of mammography is an important screening tool.

Benign and malignant masses are differentiated using margin, density, location, size, and the presence of the halo sign. Round, low-density masses with smooth, sharply defined margins are more likely to be benign. Malignant masses are more likely to be high-density, stellate, spiculated, or knobby, with poorly defined margins. Frequently, though, masses are classified as indeterminate, not clearly benign or malignant. Instead of spiculations, many malignant masses display poorly defined or irregular margins.

Calcifications can occur with or without an associated mass. The attributes of size, shape, density, distribution pattern, and number are examined when differentiating between benign and malignant calcifications. Benign calcifications are typically larger (1–4 mm in diameter), coarse, round or oval, and monomorphic (uniform in size and shape). Their distribution pattern is typically scattered or diffuse. If the calcifications are clustered, they number fewer than five per cluster. Some benign calcifications display bizarre, irregular shapes, but because of their large size are considered noncancerous. Malignant calcifications are typically microscopic (<0.5 mm in diameter) and fine, linear branching or rod-shaped, punctate- or stellate-shaped, and pleomorphic (varying in size and shape). In general, the greater the number of calcifications in a cluster, the greater the likelihood of malignancy. As with breast masses, calcifications can display indistinct characteristics making the determination of malignancy difficult. Both benign and malignant calcifications can appear tiny and clustered. Typically, malignant calcifications present with a wide range in size, shape, and density.

Almost 20% of nonpalpable cancers can present with neither mass nor calcification, but with subtle or "indirect"

signs of malignancy. Architectural distortion or a developing density (an enlarging area of glandular-tissue density) are strongly indicative of cancer. Dilated mammary ducts and asymmetrical parenchymal density (i.e., greater density in one breast) are less effective indicators. Surgical interventions can confound the diagnosis: a breast biopsy can produce architectural distortion.

The information contained in the knowledge base has been categorized into three primary areas: demographic factors (also referred to as patient-history information), physical examination findings, and mammographic findings extracted by experienced radiologist. Mammographic findings are further subdivided into direct and indirect findings. FIG. 4 presents this categorization and the possible states of each of the twenty-six nodes depicted in FIG. 3. The noninferred portion of the network's knowledge base incorporates five demographic factors (age in years, age of menarche, age of first live birth, number of first order relatives with cancer, previous biopsy at site), three physical examination findings (breast pain, nipple discharge, palpable mass), four indirect mammographic findings (architectural distortion, asymmetry in breast, developing density in breast, dilated duct in breast), and eleven direct mammographic findings (mass margin, mass density, mass size, halo sign, tumor location by quadrant, calcification cluster shape, calcification number, calcification shape, calcification density, calcification arrangement, calcification size).

The prior and conditional probability vectors that quantify the links in the network knowledge base are presented in FIGS. 5A–5J and 6–30. These probabilities were extracted from peer-reviewed medical literature, census data, health statistics reports, and expert opinion.

Initial prior probability values are assigned to the demographic nodes: node 0 (age, FIG. 6); node 1 (menarche age, FIG. 7); node 2 (first birth age, FIG. 8); node 3 (number of relatives, FIG. 9); and node 13 (previous biopsy, FIG. 10). Age statistics were obtained from the National Cancer Institutes and the U.S. Census Bureau, Population Division. Statistics for age of menarche were acquired from the Department of Health, Education, and Welfare, Vital and Health Statistics. Population and Vital Statistics, Statistical Record of Women World wide provided statistics for age of first live birth. The number of first order relatives with a known history of breast cancer was estimated based upon information.

Initial conditional probability values are assigned to the remaining nodes: node 4 (breast cancer, FIGS. 5A–5J); node 5 (mass, FIG. 15); node 6 (calcification, FIG. 16); node 7 (asymmetry, FIG. 12); node 8 (developing density, FIG. 13); node 9 (dilated duct, FIG. 14); node 10 (breast pain, FIG. 28); node 11 (nipple discharge, FIG. 29); node 12 (architectural distortion, FIG. 11); node 14 (tumor location, FIG. 17); node 15 (mass margin, FIG. 18); node 16 (mass density, FIG. 19); node 17 (halo sign, FIG. 20); node 18 (mass size, FIG. 21); node 19 (palpable mass, FIG. 30); node 20 (calcification shape, FIG. 22); node 21 (number in cluster, FIG. 23); node 22 (cluster shape, FIG. 24); node 23 (calcification density, FIG. 25); node 24 (calcification size, FIG. 26); and node 25 (calcification arrangement, FIG. 27).

Epidemiologic investigations have reported several risk factors that may increase a woman's chance of developing breast cancer. The incidence of breast cancer increases with age, and is higher after menopause. Early menarche, late childbearing (first live birth after age 30 years or nulliparity), and first order relatives with breast cancer increase the probability of malignancy. The values presented in the table comprising FIGS. 5A–5J, which presents the conditional probability of developing breast cancer considering the risk factors of age, age of menarche, age of first birth, and number of first order relatives with a history of breast cancer, were computed (using data retrieved from the National Cancer Institute's Surveillance Program) by multiplying the relative risk factors by the base risk factors for a specific age group to obtain an adjusted probability.

System Logic

The logic component of the system, which has been programmed using C++, is based on standard probability theory. This software system is a dedicated inference engine that uses Bayesian network theory and techniques to calculate the posterior probability of breast cancer given each case's constellation of observable demographic, physical, and mammographic evidence. The basic calculation formulas used to perform the evidence propagation and belief update of all network nodes are standard probability formulas provided in the background section. The system uses a probability of threshold for breast cancer of 15% (which approximates the positive predictive value of mammographic suspicion) to determine the presence of breast cancer.

The user of this system must input information with respect to predefined demographic factors, physical findings, and mammographic findings. Information for each factor, however, need not be input. The system uses this information to calculate a posterior probability of the presence of breast cancer. The system, additionally, generates an explanatory report describing its reasoning process. The system runs in single record mode, allowing the user to enter information for a single case and process that record immediately, and in batch record mode, allowing the user to enter multiple records and process the batch of records at one time.

The user interface presents a fixed textual input form to which the user identifies relevant information. The input format explicitly reflects the structure of the previously described knowledge base. The user interface can be a Microsoft® Windows™-based program requiring the user to enter data using Windows gadgets (see, e.g., FIGS. 32–37), a hypertext document for use on the world wide web, or an input form generated from a commercial database package. The output of an input session is a formatted evidence vector that is translated into probabilistic information for use by the system. An evidence vector is processed one at a time by the system.

The system propagates the evidence through the network and calculates the posterior probability of the hypothesis node, Breast Cancer, given each piece of user-observed evidence. The output from the system is a posterior probability indicating if breast cancer is present, and an English-text explanation of how the evidence vector with its constellation of user-entered evidence influenced the resulting probability.

Figure 38B:
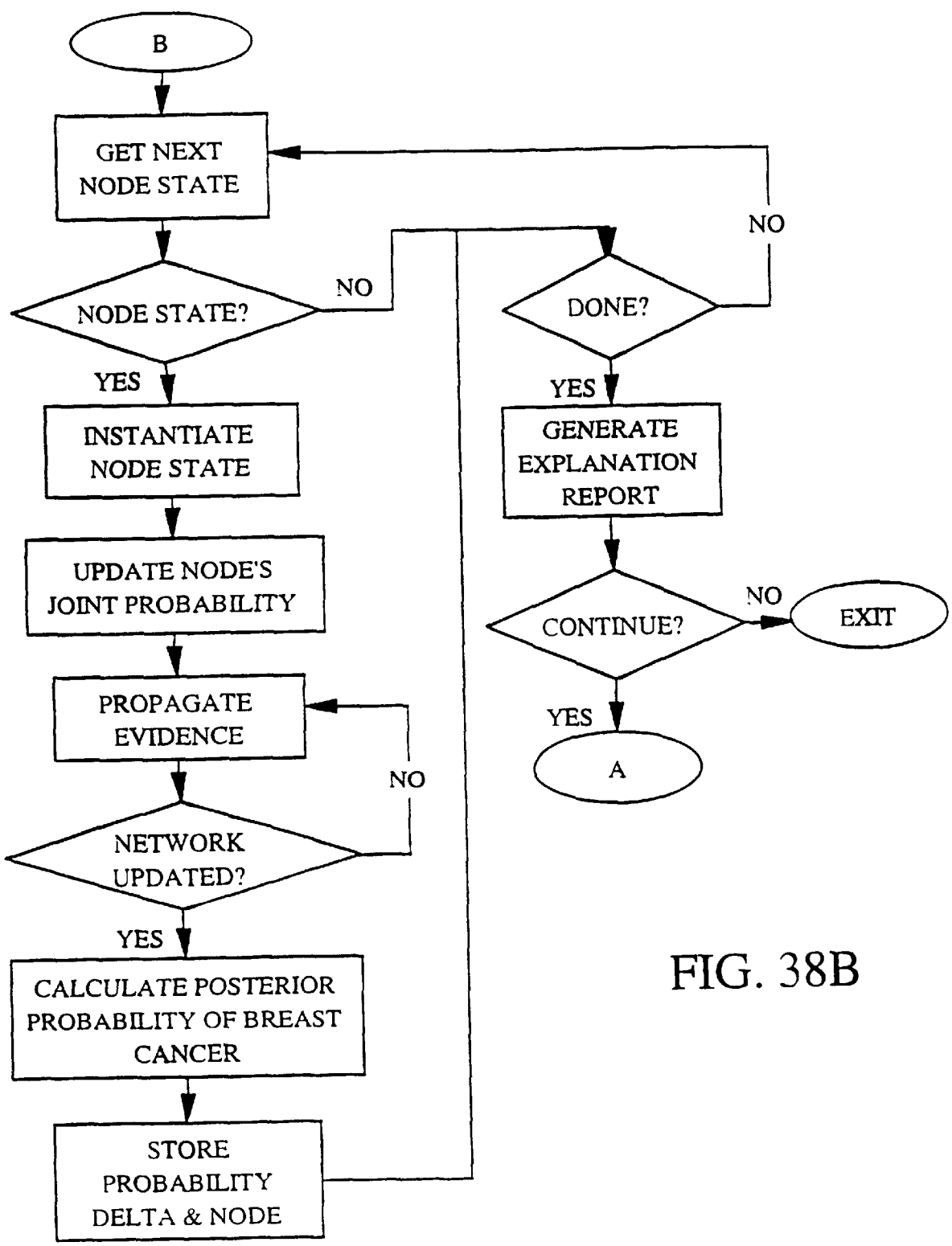

The general logic flow of the inference system is denoted with a flow chart in FIGS. 38A and 38B. If this is initial start up of the system, initial joint probability vectors are calculated and stored for each conditional probability vector. The initial prior and conditional probability vectors used for this calculation are presented in FIGS. 5A–5J and 6–30. The logic that converts the conditional probability distributions to joint probability distributions uses the product rule $P(X|Y,Z) \cdot P(Y) \cdot P(Z) = P(X, Y, Z)$. The conditional and joint distributions are stored internally as one-dimensional vectors (arrays). Each vector entry is a configuration of the variables, and the size (number of vector entries) of a particular vector is a function of the size—the product of the number of possible states—in each variable. For example, if X has n possible states, Y has m possible states, and Z has j possible states, the size of vector P(X, Y, Z) is the product of the number of all possible states for all the concerned variables:

$n \cdot m \cdot j = nmj.$

A vector entry contains a configuration (each combination of possible states) of the variables:

$\{X=x_1, Y=y_1, Z=z_1\}$ through $\{X=x_n, Y=y_m, Z=z_j\}.$

Once all initial joint probability vectors are calculated and stored, the initial prior probabilities (unconditional probability distribution) for each node in the network are calculated and stored. This calculation is done for every node in a joint vector. For two variables X and Y, where X has n possible states and Y has m possible states, the computation for the probability distribution of X is done by summing over all combinations of the conditioned variable Y:

$$P(X = x_i) = \sum_{j=1}^{m} P(X, Y).$$

The prior probability for any variable in a joint vector is computed by conditioning it on all the combinations of the conditioned variables. The prior unconditioned probabilities are stored.

The calculations are done in a predefined sequence such that conditional distributions to be converted to joint distributions, have their prior probability values already calculated:

Calculate joint vector:

$p$(breast cancer|age, number of relatives, age of menarche, first live birth)·$p$(age)·$p$(number of relatives)·$p$(age of menarche)·$p$(first live birth)=$p$(breast cancer, age, number of relatives, age of menarche, first live birth)

Calculate prior probability of breast cancer:

$p$(breast cancer=present, absent)=Σ(age, number of relatives, age of menarche, first live birth)

Calculate joint vector:

$p$(pain|breast cancer)·$p$(breast cancer)=$p$(pain, breast cancer)

Calculate prior probability of pain:

$p$(pain=present, absent)=Σ$p$(pain, breast cancer)

Calculate joint vector:

$p$(nipple discharge|breast cancer)·$p$(breast cancer)=$p$(nipple discharge, breast cancer)

Calculate prior probability of nipple discharge:

$p$(nipple discharge=present, absent)=Σ$p$(nipple discharge, breast cancer)

Calculate joint vector:

$p$(architectural distortion|breast cancer)·$p$(breast cancer)=$p$(architectural distortion, breast cancer)

Calculate prior probability of architectural distortion:

$p$(architectural distortion=present, absent)=Σ$p$(architectural distortion, breast cancer)

Calculate joint vector:

$p$(asymmetry|breast cancer)·$p$(breast cancer)=$p$(asymmetry, breast cancer)

Calculate prior probability of asymmetry:

$p$(asymmetry=present, absent)=Σ$p$(asymmetry, breast cancer)

Calculate joint vector:

$p$(developing density|breast cancer)·$p$(breast cancer)=$p$(developing density, breast cancer)

Calculate prior probability of developing density:

$p$(developing density=present, absent)=Σ$p$(developing density, breast cancer)

Calculate joint vector:

$p$(dilated duct|breast cancer)·$p$(breast cancer)=$p$(dilated duct, breast cancer)

Calculate prior probability of dilated duct:

$p$(dilated duct=present, absent)=Σ$p$(dilated duct, breast cancer)

Calculate joint vector:

$p$(mass|breast cancer)·$p$(breast cancer)=$p$(mass, breast cancer)

Calculate prior probability of mass:

$p$(mass=benign, malignant, NA)=Σ$p$(mass, breast cancer)

Calculate joint vector:

$p$(calcification|breast cancer)·$p$(breast cancer)=$p$(calcification, breast cancer)

Calculate prior probability of calcification:

$p$(calcification=benign, malignant, NA)=Σ$p$(calcification, breast cancer)

Calculate joint vector:

$p$(mass margin|mass)·$p$(mass)=$p$(mass margin, mass)

Calculate prior probability of mass margin:

$p$(mass margin=spiculated, irregular, relatively well-defined, NA)= Σ$p$(mass margin, mass)

Calculate joint vector:

$p$(mass density|mass)·$p$(mass)=$p$(mass density, mass)

Calculate prior probability of mass density:

$p$(mass density=low density, high density, NA)=Σ$p$(mass density, mass)

Calculate joint vector $p$(mass size|mass)·$p$(mass)=$p$(mass size, mass)

Calculate prior probability of mass size:

$p$(mass size=inSitu, <=5, 6–10, 11–20, >20, multiFocal, NA)= Σ$p$(mass size, mass)

Calculate joint vector:

$p$(tumor location|mass)·$p$(mass)=$p$(tumor location, mass)

Calculate prior probability of tumor location:

$p$(tumor location=UO, UI, LO, LI, RA, NA)=Σ$p$(tumor location, mass)

Calculate joint vector:

$p$(halo sign|mass)·$p$(mass)=$p$(halo sign, mass)

Calculate prior probability of halo sign:

$p$(halo sign=present, absent)=Σ$p$(halo sign, mass)

Calculate joint vector:

$p$(palpable mass|mass)·$p$(mass)=$p$(palpable mass, mass)

Calculate prior probability of palpable mass:

$p$(palpable mass=present, absent)=Σ$p$(palpable mass, mass)

Calculate joint vector:

$p$(cluster shape|calcification)·$p$(calcification)=$p$(cluster shape, calcification)

Calculate prior probability of cluster shape:

$p$(cluster shape=punctate, round, linear, variable, NA)=Σ$p$(cluster shape, calcification)

Calculate joint vector:

$p$(number in cluster|calcification)·$p$(calcification)=$p$(number in cluster, calcification)

Calculate prior probability of number in cluster:

$p$(number in cluster=<=5, 6–10, 11–15, 16–25, 26–50, >50, NA)= Σ$p$(number in cluster, calcification)

Calculate joint vector:

$p$(calcification shape|calcification)·$p$(calcification)=$p$(calcification shape, calcification)

Calculate prior probability of calcification shape:

$p$(calcification shape=linear branching, irregular, indeterminate, round, NA)=Σ$p$(calcification shape, calcification)

Calculate joint vector:

$p$(calcification density|calcification)·$p$(calcification)=$p$(calcification density, calcification)

Calculate prior probability of calcification density:

$p$(calcification density=1–2, 1–3, 2–3, 3–4, NA)=Σ$p$(calcification density, calcification)

Calculate joint vector:

$p$(calcification arrangement|calcification)·$p$(calcification)=$p$(calcification arrangement, calcification)

Calculate prior probability of calcification arrangement:

$p$(calcification arrangement=scattered, clustered, scattered & clustered, single, NA)=Σ$p$(calcification arrangement, calcification)

Calculate joint vector:

$p$(calcification size|calcification)·$p$(calcification)=$p$(calcification size, calcification)

Calculate prior probability of calcification size:

$p$(calcification size=0.05–0.1, 0.05–2, 0.01–1, 0.01–2, 1–3, NA)= Σ$p$(calcification size, calcification)

Calculate joint vector:

$p$(previous biopsy|breast cancer, architectural distortion)·$p$(breast cancer)·$p$(architectural distortion)=$p$(previous biopsy, breast cancer, architectural distortion)

Calculate prior probability of previous biopsy:

$p$(previous biopsy=present, absent)=Σ$p$(previous biopsy, breast cancer, architectural distortion)

I

Software Initialization

At program startup, the system enters an initial state. First, the member components—nodes and cliques—of the Bayesian network are created and initialized. Second, the Bayesian network is initialized. Third, the joint probability vectors and initial prior probability vectors are calculated and stored. Fourth, an evidence vector is created and initialized. The system is then in a wait state for user evidence to be entered by the graphical user interface in single-patient mode or multiple-patient mode.

Node Creation

The nodes represent the domain variables of the network. The 26 member nodes of the Bayesian network are created and initialized with the following default information:

number of possible states textual name of node for reports node number for identification number of parent nodes—nodes that are incoming to the current node number of children nodes—nodes that are outgoing from the current node the size of the associated joint vector, null if no joint vector is associated with the current node children nodes parent nodes clique the node is a member of prior probability vector conditional probability vector Node Age is created and defaulted as follows:

| | |
|---|---|
| number of possible states | 12 |
| name | Age |
| node number | 0 |
| number of parent nodes | 0 |
| number of children nodes | 1 |
| joint vector size | 0 |
| child node | Breast Cancer |
| parent nodes | none |
| clique | 0 |
| prior probability vector | FIG. 6 |
| conditional probability vector | none |

Node Age of Menarche is created and defaulted as such:

| | |
|---|---|
| number of possible states | 3 |
| name | Menarche |
| node number | 1 |
| number of parent nodes | 0 |
| number of children nodes | 1 |
| joint vector size | 0 |
| child node | Breast Cancer |
| parent nodes | none |
| clique | 0 |
| prior probability vector | FIG. 7 |
| conditional probability vector | none |

Node Age of First Birth is created and defaulted as follows:

| | |
|---|---|
| number of possible states | 4 |
| name | Birth |
| node number | 2 |
| number of parent nodes | 0 |
| number of children nodes | 1 |
| joint vector size | 0 |
| child node | Breast Cancer |
| parent nodes | none |
| clique | 0 |
| prior probability vector | FIG. 8 |
| conditional probability vector | none |

Node Number of Relatives is created and defaulted as follows:

| | |
|---|---|
| number of possible states | 3 |
| name | Relatives |
| node number | 3 |
| number of parent nodes | 0 |
| number of children nodes | 1 |
| joint vector size | 0 |
| child node | Breast Cancer |
| parent nodes | none |
| clique | 0 |
| prior probability vector | FIG. 9 |
| conditional probability vector | none |

Node Breast Cancer is created and defaulted as follows:

| | |
|---|---|
| number of possible states | 2 |
| name | Breast Cancer |
| node number | 4 |
| number of parent nodes | 4 |
| joint vector size | 864 |
| children nodes | Mass, Calcification, Asymmetry, Developing Density, Dilated Duct, Pain, Nipple Discharge, Architectural Distortion |
| parent nodes | Age, Menarche, Birth, Relatives |
| clique | 0 |
| prior probability vector | calculated by software |
| conditional probability vector | FIGS. 5A-5J |

Node Mass is created and defaulted as follows:

| | |
|---|---|
| number of possible states | 3 |
| name | Mass |
| node number | 5 |
| number of parent nodes | 1 |

-continued

| | |
|---|---|
| number of children nodes | 6 |
| joint vector size | 6 |
| children nodes | Tumor Location, Mass Margin, Mass Density, Halo Sign, Mass Size, Palpable Mass |
| parent node | Breast Cancer |
| clique | 1 |
| prior probability vector | calculated by software |
| conditional probability vector | FIG. 15 |

Node Calcification is created and defaulted as follows:

| | |
|---|---|
| number of possible states | 3 |
| name | Calcification |
| node number | 6 |
| number of parent nodes | 1 |
| number of children nodes | 6 |
| joint vector size | 6 |
| children nodes | Calc Shape, Calc Number, Calc Cluster Shape, Calc Density, Calc Size, Calc Arrangement |
| parent node | Breast Cancer |
| clique | 2 |
| prior probability vector | calculated by software |
| conditional probability vector | FIG. 16 |

Node Asymmetry is created and defaulted as follows:

| | |
|---|---|
| number of possible states | 2 |
| name | Asymmetry |
| node number | 7 |
| number of parent nodes | 1 |
| number of children nodes | 0 |
| joint vector size | 4 |
| children nodes | none |
| parent node | Breast Cancer |
| clique | 3 |
| prior probability vector | calculated by software |
| conditional probability vector | FIG. 12 |

Node Developing Density is created and defaulted as follows:

| | |
|---|---|
| number of possible states | 2 |
| name | Developing Density |
| node number | 8 |
| number of parent nodes | 1 |
| number of children nodes | 0 |
| joint vector size | 4 |
| children nodes | none |
| parent node | Breast Cancer |
| clique | 4 |
| prior probability vector | calculated by software |
| conditional probability vector | FIG. 13 |

Node Dilated Duct is created and defaulted as follows:

| | |
|---|---|
| number of possible states | 2 |
| name | Dilated Duct |
| node number | 9 |
| number of parent nodes | 1 |
| number of children nodes | 0 |
| joint vector size | 4 |
| children nodes | none |

-continued

| | |
|---|---|
| parent nodes | Breast Cancer |
| clique | 5 |
| prior probability vector | calculated by software |
| conditional probability vector | FIG. 14 |

Node Pain is created and defaulted as follows:

| | |
|---|---|
| number of possible states | 2 |
| name | Pain |
| node number | 10 |
| number of parent nodes | 1 |
| number of children nodes | 0 |
| joint vector size | 4 |
| children nodes | none |
| parent nodes | Breast Cancer |
| clique | 6 |
| prior probability vector | calculated by software |
| conditional probability vector | FIG. 28 |

Node Nipple Discharge is created and defaulted as follows:

| | |
|---|---|
| number of possible states | 2 |
| name | Nipple Discharge |
| node number | 11 |
| number of parent nodes | 1 |
| number of children nodes | 0 |
| joint vector size | 4 |
| children nodes | none |
| parent nodes | Breast Cancer |
| clique | 7 |
| prior probability vector | calculated by software |
| conditional probability vector | FIG. 29 |

Node Architectural Distortion is created and defaulted as follows:

| | |
|---|---|
| number of possible states | 2 |
| name | Architectural Distortion |
| node number | 12 |
| number of parent nodes | 2 |
| number of children nodes | 0 |
| joint vector size | 8 |
| children nodes | none |
| parent nodes | Breast Cancer, Previous Biopsy |
| clique | 8 |
| prior probability vector | calculated by software |
| conditional probability vector | FIG. 11 |

Node Previous Biopsy is created and defaulted as follows:

| | |
|---|---|
| number of possible states | 2 |
| name | Previous Biopsy |
| node number | 13 |
| number of parent nodes | 0 |
| number of children nodes | 1 |
| joint vector size | 0 |
| child node | Architectural Distortion |
| parent nodes | none |
| clique | 8 |
| prior probability vector | FIG. 10 |
| conditional probability vector | none |

Node Tumor Location is created and defaulted as follows:

| | |
|---|---|
| number or possible states | 6 |
| name | Tumor Location |
| node number | 14 |
| number of parent nodes | 1 |
| number of children nodes | 0 |
| joint vector size | 18 |
| children nodes | none |
| parent nodes | Mass |
| clique | 9 |
| prior probability vector | calculated by software |
| conditional probability vector | FIG. 17 |

Node Mass Margin is created and defaulted as follows:

| | |
|---|---|
| number of possible states | 4 |
| name | Mass Margin |
| node number | 15 |
| number of parent nodes | 1 |
| number of children nodes | 0 |
| joint vector size | 12 |
| children nodes | none |
| parent nodes | Mass |
| clique | 10 |
| prior probability vector | calculated by software |
| conditional probability vector | FIG. 18 |

Node Mass Density is created and defaulted as follows:

| | |
|---|---|
| number of possible states | 3 |
| name | Mass Density |
| node number | 16 |
| number of parent nodes | 1 |
| number of children nodes | 0 |
| joint vector size | 9 |
| children nodes | none |
| parent nodes | Mass |
| clique | 11 |
| prior probability vector | calculated by software |
| conditional probability vector | FIG. 19 |

Node Halo Sign is created and defaulted as follows:

| | |
|---|---|
| number of possible states | 3 |
| name | Halo Sign |
| node number | 17 |
| number of parent nodes | 1 |
| number of children nodes | 0 |
| joint vector size | 9 |
| children nodes | none |
| parent nodes | Mass |
| clique | 12 |
| prior probability vector | calculated by software |
| conditional probability vector | FIG. 20 |

Node Mass Size is created and defaulted as follows:

| | |
|---|---|
| number of possible states | 7 |
| name | Mass Size |
| node number | 18 |
| number of parent nodes | 1 |
| number of children nodes | 0 |
| joint vector size | 21 |
| children nodes | none |

-continued

| | |
|---|---|
| parent nodes | Mass |
| clique | 13 |
| prior probability vector | calculated by software |
| conditional probability vector | FIG. 21 |

Node Palpable Mass is created and defaulted as follows:

| | |
|---|---|
| number of possible states | 2 |
| name | Palpable Mass |
| node number | 19 |
| number of parent nodes | 1 |
| number of children nodes | 0 |
| joint vector size | 6 |
| children nodes | none |
| parent nodes | Mass |
| clique | 14 |
| prior probability vector | calculated by software |
| conditional probability vector | FIG. 30 |

Node Calcification Shape is created and defaulted as follows:

| | |
|---|---|
| number of possible states | 5 |
| name | Calcification Shape |
| node number | 20 |
| number of parent nodes | 1 |
| number of children nodes | 0 |
| joint vector size | 15 |
| children nodes | none |
| parent nodes | Calcification |
| clique | 15 |
| prior probability vector | calculated by software |
| conditional probability vector | FIG. 22 |

Node Calcification Number is created and defaulted as follows:

| | |
|---|---|
| number of possible states | 7 |
| name | Calcification Number |
| node number | 21 |
| number of parent nodes | 1 |
| number of children nodes | 0 |
| joint vector size | 21 |
| children nodes | none |
| parent nodes | Calcification |
| clique | 16 |
| prior probability vector | calculated by software |
| conditional probability vector | FIG. 23 |

Node Calcification Cluster shape is created and defaulted as follows:

| | |
|---|---|
| number of possible states | 5 |
| name | Calcification Cluster Shape |
| node number | 22 |
| number of parent nodes | 1 |
| number of children nodes | 0 |
| joint vector size | 15 |
| children nodes | none |
| parent nodes | Calcification |
| clique | 17 |
| prior probability vector | calculated by software |
| conditional probability vector | FIG. 24 |

Node Calcification Density is created and defaulted as follows:

| | |
|---|---|
| number of possible states | 5 |
| name | Calcification Density |
| node number | 23 |
| number of parent nodes | 1 |
| number of children nodes | 0 |
| joint vector size | 15 |
| children nodes | none |
| parent nodes | Calcification |
| clique | 18 |
| prior probability vector | calculated by software |
| conditional probability vector | FIG. 25 |

Node Calcification Size is created and defaulted as follows:

| | |
|---|---|
| number of possible states | 6 |
| name | Calcification Size |
| node number | 24 |
| number of parent nodes | 1 |
| number of children nodes | 0 |
| joint vector size | 18 |
| children nodes | none |
| parent nodes | Calcification |
| clique | 19 |
| prior probability vector | calculated by software |
| conditional probability vector | FIG. 26 |

Node Calcification Arrangement is created and defaulted as follows:

| | |
|---|---|
| number of possible states | 5 |
| name | Calcification Arrangement |
| node number | 25 |
| number of parent nodes | 1 |
| number of children nodes | 0 |
| joint vector size | 15 |
| children nodes | none |
| parent nodes | Calcification |
| clique | 20 |
| prior probability vector | calculated by software |
| conditional probability vector | FIG. 27 |

Cliques Creation

The network, which is a graph of nodes, is converted into a tree of cliques. The 21 cliques of the network correspond to the nodes that comprise the conditional vectors. All cliques are initialized with the following default information:

number of node members in the clique clique number for identification root clique indicator number of links to other cliques list of links to other cliques number of common nodes—nodes that a clique has in common with other cliques member nodes referenced by node number
common nodes referenced by node number
base node Clique 0 is created and defaulted as follows:

| | |
|---|---|
| number of node members | 5 |
| clique number | 0 |
| root clique Boolean | true |
| number of links to cliques | 2 |
| links | null, clique 11 |
| number of common nodes | 1 |
| member nodes | Breast Cancer, Age, Menarche, Birth, Relatives |
| common nodes | Breast Cancer |
| base node | Breast Cancer |

Clique 1 is created and defaulted as follows:

| | |
|---|---|
| number of node members | 2 |
| clique number | 1 |
| root clique Boolean | false |
| number of links to cliques | 12 |
| links | cliques 0, 2, 3, 4, 5, 6, 7, 8, 9, 10, 11, 12 |
| number of common nodes | 2 |
| member nodes | Mass, Breast Cancer |
| common nodes | Breast Cancer, Mass |
| base node | Mass |

Clique 2 is created and defaulted as follows:

| | |
|---|---|
| number of node members | 2 |
| clique number | 2 |
| root clique Boolean | false |
| number of links to cliques | 7 |
| links | cliques 1, 13, 14, 15, 16, 17, 18 |
| number of common nodes | 2 |
| member nodes | Calcification, Breast Cancer |
| common nodes | Breast Cancer, Calcification |
| base node | Calcification |

Clique 3 is created and defaulted as follows:

| | |
|---|---|
| number of node members | 2 |
| clique number | 3 |
| root clique Boolean | false |
| number of links to cliques | 2 |
| links | clique 1, null |
| number of common nodes | 1 |
| member nodes | Asymmetry, Breast Cancer |
| common nodes | Breast Cancer |
| base node | Asymmetry |

Clique 4 is created and defaulted as follows:

| | |
|---|---|
| number of node members | 2 |
| clique number | 4 |
| root clique Boolean | false |
| number of links to cliques | 2 |
| links | clique 1, null |
| number of common nodes | 1 |
| member nodes | Developing Density, Breast Cancer |
| common nodes | Breast Cancer |
| base node | Developing Density |

Clique 5 is created and defaulted as follows:

| | |
|---|---|
| number of node members | 2 |
| clique number | 5 |
| root clique Boolean | false |
| number of links to cliques | 2 |
| links | clique 1, null |
| number of common nodes | 1 |
| member nodes | Dilated Duct, Breast Cancer |
| common nodes | Breast Cancer |
| base node | Dilated Duct |

Clique 6 is created and defaulted as follows:

| | |
|---|---|
| number of node members | 2 |
| clique number | 6 |
| root clique Boolean | false |
| number of links to cliques | 2 |
| links | clique 1, null |
| number of common nodes | 1 |
| member nodes | Pain, Breast Cancer |
| common nodes | Breast Cancer |
| base node | Pain |

Clique 7 is created and defaulted as follows:

| | |
|---|---|
| number of node members | 2 |
| clique number | 7 |
| root clique Boolean | false |
| number of links to cliques | 2 |
| links | clique 1, null |
| number of common nodes | 1 |
| member nodes | Nipple Discharge, Breast Cancer |
| common nodes | Breast Cancer |
| base node | Nipple Discharge |

Clique 8 is created and defaulted as follows:

| | |
|---|---|
| number of node members | 3 |
| clique number | 8 |
| root clique Boolean | false |
| number of links to cliques | 2 |
| links | clique 1, null |
| number of common nodes | 1 |
| member nodes | Architectural Distortion, Breast Cancer, Previous Biopsy |
| common nodes | Breast Cancer |
| base node | Architectural Distortion |

Clique 9 is created and defaulted as follows:

| | |
|---|---|
| number of node members | 2 |
| clique number | 9 |
| root clique Boolean | false |
| number of links to cliques | 2 |
| links | clique 1, null |
| number of common nodes | 1 |
| member nodes | Tumor Location, Mass |
| common nodes | Mass |
| base node | Tumor Location |

Clique 10 is created and defaulted as follows:

| | |
|---|---|
| number of node members | 2 |
| clique number | 10 |
| root clique Boolean | false |
| number of links to cliques | 2 |
| links | clique 1, null |
| number of common nodes | 1 |
| member nodes | Mass Margin, Mass |
| common nodes | Mass |
| base node | Mass Margin |

Clique 11 is created and defaulted as follows:

| | |
|---|---|
| number of node members | 2 |
| clique number | 11 |
| root clique Boolean | false |
| number of links to cliques | 2 |
| links | clique 1, null |
| number of common nodes | 1 |
| member nodes | Mass Density, Mass |
| common nodes | Mass |
| base node | Mass Density |

Clique 12 is created and defaulted as follows:

| | |
|---|---|
| number of node members | 2 |
| clique number | 12 |
| root clique Boolean | false |
| number of links to cliques | 2 |
| links | clique 1, null |
| number of common nodes | 1 |
| member nodes | Halo Sign, Mass |
| common nodes | Mass |
| base node | Halo Sign |

Clique 13 is created and defaulted as follows:

| | |
|---|---|
| number of node members | 2 |
| clique number | 13 |
| root clique Boolean | false |
| number of links to cliques | 2 |
| links | clique 1, null |
| number of common nodes | 1 |
| member nodes | Mass Size, Mass |
| common nodes | Mass |
| base node | Mass Size |

Clique 14 is created and defaulted as follows:

| | |
|---|---|
| number of node members | 2 |
| clique number | 14 |
| root clique Boolean | false |
| number of links to cliques | 2 |
| links | clique 1, null |
| number of common nodes | 1 |
| member nodes | Palpable Mass, Mass |
| common nodes | Mass |
| base node | Palpable Mass |

Clique 15 is created and defaulted as follows:

| | |
|---|---|
| number of node members | 2 |
| clique number | 15 |
| root clique Boolean | false |
| number of links to cliques | 2 |
| links | clique 2, null |
| number of common nodes | 1 |
| member nodes | Calcification Shape, Calcification |
| common nodes | Calcification |
| base node | Calcification Shape |

Clique 16 is created and defaulted as follows:

| | |
|---|---|
| number of node members | 2 |
| clique number | 16 |
| root clique Boolean | false |
| number of links to cliques | 2 |
| links | clique 2, null |
| number of common nodes | 1 |
| member nodes | Calcification Number, Calcification |
| common nodes | Calcification |
| base node | Calcification Number |

Clique 17 is created and defaulted as follows:

| | |
|---|---|
| number of node members | 2 |
| clique number | 17 |
| root clique Boolean | false |
| number of links to cliques | 2 |
| links | clique 2, null |
| number of common nodes | 1 |
| member nodes | Calcification Cluster Shape, Calcification |
| common nodes | Calcification |
| base node | Calcification Cluster Shape |

Clique 18 is created and defaulted as follows:

| | |
|---|---|
| number of node members | 2 |
| clique number | 18 |
| root clique Boolean | false |
| number of links to cliques | 2 |
| links | clique 2, null |
| number of common nodes | 1 |
| member nodes | Calcification Density, Calcification |
| common nodes | Calcification |
| base node | Calcification Density |

Clique 19 is created and defaulted as follows:

| | |
|---|---|
| number of node members | 2 |
| clique number | 19 |
| root clique Boolean | false |
| number of links to cliques | 2 |
| links | clique 2, null |
| number of common nodes | 1 |
| member nodes | Calcification Size, Calcification |
| common nodes | Calcification |
| base node | Calcification Size |

Clique 20 is created and defaulted as follows:

| number of node members | 2 |
|---|---|
| clique number | 20 |
| root clique Boolean | false |
| number of links to cliques | 2 |
| links | clique 2, null |
| number of common nodes | 1 |
| member nodes | Calcification Arrangement, Calcification |
| common nodes | Calcification |
| base node | Calcification Arrangement |

Bayesian Network Initialization

The Bayesian network, BC_Diagnosis, is the structure that embodies the dependencies of the member domain nodes. The Bayesian network structure is created and defaulted with the following information:

| textual name | BC_Diagnosis |
|---|---|
| number of nodes | 26 |
| number of cliques | 21 |
| hypothesis node | Breast Cancer |
| nodes | nodes 0 through 25 |
| cliques | cliques 0 through 20 |

Joint Probability Vector Initialization

Each clique has a base node that has a joint probability and a conditional probability vector. The joint probability vectors are initialized at system startup. Each node has a prior probability vector. At system startup, the initialized joint vectors are used to calculate the initial prior probability vectors for all nodes. The initial prior probability vectors represent the state of the Bayesian network with no evidence applied.

Calculation of the initial joint vectors is started at the clique marked as the root clique. The remaining cliques are calculated by traversing the clique tree in order of the clique links. At each clique, the joint vector is initialized by vector multiplication of the conditional vector and the prior probability vectors of the conditioning nodes. For the network comprised of n cliques:

for any clique $C_i$, i=0 . . . n−1
    where $C_i$ is comprised of member nodes $X_j$, j=0 . . . m−1,
    $X_0$ is the base node,
    $X_1$ . . . $X_{m-1}$ are the conditioning nodes, for all cliques initialize joint vector for $C_i$:

$p(x_0, x_1, \ldots x_{m-1}) = p(x_i|x_1, \ldots x_{m-1}) \cdot p(x_1) \cdots \cdot p(x_{m-1})$ mark $C_i$ as updated
      if $C_i$ (link) is not NULL,
      if $C_i$ is not marked as updated, continue
  end_for Prior Probability Vector Initialization Each node has a prior probability vector. An initial prior probability vector is calculated during the joint vector initialization calculations as described above. For each node, its initial prior probability vectors is calculated and stored. Each clique's joint vector is used to calculate its (the clique's) member nodes' prior probability vectors.

for any clique $C_i$, i=0 . . . n−1
    where $C_i$ is comprised of member nodes $X_j$, j=0 . . . m−1,
    $X_0$ is the base node,
    $X_1$ . . . $X_{m-1}$ are the conditioning nodes,
    $X_i$ has possible states 0 . . . p−1,
    with joint vector, $p(x_0, x1, \ldots x_{m-1})$ for all nodes in $C_i$, calculate the prior probability vector for node $X_j$ $$P(X_j) = \sum_{j=0}^{p} (P(X_0, \ldots, X_{m-1})X_0, \ldots, X_{j-1}, X_{j+1}, \ldots X_{m-1}$$

end_for

Evidence Vector Initialization

The network creates an evidence vector at system initialization. The fields of this evidence vector are shown in FIG. 31. This vector contains an entry for each node in the network. Its entries are initialized to default values, indicating no evidence has been received by the system:

for any Evidence_Vector of size n,
    where n is the number of nodes in the network
    for all elements $E_i$, i=0, . . . ,n−1
    Set $E_i$ to Default_Value
  end_for Upon receipt of evidence, this vector is modified to contain, for any node that received evidence, the state that is certain. The entry of evidence is discussed further below.

II

Evidence Entry and Propagation

Evidence is entered into the network by indicating that a node of the network is in a known state. User-entered evidence can be applied to nodes age in years, age of menarche, age of first life birth, number of first order relatives with breast cancer, previous biopsy at site, breast pain, nipple discharge, palpable mass, architectural distortion, asymmetry in breast, developing density in breast, dilated duct in breast, mass margin, mass density, mass size, halo sign, tumor location by quadrant, calcification cluster shape, calcification number, calcification shape, calcification density, calcification arrangement, and calcification size. As previously stated, nodes breast cancer, mass, and calcification do not accept user evidence.

Evidence Entry

User-observed evidence is input into the inference system by way of an encoded evidence vector containing evidence findings for each particular patient. In the preferred embodiment, these evidence findings are entered into the system through a graphical user interface (GUI). Sample data entry windows of this GUI are presented in FIGS. 32–37. The user selects the specified evidence through the menus of the GUI.

The system is capable of acquiring evidence in single-patient mode or multiple-patient mode. In single-patient mode, evidence is entered for one patient. The system processes this single case when notified by the user that the evidence entry is complete. The single-patient mode is the system default mode. If the user selects multiple-patient mode, evidence is entered for multiple patient during a single session. The system creates a batch file of evidence vectors—creating separate evidence vectors for each patient case—and when notified by the user, processes all the evidence vectors sequentially. In both modes, the system generates separate patient result files.

For single-patient mood, one evidence vector (Evidence_Vector[k]) is created and initialized. For multiple-patient mood, an evidence vector is created for each patient case.

for any element $E_i$ of the Evidence_Vector[k],
    where i=0, . . . , n−1, element $E_i$ has m possible states, and k=1 , . . . , p−1 set $E_i$ of Evidence_Vector[k] to Evidence_Value(j), where j=0, . . . , m−1

Each evidence vector consists of separated data units or fields. The position of each field corresponds to a numbered node in the network. FIG. 31 presents the format of the evidence vector fields and their relationships to the nodes of the network. The value of each field is an encoding of a possible node state (except for the fields corresponding to the nodes that are incapable of taking on evidence, i.e., nodes 4, 5, and 6, corresponding to breast cancer, mass, and calcification, respectively). The record is preloaded to default values for each field, and user-entered evidence can replace these default values with actual findings. The encoding scheme of each field assigns an integer, starting with zero and incrementing sequentially, to each state of a node. For example, the node "age in years" has twelve possible states, which represent twelve categories of ages. The integer zero is assigned to the default value for this node, 1 is assigned to state 20–24, 2 to state 25–29, and so on.

Each evidence vector is verified to be correct. The vector is checked for correct number of fields and field values within range of the corresponding node. An error message is generated and processing of this vector halts, if the syntax of the vector is invalid. The error message indicates what the error condition is—an invalid state for a particular node or a missing node field. Upon successful validation of an evidence vector, the vector is used to drive the evidence propagation through the network.

Evidence Vector Propagation

When the user notifies the system that evidence acquisition is complete, the system performs the evidence propagation or belief updating of the network in response to that evidence. The user-observed evidence is extracted from the validated evidence vector and used to update the joint and prior probability vectors for each node in the network. A new hypothesis node, Breast Cancer, prior probability vector is also calculated.

The processing order of the evidence is constrained by the evidence vector fields ordering. For example, if the only evidence observed by the user is age (corresponding to field 0) and mass margin (corresponding to field 15), age evidence is processed first and mass margin evidence second. Evidence that is not user-observed contains default values in the evidence vector and will not be processed by the propagation logic. Fields containing user-observed evidence are processed in sequential order, and are in turn propagated through the network. All prior unconditional probability distributions are updated based on the user-observed evidence in the evidence vector.

During an evidence propagation session, the system scans an evidence vector (Evidence_Vector[k]) for all user-entered evidence and processes a single user-entered evidence value at a time. As long as there is another unprocessed node state in the evidence vector, the current node state is extracted and used to create a new prior probability for that node. Because the extracted evidence vector value for the node is the user-observed evidence, the prior unconditional distribution for this node must be updated. The state in the probability distribution which corresponds to the user-observed value is set to one indicating certainty, and the remaining states set to zero indicating an impossible state.

The updated probability distribution is then used to update the joint vectors it is a member of by use of Bayes inversion formula [3]. After the joint vector is updated by the evidence, each member node has its prior unconditional distribution recalculated to reflect the impact of the evidence on it. This is done by summing out the distribution using formula [2]. The new prior unconditional distributions of the members of the joint vector are in turn used to update joint vectors they are neighbors of. Updating of joint vectors and recalculations of prior unconditional distributions of members of updated joint vectors continues until each node in the network is updated exactly one time.

The propagation path is facilitated by storing the network graph in an intermediate structure, which is a tree in which the nodes of the tree represent the joint distributions of the network and the links encode the information concerning which joint distributions are related by common variables. The propagation path is a tree traversal, starting at the node that contains the observed evidence member, and visiting each node exactly one time. The tree traversal walks the tree by checking if a neighbor node has been updated. If not, the neighbor node is updated—Bayes inversion formula [3]—and prior unconditional distributions are calculated—summing over partitions [2]. The new distributions are used in turn to update their neighbors until each node in the tree has been updated. The only node we are interested in is the hypothesis node, Breast Cancer. The prior unconditional probability distribution is extracted from the joint vector in which Breast Cancer is a member.

Once a piece of evidence that the user entered has been propagated through the network, the posterior probability distribution for the hypothesis node, Breast Cancer, is calculated. This is done by computing the prior probability unconditional distribution for breast cancer from its joint distribution and summing over all the combinations of the conditioned variables. The newly calculated posterior distribution is stored as a tuple containing additionally the previous posterior probability and the associated piece of evidence: new posterior probability, old posterior probability, and evidence. As each piece of observed evidence is processed by the system, a tuple is added to create a trace of evidence impact on the hypothesis node. The node that received the evidence is also saved.

For each evidence vector, the system loops through each element ($E_i$) of the vector, checking if the user has entered evidence for the corresponding node. If an element is the default value, the system checks the next element. When an element is detected as having received user-entered evidence, the system initiates the network update process. The network update process traverses the clique tree, starting at the clique ($C_i$) whose member received the user-entered evidence, and continues in order of that clique's clique link list. Upon completing the network updating for a single user-entered evidence value, the system stores the previous and current value of the hypothesis node, Breast Cancer. The network updating continues until all elements of the evidence vector are processed.

for an Evidence_Vector[k]
        for each element $E_i$ of the Evidence Vector[k]
            if element $E_i$ is a valid state for the associated node
                set the node's probability evidence vector to contain the value 1 for the certain state, and values 0 for the other states

```
            mark the node as receiving evidence
            call routine BNReceiveEvidence( ) to update the
               network
            store the unmodified and modified prior probabil-
               ity vector of the hypothesis node
            call BNExplainReasoning( ) to generate and store
               the affect element E_i has on the evidence node
            for all nodes, except the nodes that are marked as
               receiving evidence, clear update flags
            end_for
         increment evidence count for clique evidence node is
            a member of
      end_for
   end_for
Process Initial Clique (BNReceivedEvidence( ))
   As the system scans an evidence vector for an element
that has received user-entered evidence, the network updat-
ing begins at the clique of a node that received user-entered
evidence. The node is marked as receiving evidence, and the
node's current prior probability vector is set to the evidence
vector. The evidence vector, which represents any node's n
possible states, contains 0 for the states that are impossible
and a 1 for the state that the user has selected as known.
   for the node marked as receiving evidence
      determine its clique C_i
      mark clique C_i as receiving evidence
      store node number at clique C_i
      set the node's current prior probability to the evidence
         vector
      call BNVisitClique( ) to begin evidence propagation
         from C_i
   end_for
Traverse the Clique Tree (BNVisitClique( ))
   A user-entered evidence value is propagated through the
network, starting at the clique of the node that received the
evidence, and traversing the clique tree in order of the link
lists of each clique, C_i.
   for all cliques C_i
      if a clique C_i is valid
         call BNProcessClique( ) to process all nodes in the
            clique C_i
         mark clique C_i as updated
         if left link of clique C_i is valid
            if left-linked clique C_i is not marked as updated
               call BNVisitClique( ) to traverse those links
         for all valid clique C_i right links
            if right-linked clique C_i is not marked updated
               call BNVisitClique( ) to transverse those links
         end_for
   end_for
Prepare Clique for Updating (BNProcessClique( ))
   During the network update process, a clique C_i's joint
vector is updated by the evidence. Once a joint vector has
been updated, all its member nodes—except those that have
received user-entered evidence—have their prior probability
vectors updated.
   for each clique C_i
      get base node of clique C_i
      get number of common nodes of clique C_i
      get common nodes of clique C_i
      get number of nodes in clique C_i
      propagate evidence starting at clique C_i
      call BNPropagateEvidence(C_i)
   end_for
Update a Clique (BNPropagateEvidence( ))
   A clique C_i is marked as receiving evidence, if one of its
member nodes is the node that received user-entered evi-
dence during this propagation session. Clique C_i's joint
vector is updated. If clique C_i is marked as receiving
evidence, the node that received evidence is used to calcu-
late the new joint vector. This node's evidence vector is
multiplied by the clique's joint vector. This product is
divided by the node's previous prior probability vector. If
clique C_i is not marked as receiving evidence, its joint vector
is updated by multiplying it by the clique C_i's common
node. This product is divided by the common node's pre-
vious prior probability vector. The new joint vector is stored
at clique C_i. All node members of clique C_i, except nodes
that have been marked updated, have new current prior
probabilities calculated. This is done through a call to
routine BNCalcPriorProbs( ) passing the node number and
the clique number. When all nodes in clique C_i are marked
as updated, clique C_i is marked as updated.
      if all nodes in clique C_i are marked as receiving user
         evidence, return
      if this clique C_i is marked as receiving user evidence,
         retrieve node that received evidence
         calculate new joint vector for clique C_i
         for any clique C_i, i=0 . . . n−1
            where C_i is comprised of member nodes X_j, j=0 . . .
               m−1,
            X_j has possible states 0 . . . p−1, with joint vector, p
               x_0, x_1, . . . x_{m−1})
            $p_{new}(x_0, x_1, \ldots x_{m-1}) = (p(x_0, x_1, \ldots x_{m-1}) \cdot p(node=evidence)/p(node))$
            where p(node) denotes the prior probability vector
               of node,
            where p(node=evidence) denotes the evidence
               vector of node
      else
         retrieve common node[i]
         calculate new joint vector for clique C_i
            for any clique C_i, i=0 . . . n−1
               $p_{new}(x_0, x_1, \ldots x_{m-1}) = (p(x_0, x_1, \ldots x_{m-}) \cdot p(node=common[i])/p(node))$
               where p(node) denotes the prior probability vec-
                  tor of node, where p(node=common[i])
                  denotes the evidence vector of node
      for all nodes that are not marked as receiving evidence
         set current prior probability vectors,
         BNCalcPriorProbs( )
      end_for
      mark clique as updated
Update Prior Probability Vectors (BNCaclPriorProbs( ))
   During the network update process, after a clique C_i's
joint vector is recalculated to account for the user-entered
evidence, clique C_i's member nodes have their prior prob-
ability vectors updated. Each member node has its previous
prior probability vector set to its current prior probability
vector. Each member node then has its current prior prob-
ability vector recalculated.
   for a node N_i, in clique C_i,
      if node is marked as receiving user evidence, return
      if node is marked as updated, return
      get number of node members in clique C_i
      get node N_i's clique index
      get base node of clique C_i
      get joint vector of clique C_i
      set node N_i's previous prior probability vector to node
         N_i's current prior probability vector
      calculate new prior probability vector for node N_i in
         clique C_i
```

$$P(\overset{p}{X_j}) = \sum_{j=0} (P(X_0, \ldots, X_{m-1})X_0, \ldots, X_{j-1}, X_{j+1}, \ldots X_{m-1}$$

set node $N_i$'s current prior probability vector to node $N_i$'s newly calculated prior probability vector normalize node $N_i$'s current prior probabilities mark node $N_i$ updated end_for Explain Reasoning (BNExplainReasoning( ))

After all evidence for a specific record has been propagated through the network and the posterior distribution of breast cancer, given all the instantiated evidence, has been calculated, the system constructs an explanatory report. This textual report describes the evidence input, the impact of each piece of evidence on the posterior distribution of breast cancer given current evidence, and the final calculated probability of breast cancer on a case or evidence vector basis. This is a tracking of how each piece of evidence impacted the hypothesis node, Breast Cancer, and provides the user with a trace of the system reasoning.

The logic in this section uses the set of tuples generated during evidence propagation each time the hypothesis node, Breast Cancer, was updated. A numeric comparison is done on each tuple, comparing the old and new posterior probabilities. The delta or difference in the value is used to generate text indicating a percentage change (increase, decrease, or no change) in the new posterior probability given a piece of evidence. A description is generated, including the values of the previous and current prior probability vectors, the node that received evidence, and the evidence state the user entered. After all evidence is propagated, the cumulative affect of the total evidence is calculated, and a description is generated. The results are formatted into a textual report, which, in addition to the textual explanations, also contains time stamping and case identification information. The report is archived electronically and is available for hard copy printout. A typical output file contains the following information:

Breast Cancer Diagnosis

Patient: Jane Doe

Date: Dec. 10, 1997

File Number: nnn

Doctor/Clinic: Marcus Welby, M.D.

Evidence entered for patient Jane Doe is:

Patient History
  Age: 45
  Age menstruation started: 13
  No children
  No relatives with a history of breast cancer
Physical Findings:
  none
Mammographic Findings:
  Indirect Findings:
    Developing Density: present
  Direct Findings:
    Mass: present
    Mass Characteristics Noted:
Tumor Location: upper outer quadrant
    Mass Margin: spiculated margin
    Halo Sign: absent
    Calcifications: absent Breast Cancer Diagnosis Results:

Initial likelihood of breast cancer is nn out of nnn.

Evidence "Age=45" increases the likelihood to n.

Evidence "Age Menstruation Started=13" increases the likelihood from n to m.

Evidence "No Children" increases the likelihood from m to p.

Evidence "No Relatives with a History of Breast Cancer" decreases the likelihood from p to a.

Evidence "Developing Density Present" increases the likelihood from a to b.

Evidence "Mass located in the upper outer quadrant" does not affect the likelihood.

Evidence "Mass Margin=Spiculated" increases likelihood from b to i.

Evidence "Halo Sign Absent" increases likelihood from i to x.

The cumulative affect of all evidence entered for patient Jane Doe increases an initial likelihood nn to x, a factor of y.

Re-initialize the Network (BNReInitNetwork( ))

After an evidence vector has been scanned and the associated network updating is completed, another evidence vector may be propagated, but the network must first return to its initial configuration. The system has stored the initial joint vectors and prior unconditional vectors calculated during system startup initialization. These vectors are used to put the system in the initial configuration necessary.

The system puts itself into a re-initialized state. All joint probability and prior probability vectors are recalculated to an initial state, i.e., the conditional vectors are used to recalculate the joint vectors, and from the joint vectors the initial prior probability vectors are calculated. The previous prior probability vectors are set to the initial (current) prior probability vector. All flags that track evidence, node updating, and clique updating are reset to their default states, indicating the system has not received any user-entered evidence.

for all nodes $N_i$,
  reset $N_i$'s previous prior probability vector
  reset $N_i$'s current prior probability vector
for all nodes N 's no parent nodes,
  reset node $N_i$'s current prior probability vector to initial values
for all nodes $N_i$,
  recalculate current prior probability vectors:
  unmark any nodes $N_i$ marked for receiving evidence flags,
  unmark any nodes $N_i$ marked updated
  unmark any cliques $C_i$ marked updated
  set root clique to Clique 0
  recalculate joint and prior probability vectors for all nodes $N_i$, BNInitNetwork( )
for all nodes $N_i$,
  set nodes $N_i$'s current prior probability vectors to calculated values
  set nodes $N_i$'s previous prior probability vectors to current prior probability vectors
  reset node flags, received_evidence and updated flag via a call to,
  unmark any nodes $N_i$ marked for receiving evidence flags,
  unmark any nodes $N_i$ marked updated
  unmark any cliques $C_i$ marked updated Initialize the Network (BNInitNetwork( ))

Certain system initialization tasks are done at system startup and when a new patient case is to be calculated. All cliques $C_i$ are traversed, starting at the root clique, and each clique $C_i$ has its joint and prior probability vectors re-initialized.

for all cliques $C_i$,
      if clique $C_i$ is invalid, return
      calculate clique $C_i$'s joint vector, BNCalcJointProbs( )
      for each member node $N_i$ in clique $C_i$, calculate prior probability vector, BNCalcPriorProbs( )
      mark clique updated
      if clique $C_i$ previous link is valid
      if clique $C_i$ is not marked updated, re-initialize clique, BNInitNetwork( )
      if clique $C_i$ next link of clique is valid,
         if clique $C_i$ is not marked updated, re-initialize clique, BNInitNetwork( )

Calculate Joint Probability Vectors (BNCalcJointProbs( ))

Initial joint probability vectors are calculated at initial system startup and when a new patient case is to be propagated through the network. The calculation is done at each clique, $C_i$, starting at the clique marked as the root clique (Clique 0). The clique tree is traversed based on the ordering of the clique links at each clique $C_i$. At each clique $C_i$, the conditional vector is multiplied by the product of the non-base nodes of the clique.

for a clique $C_i$ of nodes $X_0, \ldots, X_{m-1}$,
      calculate joint vector $p(x_0, x_1, \ldots x_{m-1})$
      $p(x_0, x_1, \ldots x_{m-1}) = p(x_0|x_1, \ldots, x_{m-1}) \cdot p(x_1) \ldots (p(x_{m-1}))$ The system would then be ready to process another evidence vector.

III

Interactive Multimodal Explanation Generator

In the preferred embodiment of the diagnostic support tool of the present invention, the inference system used is a Bayesian network. As mentioned above, a shortcoming of Bayesian networks in automated medical reasoning is the difficulty users have understanding and trusting the systems. To make the diagnostic support tool useful to a wide audience of users, an interactive multimodal explanation generator is desirable.

An explanation generator must explain the numeric relations that comprise the probabilistic model and explain the probabilities that are derived from the model. Hence, in order to provide an effective explanation, an explanation generator must relate its numerical information to the world knowledge it underlies. Explanation of probabilistic data presents unique problems for explanation generation. Although Bayesian Networks provide good models for representing uncertainty, the reasoning they support differs significantly from how people think about uncertainty. Users have different information needs. Users interested in the model structure will be concerned with How the system justifies its answers. Users interested in how the model relates its conclusions to their own view of the problem will be concerned with Why the system answered as it did. Graphical depictions of quantitative data help people understand relative magnitudes, but graphical depictions of other relationships between abstract concepts is problematic.

Explanation generation in the system is an interactive, multimodal process that helps users understand the decision system without expertise in Bayesian network technology. The explanation process supports an ongoing dialog between the system participants. Users are able to select and summarize important probabilistic relationships. The system incrementally produces multimodal explanations that use natural language, text, graphics, and animation in an ongoing dialog adapting the interaction to the users' needs and concerns.

Users express themselves through direct manipulation and natural language description. The system responds to the users by presenting synchronized graphical and verbal replies that clarify and reinforce its answers. Users concerned with the underlying structure of the model can view a graphical depiction of the model's overall topology enhanced with a natural language summary of important results. Users can interact with the system by selecting a node for further description. Users interested in how the results of the system relate to their concerns can interact with the systems by asking questions or making statements. The system engages the users in a dialog that is sensitive to their needs.

Figure 39:
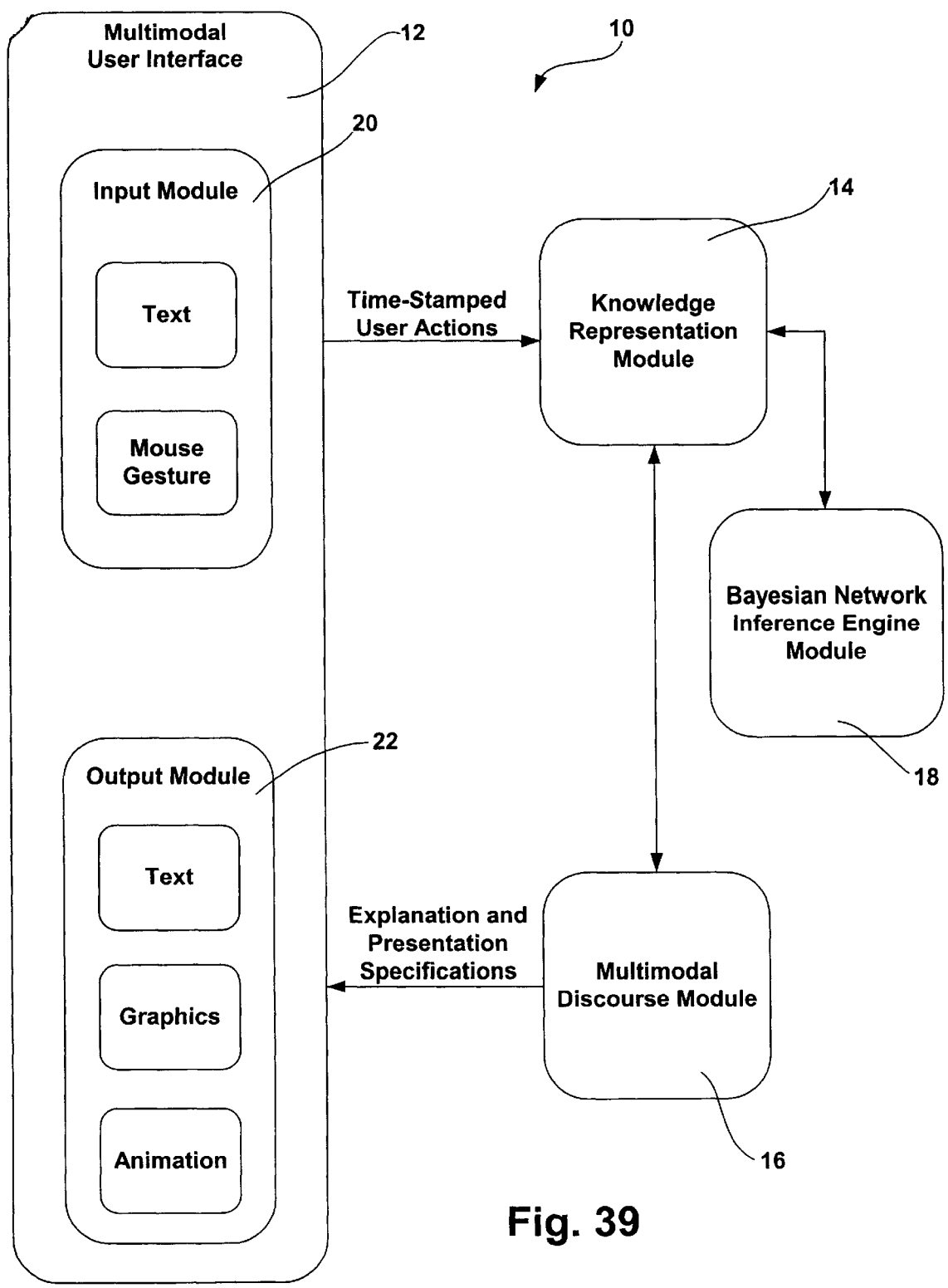
FIG. 39 is a block diagram of a preferred embodiment of the computer-aided diagnostic support tool of the present invention.

As shown in FIG. 39, the computer-aided diagnostic support system 10 thus preferably comprises four major components: a multimodal interactive user interface 12, the knowledge representation module 14, the multimodal discourse module 16, and the Bayesian inference engine module 18. The multimodal user interface 12 itself comprises distinct input and output modules 20, 22, respectively. The system is designed to help users without expertise in Bayesian network technology understand a complex decision system by providing explanations that use natural language, graphics, and animation as an interactive, ongoing dialog.

Input Module

The multimodal user interface 12 provides input services though the input module 20. The input module 20 synthesizes individual user actions of keyboarded text and mouse gestures into a single sequenced stream of events for the knowledge representation module 14. For example, the system and a user, Mrs. Smith, might conduct a dialog using multiple modalities in which Mrs. Smith inquires of the system what her risk of developing breast cancer might be. A sample dialog may proceed as follows:

1. System: TYPED: Welcome. Please enter your medical record identification number.
2. Mrs. Smith: TYPED: 1234
3. System: TYPED: What can I help you with?
4. Mrs. Smith: TYPED: I am concerned about my risk of developing breast cancer.
5. System: TYPED: Yes, examining your medical history I can understand why you are concerned.
6. System: GRAPHICS: Display a bar chart of all the risk factors, ordered in relative importance of each factor.
7. System: TYPED: Here is a chart of the risk factors that might affect your chance of developing breast cancer. Let us look at which factors are affecting you.
8. System: GRAPHICS: Display a bar chart of all risk factors, indicating each factor's affect on Mrs. Smith's risk of developing breast cancer.
9. System: TYPED: Although you can not modify these risk factors, I have some information that may help you. Would you like to continue?
10. Mrs. Smith: TYPED: Yes, what should I know?
11. System: TYPED: These risk factors are of particular interest to you.
12. System: GRAPHICS: Display of relevant risk factors, Age and Family History of Breast Cancer as clickable boxes.

13. System: TYPED: Which risk factor would you like to examine?

14. Mrs. Smith: MOUSE: Left clicks on Age box on screen.

15. System: TYPED: Your medical history indicates you are 52 years old.

The incidence of breast cancer increases with age. The AMA recommends you perform monthly breast exams and undergo a yearly mammogram. Would you like instructions on monthly breast exams?

16. Mrs. Smith: TYPED: Yes

In the above sample dialog, the modality used is specified as TYPED for text, GRAPHICS for a graphics rendering, and MOUSE for a mouse gesture. In this dialog, the input module 20 constructs an input object for each utterance of the user Mrs. Smith, identifying the modality, the sequence, and the content . Each input object is inserted into the input stream that is sent to the knowledge representation module 14 for parsing and encoding into knowledge representation structures as discussed further below.

Knowledge Representation Module

The knowledge representation module 14 facilitates multimodal interaction by supporting the communicative acts and objects from a range of modalities including natural language, text, mouse gestures, and graphical presentation objects. It receives a stream of multimodal input objects from the input module 12, and parses and encodes these objects into representations of the user's actions. These representations support discourse processing as items comprising the discourse history. In addition, the knowledge representation module 14 serves as an interface between the multimodal discurse module 16 and the back-end of the Bayesian network inference engine 18. Probabilistic data from the Bayesian network is use d in the multimodal explanation generation of this system.

The knowledge representation module 14 is implemented as a semantic network structure in which information about natural language utterances, multimodal events and actions, discourse entities, and nodes from the Bayesian network is encoded. The entire system has access to this uniform knowledge construct. This module 14 is composed of the domain-specific (breast cancer) lexicon and parser which parses and encodes natural language utterances from the user, the semantic network structure which encodes the meaning of the system, and the logic to process the flow of data and commands between the input module of the multimodal user interface, the multimodal discourse module and the Bayesian network inference engine module. The knowledge representation module 14 receives input data. It translates and encodes this data into an abstracted format (an "abstract statement" or "abstracted parse result" or "abstract concept") and passes it to the discourse module. The knowledge representation module processes inquires from the multimodal discourse module during a dialog session. It also interrogates the Bayesian network inference engine module during the dialog session, asking for probability calculations which it passes to the multimodal discourse module.

The following subsections detail the components (data repositories and logic) of the knowledge representation module.

Knowledge Representation Module—Natural Language Parser

The motivation for a natural language interface is that the processing capabilities add a dimension of flexibility and intelligence to the system. The primary operation of a natural language system is to encode the meaning of a sentence into a representation, and to use this representation in reasoning tasks. Natural language understanding is composed of three levels of representation. Syntactical processing is concerned with the structural or grammatical components of a sentence. Semantical processing computes a logical form that represents the meaning of the sentence. Contextual processing connects language to the application domain.

Natural language utterances entered by the user through the keyboard are parsed and encoded using a bottom-up partial parsing strategy. The parser outputs abstract conceptual statements that are inserted into an explicit discourse history structure. In turn, this discourse structure is used by the discourse module to mediate the on-going dialog between the system participants. The components of the "abstracted parse result" consist of statement type, statement origin, statement modality, and statement context.

The statement type classifies an utterance into categories describing the action of the system or the request of the user. FIG. 40 is a table providing a partial list of possible statement types and a description of each listed statement type.

The statement origin indicates the origin of the utterance. If the utterance originates from the user, the parser assigns the type USER_ORIGIN. Conversely, if the utterance originates from the system, the parser assigns the type SYSTEM_ORIGIN.

The statement modality indicates the modality that statement is issued in. FIG. 41 comprises a table indicating possible modality types.

The statement context assigns a contextual meaning to an utterance relating the utterance to the domain (breast cancer diagnosis). The parser uses the statement context to manage the discourse history. FIG. 42 is a table providing a partial list of possible statement contexts and their descriptions.

For example, the user may enter by keyboard, the utterance "I am concerned about my risk of breast cancer." This utterance is translated into the abstract statement: GENERAL_CONCERN_QUERY, USER_ORIGIN, TYPED_KEYBOARD, GENERAL_CONCERN. The system recognizes this as a question on general health from a "user" participant, with the utterance typed at the keyboard, and the concept is classified as a general concern about the risk of breast cancer. In contrast, the statement typed by the user, "I am worried about my risk of breast cancer as my mother had breast cancer" is translated into the abstract statement: SPECIFIC_CONCERN_QUERY, USER_ORIGIN, TYPED_KEYBOARD, FAMILY_HISTORY_CONTEXT. The statement is parsed and encoded as an abstraction that is a specific concern from the user, typed at the keyboard. The specific concern is about the user's risk of breast cancer with the knowledge of a family history.

The syntax of the input is analyzed using a partial parsing technique. Partial parsing exploits the fact that in limited domains, certain grammatical components can reliably be identified. These include noun phrases and verb phrases. In contrast, a full parser, in which each word is identified syntactically, is computationally expensive and impractical with respect to ambiguity resolution. The partial parser determines the semantic type of the noun and verb phrases it recognizes. In an input sentence, the noun phrase "worried about" is assigned a semantic type CONCERN_VERBS. The semantic typing serves to identify word types and to group related words. Words that are unrecognized or deemed irrelevant are ignored. As such, the parsing algorithm finds all noun phrases and verb phrases, filtering out unused words. The words that are retained are stored in a chart structure and assigned a semantic type. FIG. 43 comprises a partial table of possible semantic types and descriptions.

The next step of parsing analysis is pattern matching: matching the input words with a predefined pattern. The approach taken is to try and match a general pattern first. If this is unsuccessful, a specific pattern matching is undertaken. Unrecognized patterns prompt the system to ask for clarification. Finally, the system performs semantic processing, assigning a meaning representation to the matched pattern in terms of the abstract statement which is then inserted into the discourse history structure.

Components of the Natural Language Parser—Lexicon

The natural language parser is comprised of two principal components, the lexicon and the parser. The lexicon is a dictionary or collection of words related to our domain (breast cancer). The word entries are categorized by semantic type (verb, noun, adjective, etc.). The lexicon stores information on the number of total entries, and a list of entries. The list of entries consists of the text string representing a word entry, and its assigned semantic type. The lexicon is stored as a static text file. The format of the file is the text string followed by an encoded semantic type. Words that are not in the lexicon are deemed irrelevant—they are not used in constructing the abstracted parse result. These words would include words not related to the domain of breast cancer, and words such as "the", "a", or "these". Examples of words in the lexicon are carcinoma, cancer, dense, density, right, left, scattered, size, year, prior, cluster, calcification, subareolar, outer, round, innumerable, multiple, discrete, varying, ill-defined, arrangement, branching, borders, irregular, oval, margin, number, abnormal, unremarkable, and spiculated. Each word in the lexicon is assigned a semantic type (FIG. 43). Semantic types include verbs and verb phrases, noun and noun phrases, query phrases, affirmative and negation phrases, conjunction and disjunction (and, or), and noun and adjective phrases that correspond to the nodes and their states. The lexicon is a static structure that is constructed based on the network (nodes and their states), with words and their semantic types determined based on the breast cancer domain. The lexicon entries that are concerned with explaining the system (queries—why, how, if, what—, commands for explanation, expressions of concern, and so forth) are assigned a semantic type consistent with their most likely use in this type of conversation. If during a dialog, the semantic type proves incompatible, the system attempts to provide resolution by examining the history of the conversation.

Components of the Natural Language Parser—Chart Parser

A chart parser is a mechanism to analyze the grammatical structure of a sentence. The operation of a chart parser is to take a sequence of symbols identified in the input sentence and to match them to a pattern. The chart parser has access to the lexicon and bases its filtering of unnecessary phrases on it. The chart parser contains functions that perform the partial parsing and pattern matching activities required for a semantically driven schema. The routines perform partial parsing by recognizing words (noun phrases and verb phrases) that are members of the lexicon. Unrecognized words are ignored. Parsed words are stored in a chart data structure, containing the word itself and its semantic type (verb, noun, etc). The parseChart( ) routine traverses the chart attempting to match the stored words with the patterns of the grammar. The heuristic employed looks at the first word in the chart, and performs a high-level match for statement type though successive calls to routines processHowQuestion( ), processWhatQuestion( ), processWhyQuestion( ), processIfQuestion( ), processVerb( ), processAffirmative( ), processNegative( ), processGeneral( ), processWantVerb( ), processDemoVerb( ), processExplainVerb( ), and so forth. If a specific routine does not process a match, the next routine in order is called. After all routines are called and no match occurs, the system enters the unrecognized utterance state, and performs processing to attempt to find out what the user wants. The discourse history dialog structure is used to determine the context of the conversation, and the system attempts to ask the user questions based on this knowledge. If there is a match, the utterance is transformed into the abstracted parse result, and inserted into the discourse history structure.

Components of the Natural Language Parser—Chart Parser Natural Language Algorithm The algorithm implemented in the natural language user interface is a partial parsing of user-input noun and verb phrases. Recognized phrases are stored in a chart data structure, consisting of the text string and the semantic type. Pattern matching is applied to the chart according to a heuristic of attempting to match the first stored chart entry with a high-level statement type. Successful matches cause an abstract concept statement to be created and inserted into the discourse dialog history structure. The following is the PDL (Programming Design Language) of the type of parsing the system provides.

PDL for Natural Language Partial Chart-Parser
1. Initialize Parser
   Create Lexicon Structure
     open lexicon file
     if lexicon file does not exist
       return ERROR
     else
       for all words in lexicon file
         read word from file
         insert word into lexicon structure
         read word type from file
         insert word type into lexicon structure
2. Wait for input utterance
3. Parse Input utterance (typed keyboard information)
   Create chart structure for current utterance
   Determine number of words in input utterance
   If number of words at least 1
     loop through buffer
     for each word, search for word in lexicon
       if word in lexicon
         create chart entry
         store word in chart entry
         store semantic type in chart entry
         add chart entry to chart
       else if not found
         discard word
4. If chart is not NULL
   parse chart entries
     retrieve number of entries in chart
     if number of entries=0
       create abstract concept:
       CMD_UNKNOWN,TYPED_KEYBOARD,USER_ORIGIN,CONCEPT_UNKNOWN
       insert abstract concept into discourse history structure
       return
     retrieve first entry in chart
     examine category of chart element for broad match
       4a. is current chart entry a HOW_QUESTION
         parse status=processHowQuestion

```
    i) if parse_status=HOW_QUERY
      statement type=HOW_QUERY
      statement context=HOW_QUERY_CONTEXT
4b. is current chart entry a WHAT_QUESTION
    parse_status=processWhatQuestion
    i) if parse_status=WHAT_QUERY
      statement type=WHAT_QUERY
      statement context=WHAT_QUERY_
        CONTEXT
4c. is current chart entry a WHY_QUESTION
    parse_status=processWhyQuestion
    i) if parse_status=WHY_QUERY
      statement type=WHY_QUERY
      statement context=WHY_QUERY_CONTEXT
4d. is current chart entry a IF_QUESTION
    parse_status=processIfQuestion
    i) if parse_status=IF_QUERY
      statement type=IF_QUERY
      statement context=IF_QUERY_CONTEXT
4e. is current chart entry a VERB
    parse_status=processVerb
    i) if parse_status=GENERAL_EXPLAIN
      statement type=GENERAL_EXPLAIN
      statement context=GENERAL_EXPLAIN_
        COMMAND
    ii) else if parse_status=SPECIFIC_EXPLAIN
      statement type=SPECIFIC_EXPLAIN_
        COMMAND
      statement context=EXPLAIN_COMMAND
    iii) else if parse_status=GENERAL_CONCERN
      statement type=GENERAL_CONCERN_CMD
      statement context=SPECIFIC_CONCERN_
        CMD
    iv) else if parse_status=SPECIFIC_CONCERN
      statement type=SPECIFIC_CONCERN_
        COMMAND
      statement context=
    v) else if parse_status=GENERAL_DEMO
      statement type=GENERAL_DEMO_CMD
      statement context=
    vi) else if parse_status=SPECIFIC_DEMO
      statement type=SPECIFIC_DEMO_CMD
      statement context=
    create abstract concept:
      statement type,TYPED_KEYBOARD,USER_
        ORIGIN,statement context
      insert abstract concept into discourse history
        structure
4f. is current chart entry an AFFIRMATIVE
    parse_status=processAffirmative
    i) if parse_status=YES_CONTEXT
      statement type=YES_COMMAND
      statement context=YES_CONTEXT
    create abstract concept:
      statement type, TYPED_KEYBOARD, USER_
        ORIGIN,
      statement context
    add abstract concept to discourse history structure
4g. is current chart entry a NEGATIVE
    parse_status=processNegative
    i) if parse_status=NO_CONTEXT
      statement type=NO_COMMAND
      statement context=NO_CONTEXT
    create abstract concept:
      statement type,TYPED_KEYBOARD,USER_
        ORIGIN,statement context
      insert abstract concept into discourse history
        structure
4h. is current chart entry general statement
    parse_status=processGeneral
    i) if parse_status=CONCEPT_NOUN_AGE_
      MENARCHE
      statement type=CONCEPT_NOUN_AGE_
        MENARCHE
      statement context=SPECIFIC_CONCERN_
        AGE_MENARCHE
    ii) else if parse_status=CONCEPT_NOUN_
      AGE_FIRST_LIVE_BIRTH
      statement type=CONCEPT_NOUN_AGE_
        LIVE_BIRTH
      statement context=SPECIFIC_CONCERN_
        AGE_LVE_BRTH
    iii) else if parse_status=CONCEPT_NOUN_
      NUM_RELATIVES_HX_BCa
      statement type=CONCEPT_NOUN_NUM_
        RELATIVES_HX_BCa
      statement context=SPECIFIC_CONCERN_
        NUM_REL_HX_BCa
    iv) else if parse_status=CONCEPT_NOUN_
      PREVIOUS_BIOPSY
      statement type=CONCEPT_NOUN_PREV_
        BIOPSY
      statement context=SPECIFIC_CONCERN_
        PREV_BIOPSY
    v) else if parse_status=CONCEPT_NOUN_
      PAIN
      statement type=CONCEPT_NOUN_PAIN
      statement context=SPECIFIC_CONCERN_
        PAIN
    vi) else if parse_status=CONCEPT_NOUN_
      NIPPLE_DISCHARGE
      statement type=CONCEPT_NOUN_NIPPLE_
        DISCHARGE
      statement context=SPECIFIC_CONCERN_
        NIPPLE_DSCHRG
    vii) else if parse_status=CONCEPT_NOUN_
      PALPABLE_MASS
      statement type=CONCEPT_NOUN_
        PALPABLE_MASS
      statement context=SPECIFIC_CONCERN_
        PALPABLE_MASS
    viii) else if parse_status=CONCEPT_NOUN_
      ARCH_DISTORT
      statement type=CONCEPT_NOUN_ARCH_
        DISTORT
      statement context=SPECIFIC_CONCERN_
        ARCH_DISTORT
    viiii) else if parse_status=CONCEPT_NOUN_
      ASYMMETRY
      statement type=CONCEPT_NOUN_
        ASYMMETRY
      statement context=SPECIFIC_CONCERN_
        ASYMMETRY
    x) else if parse_status=CONCEPT_NOUN_
      DEVELOPING_DENSITY
      statement type=CONCEPT_NOUN_
        DEVELOPING_DENSITY
      statement context=SPECIFIC_CONCERN_
        DEV_DENSITY
    xi) else if parse_status=CONCEPT_NOUN_
      DILATED_DUCT
      statement type=CONCEPT_NOUN_
        DILATED_DUCT
      statement context=SPECIFIC_CONCERN_
        DILATED_DUCT
``` xii) else if parse_status=CONCEPT_NOUN_MASS_MARGIN
  statement type=CONCEPT_NOUN_MASS_MARGIN
  statement context=SPECIFIC_CONCERN_MASS_MARGIN
xiii) else if parse_status=CONCEPT_NOUN_MASS_DENSITY
  statement type=CONCEPT_NOUN_MASS_DENSITY
  statement context=SPECIFIC_CONCERN_MASS_DENSITY
xiiii) else if parse_status=CONCEPT_NOUN_MASS_SIZE
  statement type=CONCEPT_NOUN_MASS_SIZE
  statement context=SPECIFIC_CONCERN_MASS_SIZE
xv) else if parse_status=CONCEPT_NOUN_HALO_SIGN
  statement type=CONCEPT_NOUN_HALO_SIGN
  statement context=SPECIFIC_CONCERN_HALO_SIGN
xvi) else if parse_status=CONCEPT_NOUN_TUMOR_LOCATION
  statement type=CONCEPT_NOUN_TUMOR_LOCATION
  statement context=SPECIFIC_CONCERN_TUMOR_LOCATN
xvii) else if parse_status=CONCEPT_NOUN_CALC_CLUSTER_SHAPE
  statement type=CONCEPT_NOUN_CALC_CLUSTER_SHAPE
  statement context=SPECIFIC_CONCERN_CALC_CLST_SP
xviii) else if parse_status=CONCEPT_NOUN_NUM_CALCS_IN_CLUSTER
  statement type=CONCEPT_NOUN_NUM_CALCS_IN_CLUSTER
  statement context=SPECIFIC_CONCERN_NM_CLC_CLST
xviiii) else if parse_status=CONCEPT_NOUN_CALCIFICATION_SHAPE
  statement type=CONCEPT_NOUN_CALCIFICATION_SHAPE
  statement context=SPECIFIC_CONCERN_CALC_SHAPE
xx) else if parse_status=CONCEPT_NOUN_CALCIFICATION_DENSITY
  statement type=CONCEPT_NOUN_CALCIFICATION_DENSITY
  statement context=SPECIFIC_CONCERN_CALC_DENSITY
xxi) else if parse_status=CONCEPT_NOUN_CALC_ARRANGEMENT
  statement type=CONCEPT_NOUN_CALC_ARRANGEMENT
  statement context=SPECIFIC_CONCERN_CALC_ARRANGE
xxi) else if parse_status=CONCEPT_NOUN_CALCIFICATION_SIZE
  statement type=CONCEPT_NOUN_CALCIFICATION_SIZE
  statement context=SPECIFIC_CONCERN_CALC_SIZE
xxii) else if parse status=CONCEPT_UNKNOWN
  statement type=COMMAND_UNKNOWN
  statement context=SPECIFIC_CONCERN_UNKNOWN
  create abstract concept:
    statement type,TYPED_KEYBOARD,USER_ORIGIN,statement context
    add abstract concept to discourse history structure PDL Parser::ProcessVerb
1. parse status=processWantVerb
  1a. if parse status indicates user wants general information
    return GENERAL_CONCERN
  1b. if parse status indicates user wants specific information
    return SPECIFIC_SPECIFIC
2. parse status=processDemoVerb
  2a. if parse status indicates user wants system to show or demo general concept
    return GENERAL_DEMO
  2b. if parse status indicates user wants system to show or demo specific concept
    return SPECIFIC_DEMO
3. parse status=processExplainVerb
  3a. if parse status indicates user seeks explanation for general concept
    return GENERAL_EXPLAIN
  3b. if parse status indicates user seeks explanation for specific concept
    return SPECIFIC_EXPLAIN
4. else
  return FALSE PDL Parser::ProcessExplainVerb
1. Get size of chart (number of word entries for current utterance)
2. Retrieve first chart element
3. Determine if first chart element is an 'explain' verb
  3a. For all verbs in dictionary 'explain' verb
    compare chart element word, using first four characters
    if chart element word does NOT matches dictionary 'explain' verb
    return CONCEPT_UNKNOWN
    else determine what concept needs explaining
  3b. Retrieve next chart element
    For all nouns in dictionary 'general' nouns
      compare chart element word, using first four characters
    if chart element word matches dictionary 'general' noun
      return GENERAL_EXPLAIN
    For all nouns in dictionary 'specific' nouns
      compare chart element word, using first four characters
    if chart element word matches dictionary specific noun
      set concept noun to specific noun class
      return SPECIFIC_EXPLAIN
      return CONCEPT_UNKNOWN Knowledge Representation Module—Semantic Network Structure In order to provide the user with explanations, the knowledge representation module incorporates a semantic network structure. This semantic network structure embodies the "meaning" of the system: it encodes network and user-entered evidence data. The semantic network structure contains node information, i.e., domain variable data, from the nodes of the Bayesian network. This includes information on node name and type (hypothesis, risk factors, mass information, calcification information, indirect indications, physical symptoms), number and names of states, and node interrelationships (i.e., which node influences another node). Dynamic information in the form of user-entered evidence (from the evidence vector of the Bayesian inference engine) is additionally stored in the semantic structure. The semantic network structure provides the data and the logic to use this information to provide "importance" or "ordering" information in explanation construction. The system uses this structure as a knowledge source in its process of constructing rich explanations in support of the ongoing dialog between the system participants.

The semantic network structure is constructed at system initialization and consists of an entry for each node in the Bayesian network. Semantic network structure functions provide support for the system to access information when generating explanations desired by the user. These routines access information on the "importance" or "ordering" of user-entered evidence in terms of the nodes of the network. Routine SsgetRiskOrdering( ) accesses the user-entered evidence (the evidence vector from the Bayesian inference subsystem) and provides the system with an ordering of importance of risk factors, physical history, mass, calcification, and indirect indications for the user, dependent on the user-entered evidence. This information is used by the system component "The Explainer" to create a graph of risk factors, physical symptoms, and mammographic indications (mass, calcifications, and indirect indications) ordered in importance for this particular user. The ordering is set based on the statistical information from the Bayesian Inference knowledge base.

The semantic network structure consists of a list of semantic entries, numbering one for each node in the network. A semantic entry consists of information including node number (in the network), node type (risk factor, mass node, calcification node, indirect indication node), number of node states, the node name, and the current setting of the node (if the user has entered evidence against this node, the current setting is set to the value of this node in the evidence vector from the Bayesian network). Associated with the semantic network structure are routines that maintain this structure. The structure is set to correspond to a user's entered evidence (through the graphical user interface and set in the current evidence vector for the current session). A new session causes this structure to be reset with the specific user information (this is the dynamic information).

Ordering information of risk factors, mammographic direct and indirection indications, and physical symptoms is calculated dynamically given a specific user's entered evidence. This information is used in the ongoing dialog between system participants. For example, it can be presented as a graphical depiction of an ordered graph of risk factors, physical symptoms, mammographic mass indications, calcification indications, and indirect mammographic indications. The components of the graph are present if the user has indicated such evidence. The ordering or sensitivity of a graph component is based on the strength of that piece of evidence in the determination of the probability of breast cancer for the specific user session.

Multimodal Discourse Module

The multimodal discourse module is central to the architecture of the system. Discourse processing is the task of creating a dynamic representation of the multimodal interaction that defines the relations between the system's and the user's actions. The system incorporates an explicit discourse model, which represents the content and the structure of the ongoing interaction. The discourse module supports statements of facts concerning the domain, questions about the domain, commands to provide an explanation, and referring expressions.

In the system's multimodal environment, typing, presentation graphics, and mouse gestures perform these discourse activities. For example, in the sample dialog between the system and Mrs. Smith provided above, the system presents a bar graph to introduce factors and to describe their relative importance (Line 6). The patient questions the system as to what she can do to improve her situation (Line 10). The patient directs the system to explain how she can modify her risk factor age (Line 14). The patient clicks the box Age. The system interprets this action as a referring expression: age is now the focus of the discussion and the patient has requested an explanation.

The system's explicit multimodal discourse model supports context-sensitive explanations and user follow-up questions engaging the participants in an ongoing dialog with the goal of meeting the user's needs. The design of an explicit discourse model is also necessary due to the complexity of the system and the intractability of anticipating all user questions and directives. The multimodal discourse model represents different types of information from the modalities and specifies how this information interacts.

In addition to constructing a representation of the ongoing dialog, the multimodal discourse module 16 constructs explanations and makes high-level decisions on how these explanations are presented to the user. In the above sample dialog between the system and Mrs. Smith, the discourse module interpreted the patient's statement in Line 4 as a request for an explanation. The discourse module 16 constructs the content of the explanation—relevant risk factors—and decides on a presentation approach as a one-dimensional bar chart of ranked risk factors (Line 6). This information, the explanation content and the presentation specifications, is sent to the output module 22 (FIG. 39). The discourse module dictates the content and the presentation style of the explanation, leaving the details of the presentation to the output module 22.

Multimodal Discourse Module—Dialog Component

A dialog is a representation of an ongoing dialog between system participants which captures knowledge about the context and structure of a system utterance. This representation is implemented as a table of dialog entries. A dialog entry is comprised of four information units: command type, modality type, speaker type, and context type. These four units of information correspond to the abstracted parse results output from the knowledge representation module. The command type embodies the desired action of a system participant. The modality type indicates the method of communication (typed text, graphics, mouse clicks, displayed text). The speaker type identifies the origin of the system participant. The context type identifies what the context of the current conversation is.

When an utterance from the user or the system is identified and abstracted in the knowledge representation module, this abstraction is inserted into the format of a dialog entry. This entry, in turn, is added into table of dialog entries, which represent the ongoing dialog between both participants. The dialog structure (also referred to as the discourse history structure) is a table of dialog entries, and is maintained dynamically throughout the dialog session between the user and the system.

During a dialog session between the user and the system, the system monitors this dialog structure to keep track of the context of the conversation. This is important when there appears to be a misunderstanding between the system participants. The multimodal discourse module 16 will examine the dialog entries in the dialog table attempting to determine the context of the conversation, and ask appropriate questions to return the dialog to a meaningful state. The system will summarize the immediate history of the conversation to the user, and attempt with questions to understand the user's utterances. If the misunderstanding can not be repaired the system will indicate it does not understand the user.

Multimodal Discourse Module—Explanation Component "The Professor"

The system is capable of providing explanations to a wide range of users: the system can provide explanations to users who are concerned with the "how" of the system. How does the system work? What are its components? What are the nodes? What are the node states? The component of the discourse module 16 that manages this task is the explanation component called "The Professor".

Figure 44:
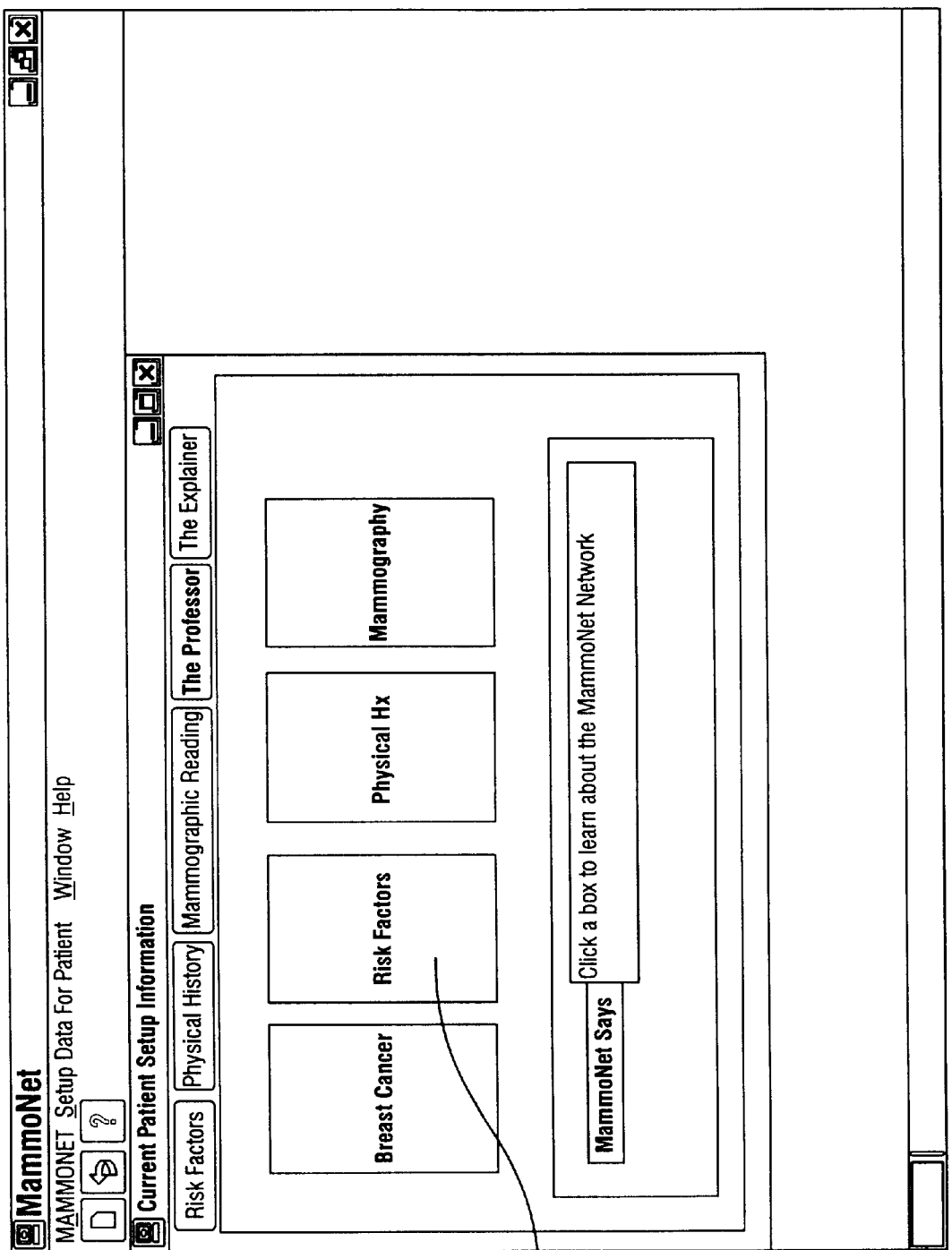
FIGS. 44–47 are possible screens generated by "The Professor" component during interaction with a user attempting to find out about the structure of the Bayesian network.
Figure 45:
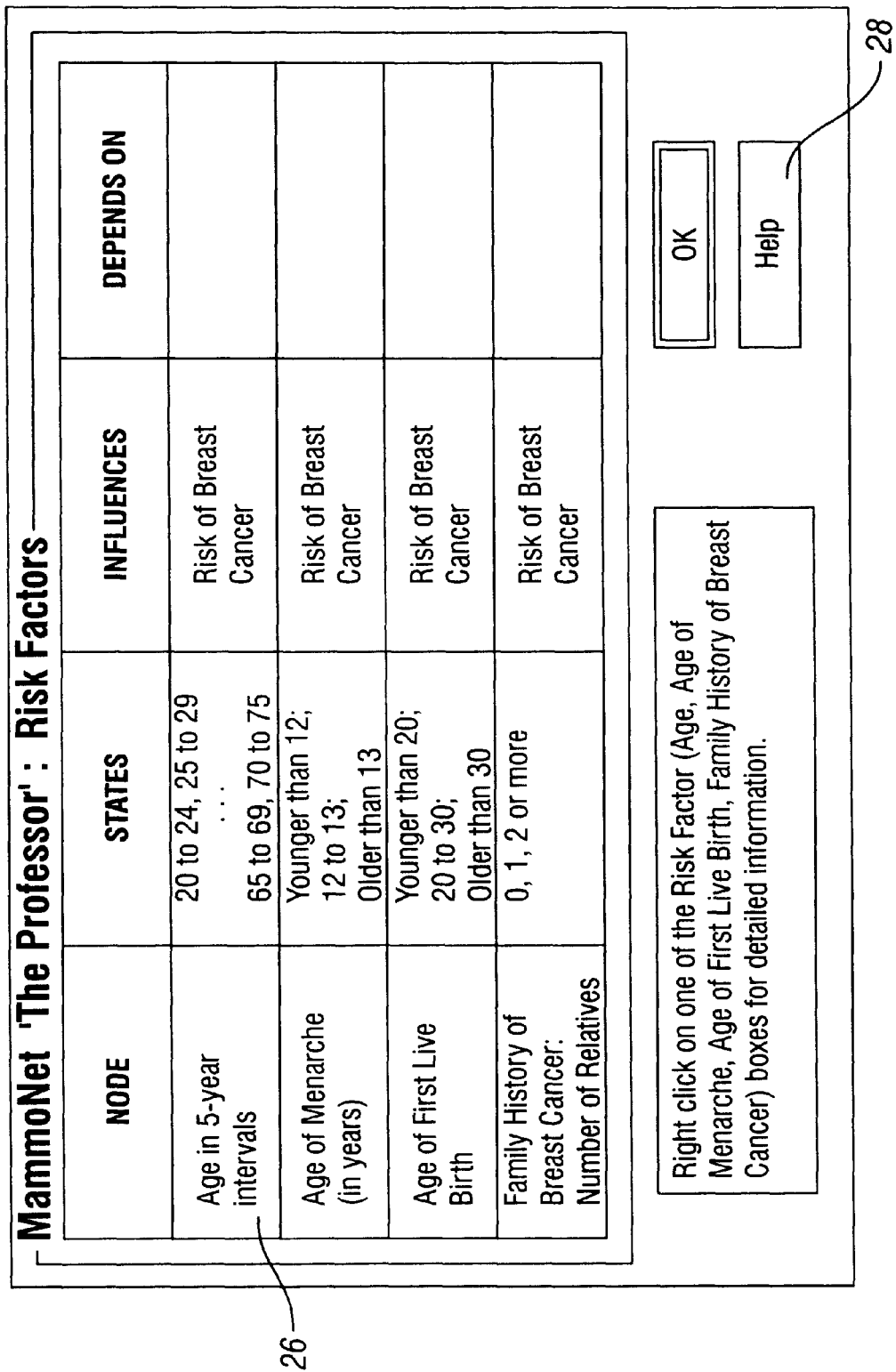
Figure 46:
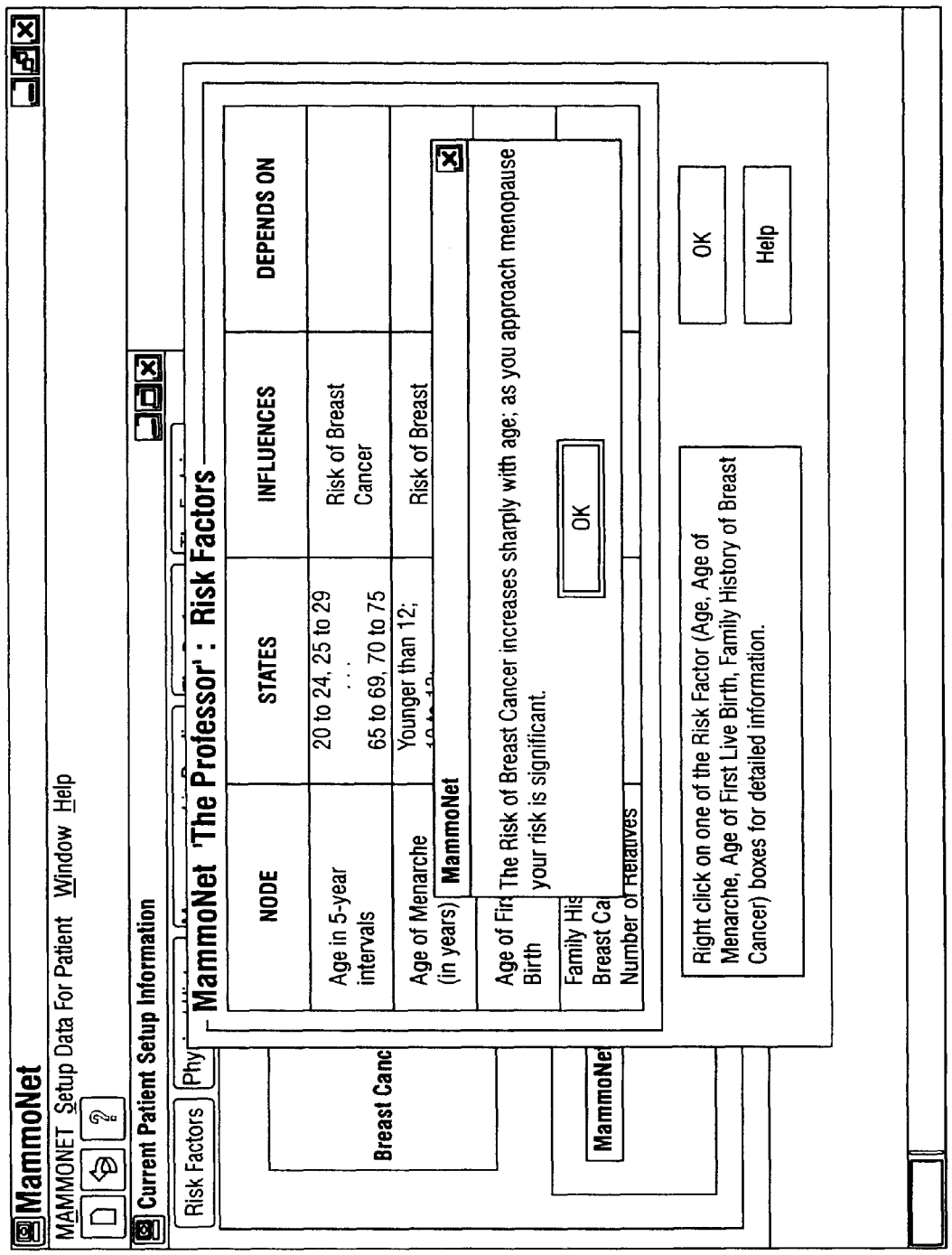
Figure 47:
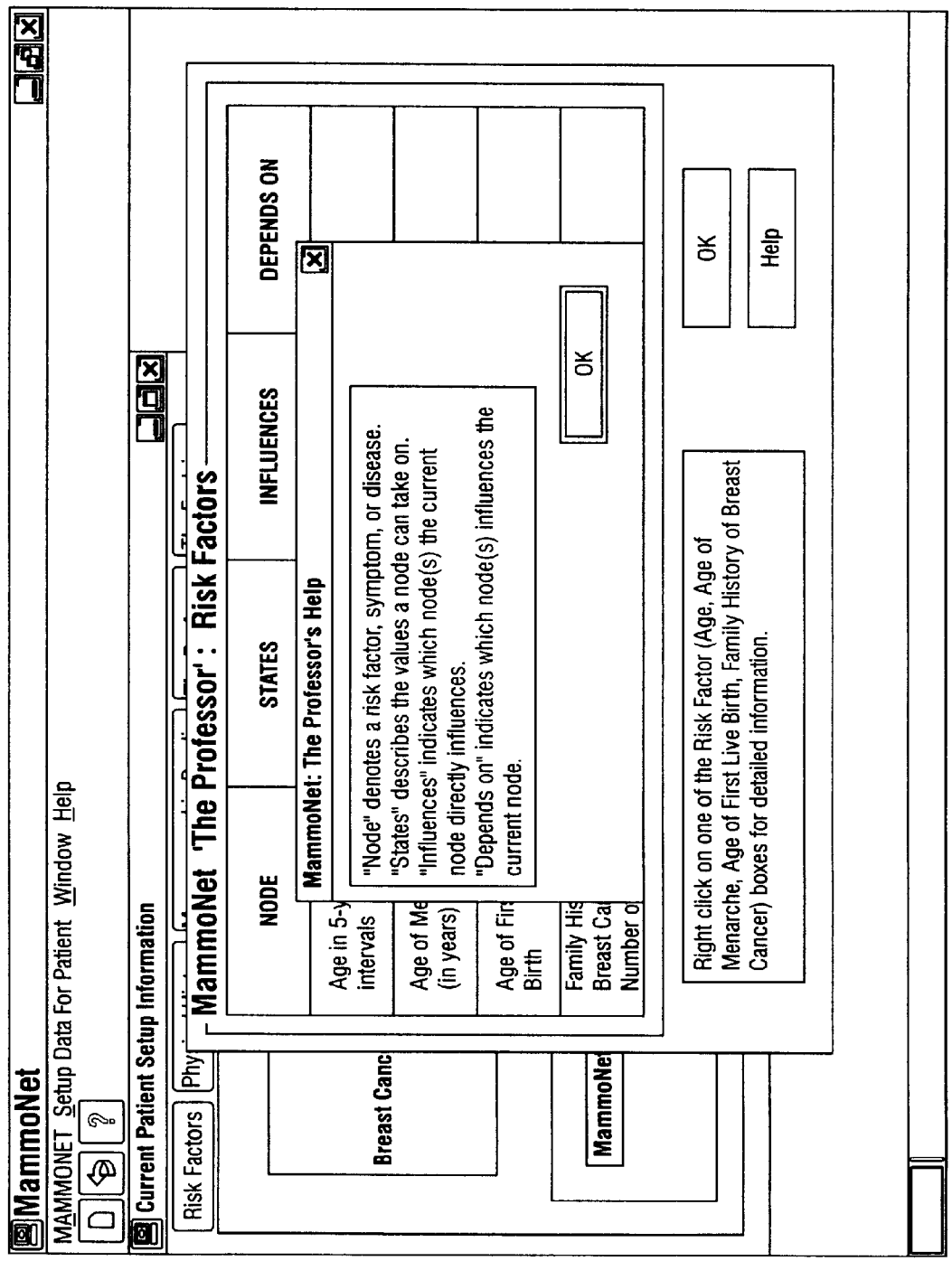

Referring to FIGS. 44–47, a sample exchange between a user and the system is depicted. In FIG. 44, The Professor provides the user with a display of clickable buttons. The user can click a button from a group of buttons, which are categorized into node types or logical groupings (e.g., hypothesis node, risk factor nodes, physical history nodes, mammographic mass indication nodes, mammographic calcification indication nodes, and mammographic indirect indication nodes). If, for example, the user clicked on the "Risk Factors" button 24 in FIG. 44, the user is presented with a graphical chart (FIG. 45) of the specific nodes that comprise the logical groupings in the network. The chart is made up of node name, node states, node dependencies, and node influences. The purpose of this chart is to explain the structure of the model. The user is presented with node information and information on how the nodes relate to each other in the network. Additionally, the user can right-click with a mouse on the node name and obtain detailed information on that node. For example, if a user viewing a screen like FIG. 45 were to click on the "Age in 5-year intervals" box 26, the user may be presented with a screen like the one depicted in FIG. 46. FIG. 47 depicts a sample screen presented by The Professor in response to a user having clicked the "Help" button 28 on FIG. 45.

Multimodal Discourse Module—Explanation Component "The Explainer"

Unlike users who are concerned with the mechanics or structure of the system, there are users who are concerned with how the system relates its conclusions to their specific situation. This system is capable of providing explanations to users concerned with questions about their likelihood of breast cancer as it relates to their specific situation. The system provides these explanations using a combination of modalities, including text displays and graphics. These are questions and statements of the kind: "I am worried about my health." "Tell me why my risk is such." "Yes, I'd like more information on what I can do to improve my situation." "Tell me why the mass in my left breast is likely cancerous," and so forth. The component of the multimodal discourse module 16 that manages this type of discourse is "The Explainer."

Figure 48:
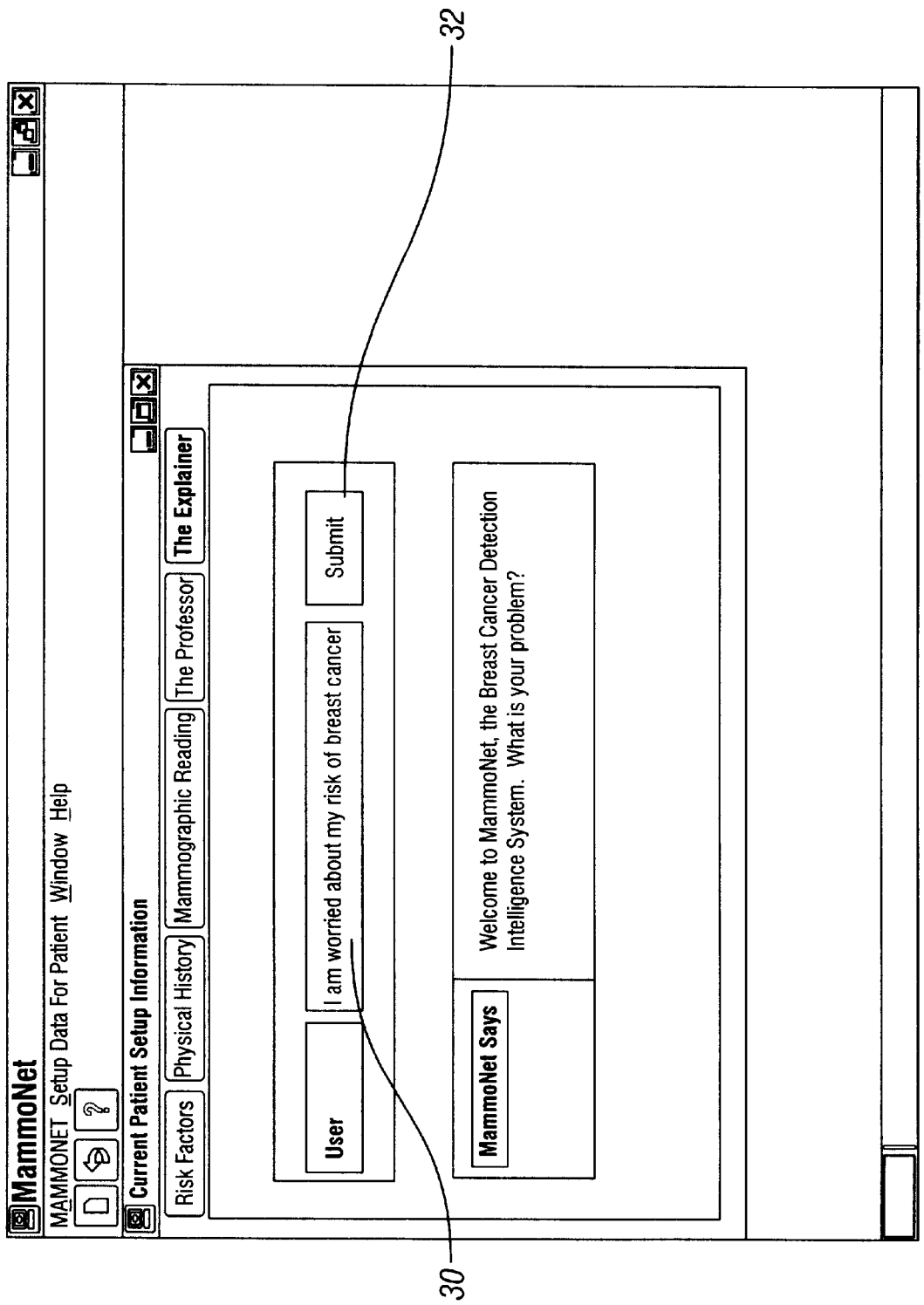
FIGS. 48–56 contain screens from "The Explainer" component as a user interacts with the system concerning her risk of breast cancer.
Figure 49:
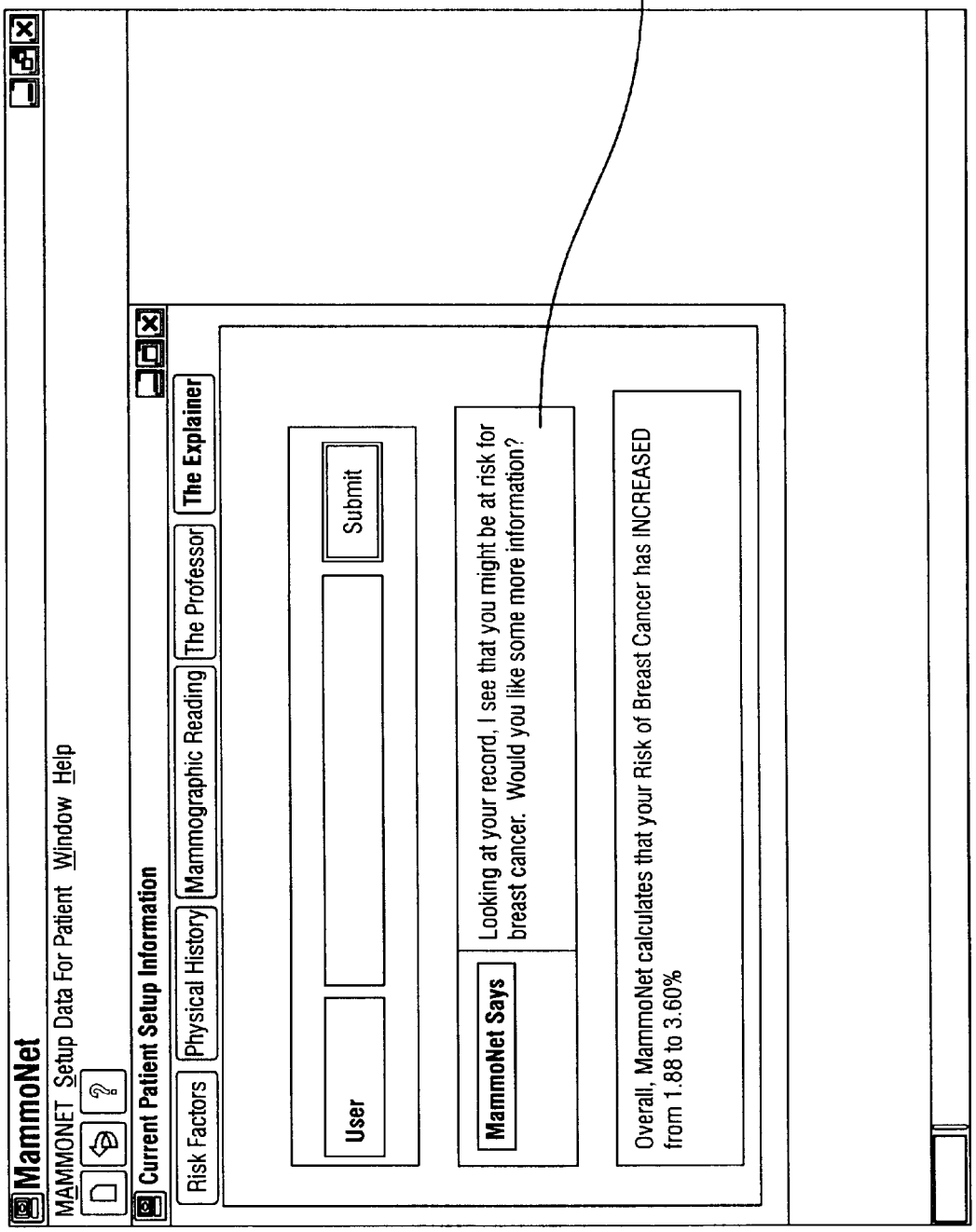

"The Explainer" encapsulates the information necessary to provide the user and the system with information to carry on a dialog with questions, statements, and answers. As shown in FIG. 48, the user may be presented with a type-in text box 30, though which the user can type in statements or questions. In the sample shown in FIG. 48, the user has typed, "I am worried about my risk of breast cancer." Alternatively, the mouse can be used for pointing and referring, and selection options. "The Explainer" of the preferred embodiment, therefore, supports two modalities: mouse clicks and typed text input. The Parser in the knowledge representation module 14 processes the typed input, parsing and encoding the utterance into an abstract concept which is then stored as dialog entries in the dialog table. The evidence vector from the Bayesian network provides the semantic structure of the knowledge representation module 14 with information for the particular user. The semantic structure provides "The Explainer" with information on the network structure, and the specific entered evidence for the current user session. A user can enter evidence through the graphical interface, and then enter "The Explainer." This component provides the processing to support the ongoing dialog of questions, statements, and answers between the system participants. The user can request further information on how the system calculates her risk; the system provides graphical and typed-text display responses by sending the explanations and the presentation specifications to the output module 22. In turn, the output module 22 interprets the presentation specifications and supports the actual display of the explanations.

Figure 50:
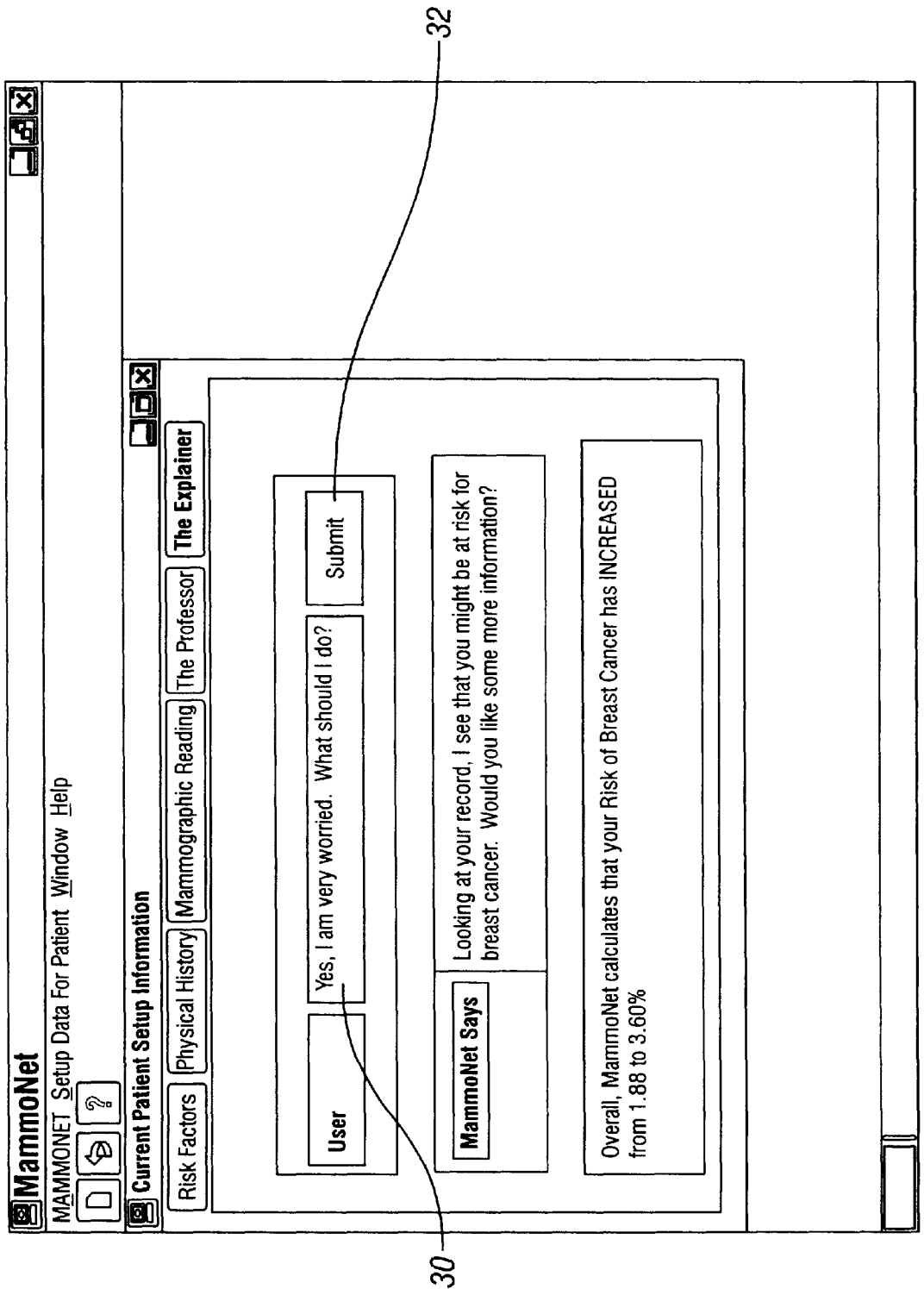
Figure 51:
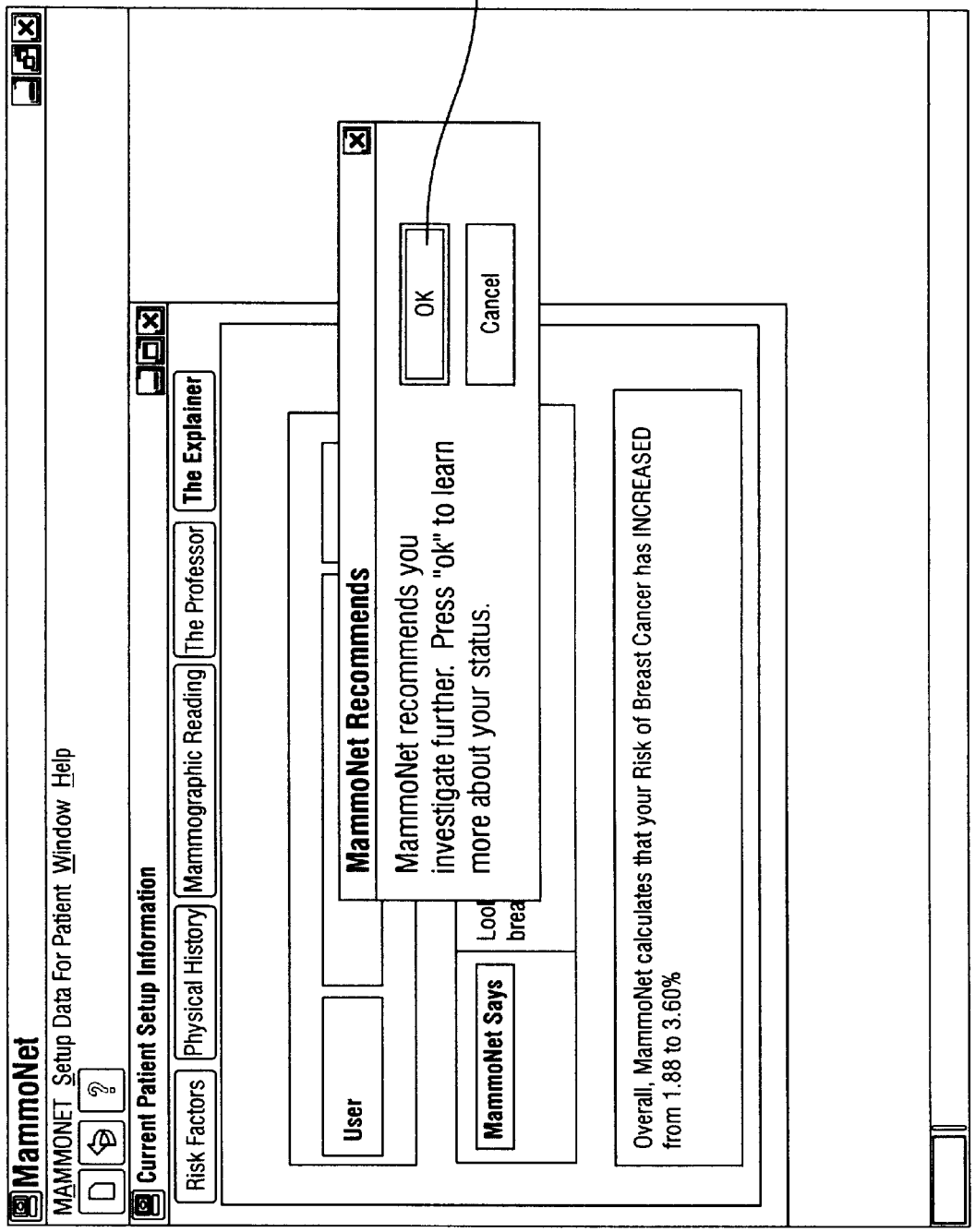
Figure 52:
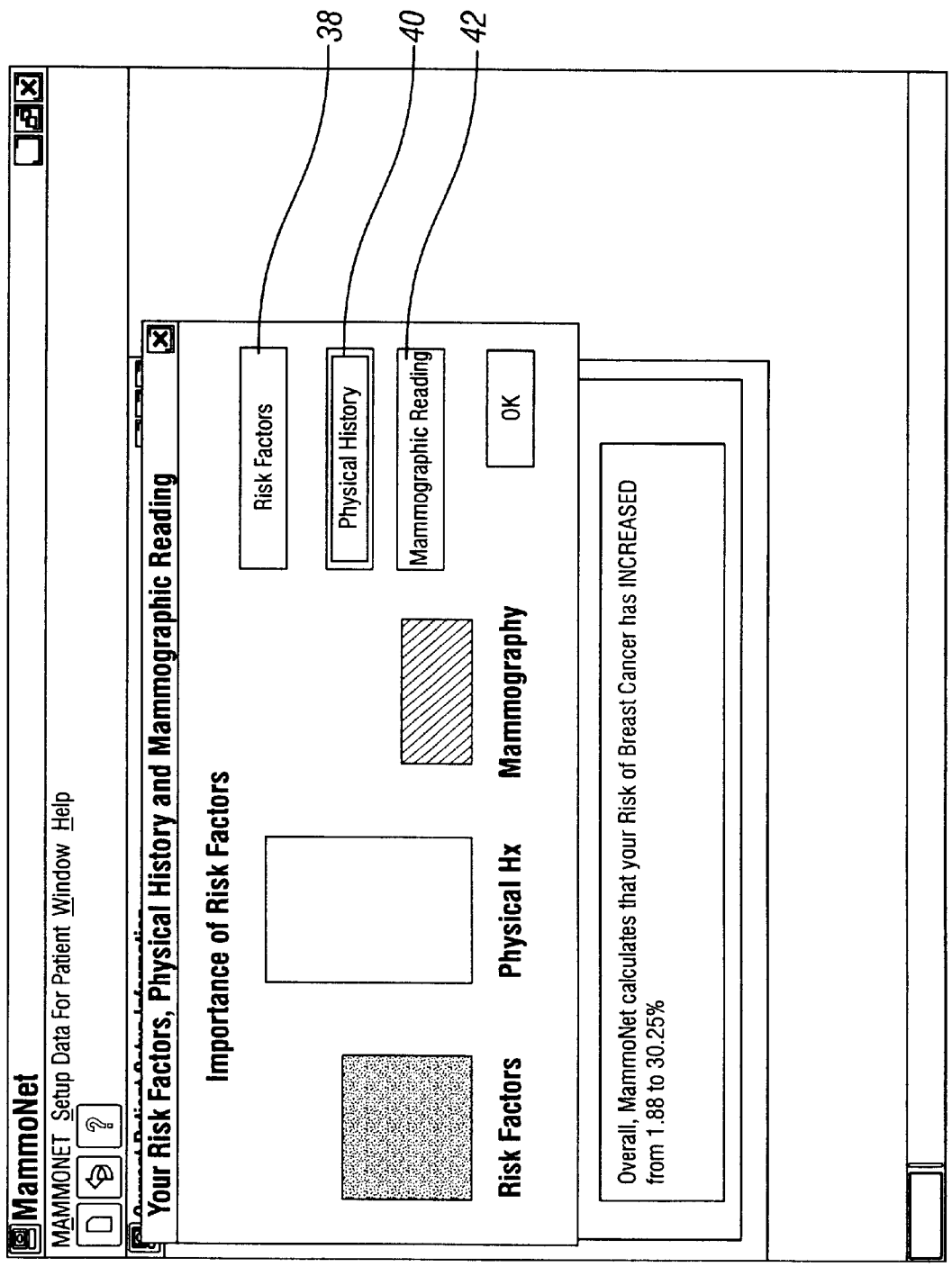

Referring to FIGS. 48–56, a sample exchange between a user and "The Explainer" is depicted. As shown in FIG. 48, while "The Explainer" is active, a user has typed in the statement, "I am worried about my risk of breast cancer" in test box 30. Upon clicking on the "Submit" button 32, the system performs various statistical analyses on the user's data, and then generates the statement 34 shown in FIG. 49, offering to provide further information. As shown in FIG. 50, the user can indicate her interest in the offered information by typing an appropriate statement in the user submission box 30. For example, as shown in FIG. 50, the user typed, "Yes, I am very worried. What should I do?" When the user then clicks on the "Submit" button 32, the system begins offering additional information. If the system has additional information to provide, it will recommend that the user investigate further (FIG. 51). If the user chooses to continue (by clicking the "OK" button 36 in FIG. 51), a screen similar to FIG. 52 may be displayed. In FIG. 52, "The Explainer" presents a graphic (in this case a bar chart), showing the relative importance of risk factors, physical history, and mammographic readings to this user's risk of breast cancer. Three clickable boxes 38, 40, 42 ("Risk Factors," "Physical History," and "Mammographic Reading") are simultaneously presented. If a user were, for example, to click on the "Risk Factors" button 38 in FIG. 52, "The Explainer" generates an explanatory box 44 like that shown in FIG. 53.

Figure 53:
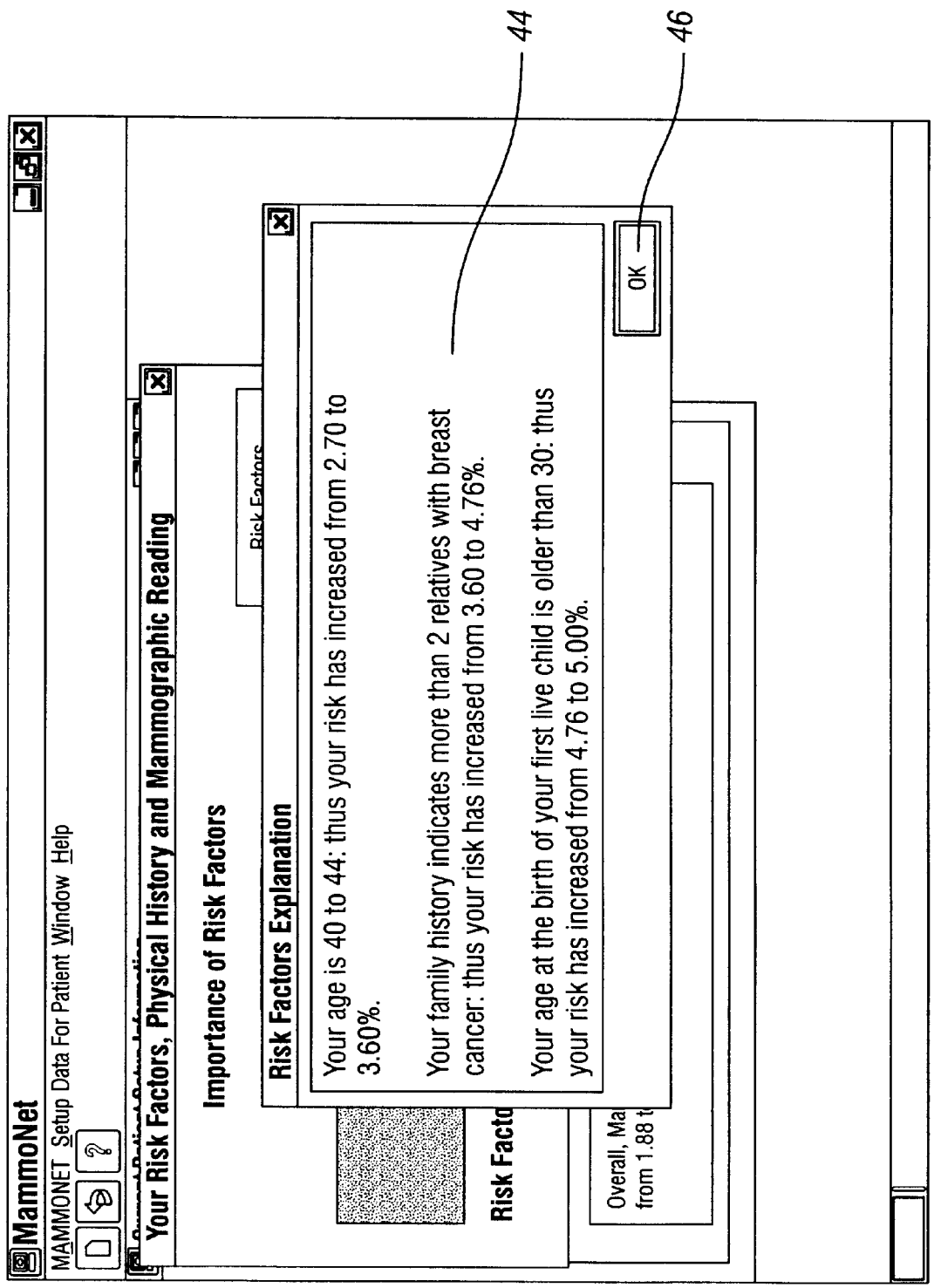
Figure 54:
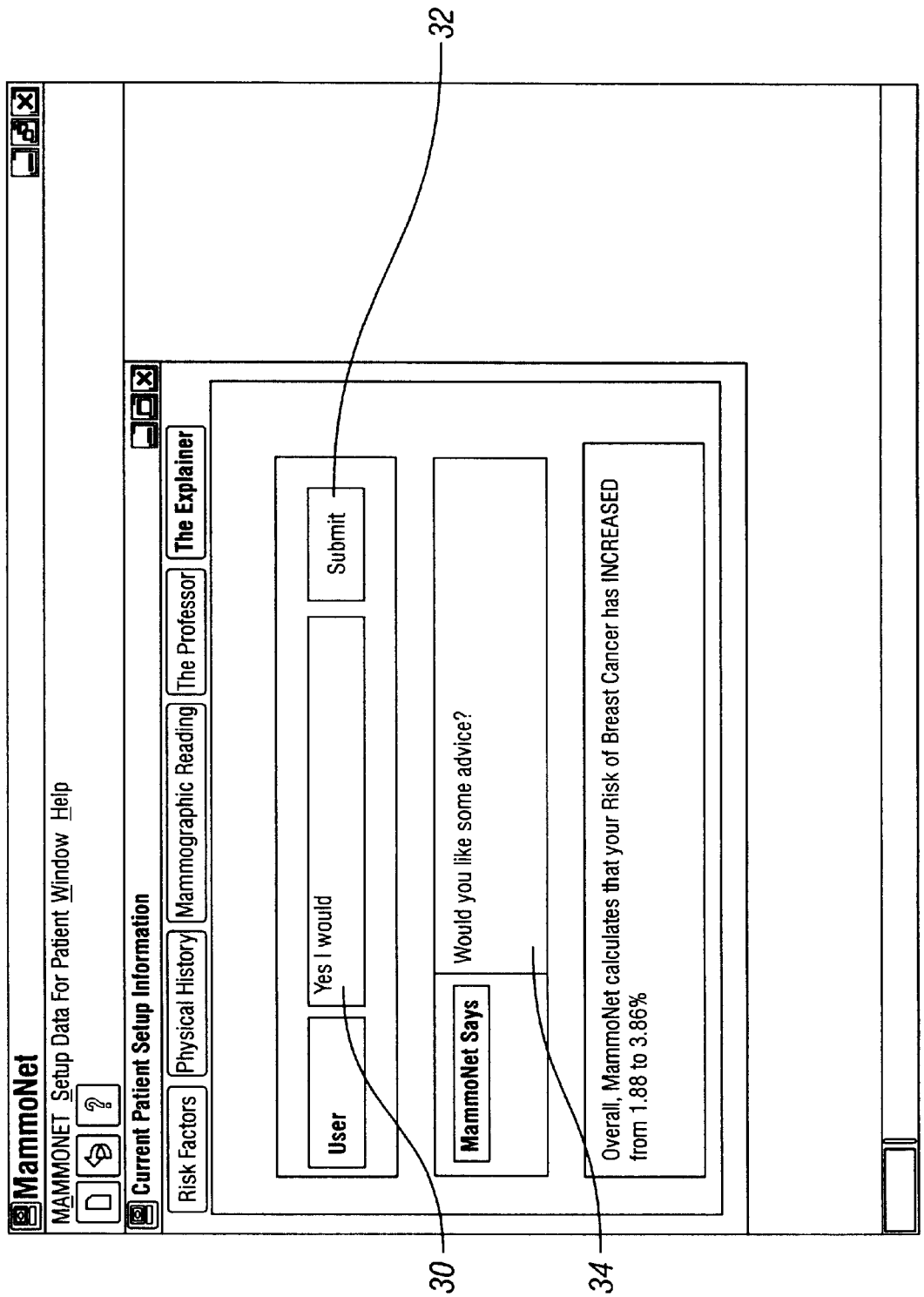

After the user clicks the "OK" button 46 in FIG. 53, "The Explainer" gives her an opportunity to request still further information. For example, as shown in FIG. 54, "The Explainer" has asked the user whether she wants more information, and the user has typed an affirmative response, which has not yet been submitted to "The Explainer." Once the user clicks the "Submit" button 32 in FIG. 54, a screen similar to FIG. 55 may be presented to her.

Figure 55:
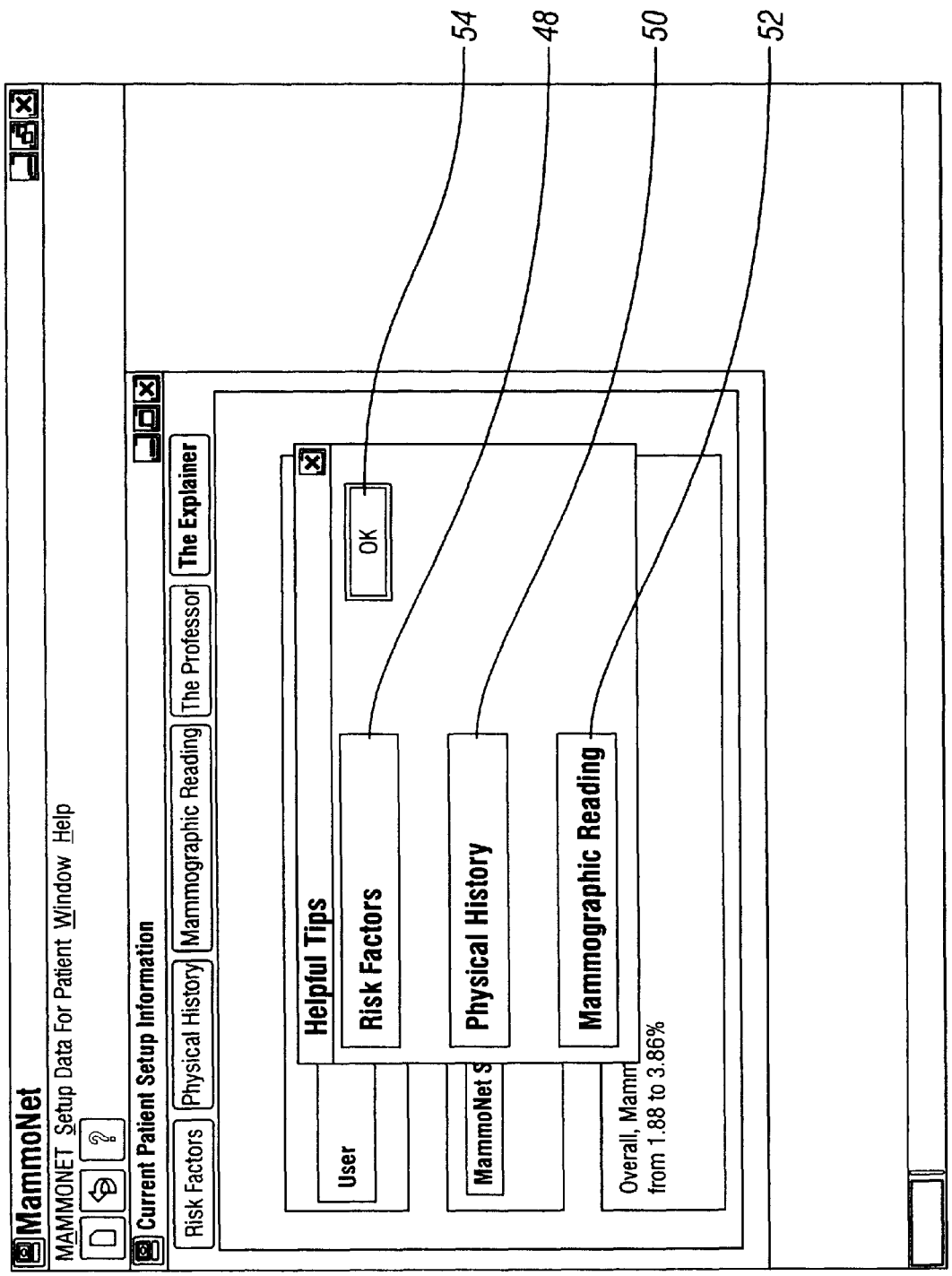
Figure 56:
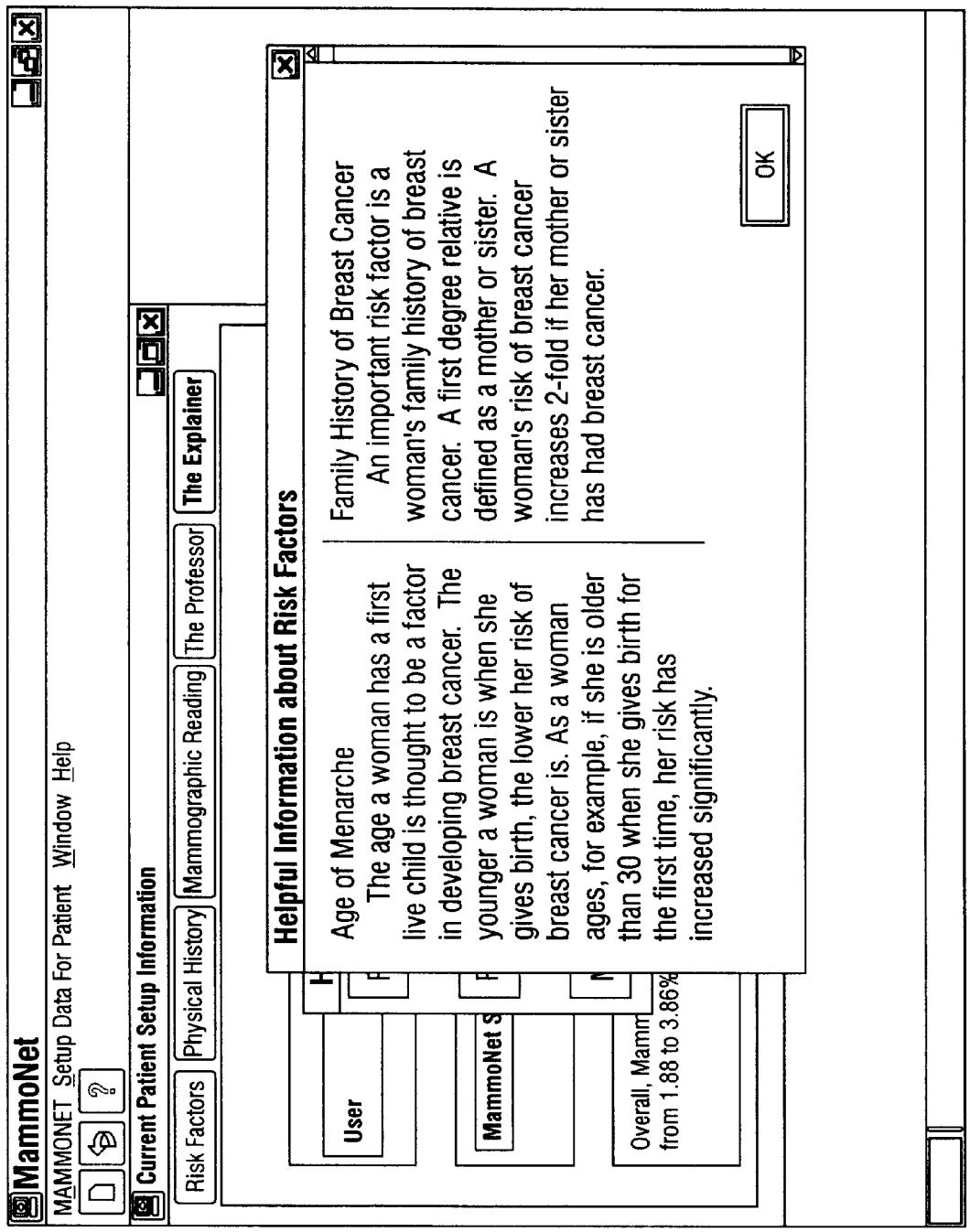

As shown in FIG. 55, the user is presented with three click boxes 48, 50, 52. If the user wants helpful tips about risk factors, she could click on the "Risk Factors" box 48 for helpful tips about her physical history. She could click on the "Physical History" box 50 for helpful tips about her mammographic reading, or she could click on the "Mammographic Reading" box 52. If she were to decide that she did not want helpful tips, a click on the "OK" button 54 would return her to the previous screen (FIG. 54). If, for example, while viewing FIG. 55 the user requested helpful tips about risk factors by clicking on the "Risk Factors" box 48 in FIG. 55, the screen depicted in FIG. 56 would be presented. In this screen, the user is presented with the promised helpful information.

Output Module

The component of the multimodal user interface 12 (FIG. 39) that provides presentation services to the multimodal discourse module 16 is the output module 22. This module 22 is comprised of individual modules for the different modalities (text, graphics, and animation) that provide for the management of style and layout. The output module 22 converts the high-level presentation specifications that are generated by the discourse module 16 into choices of color, font, and layout as it displays the explanation content. The output module 22 acts as an interface through which the independent media modules can determine how to format information for presentation to the user. This design simplifies the individual modules for each modality, as each module handles a narrow set of formatting and rendering tasks. This approach simplifies future additions of new media to the system.

Figure 57A:
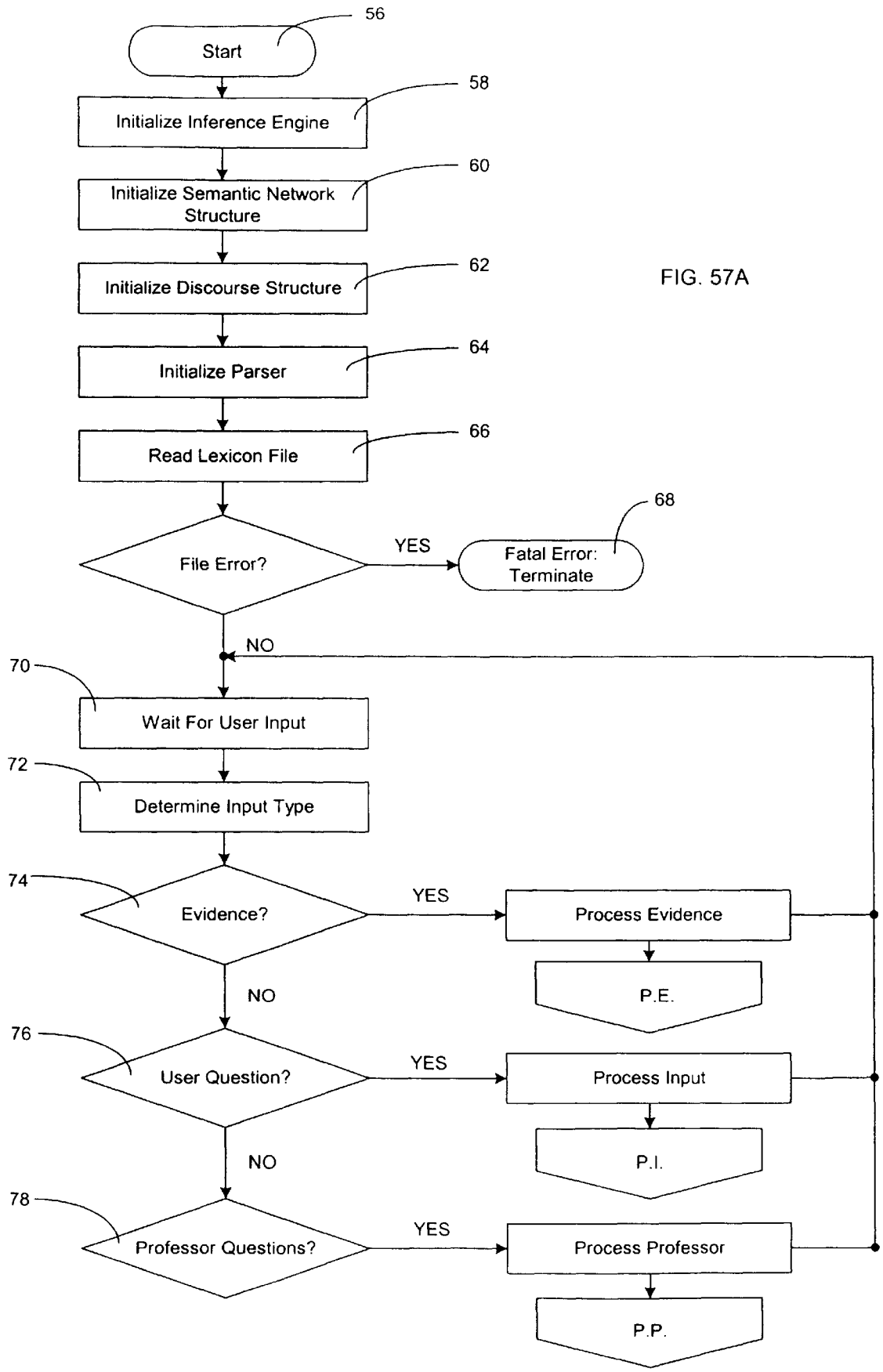
FIGS. 57A–57D comprise a high-level flow chart of the entire system.
Figure 57B:
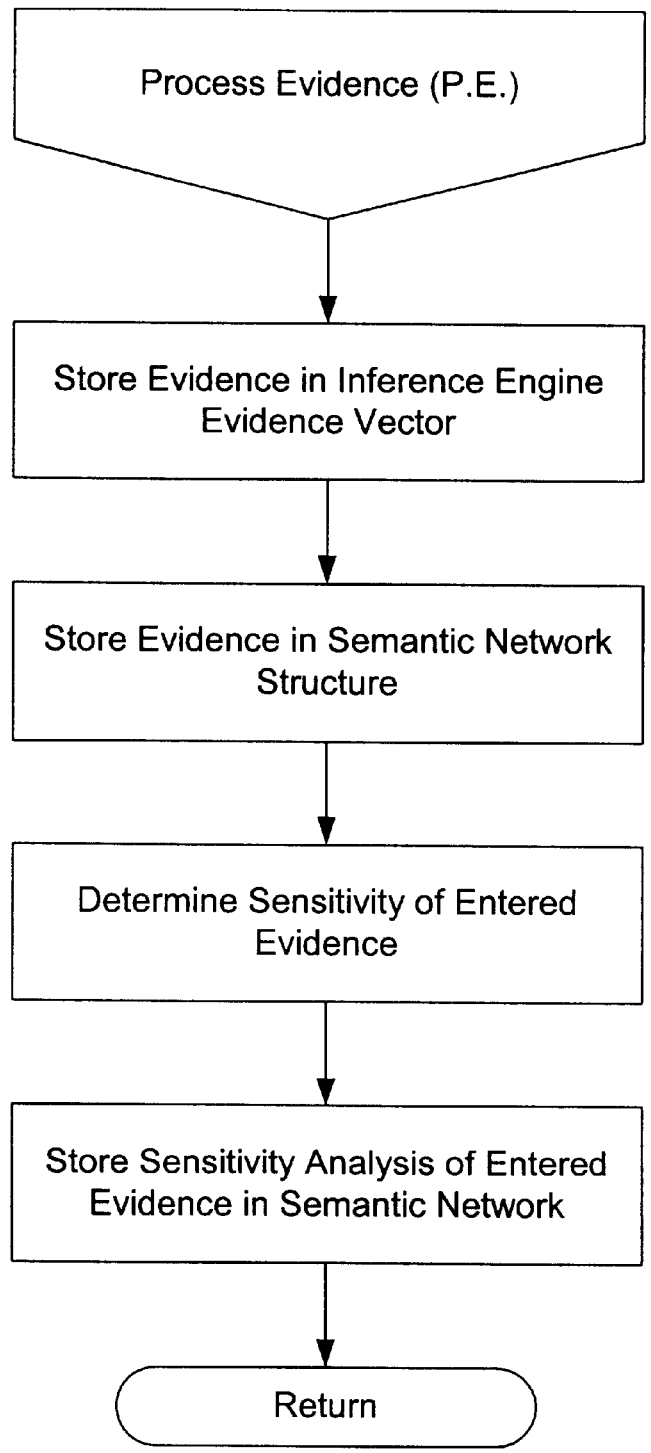
Figure 57C:
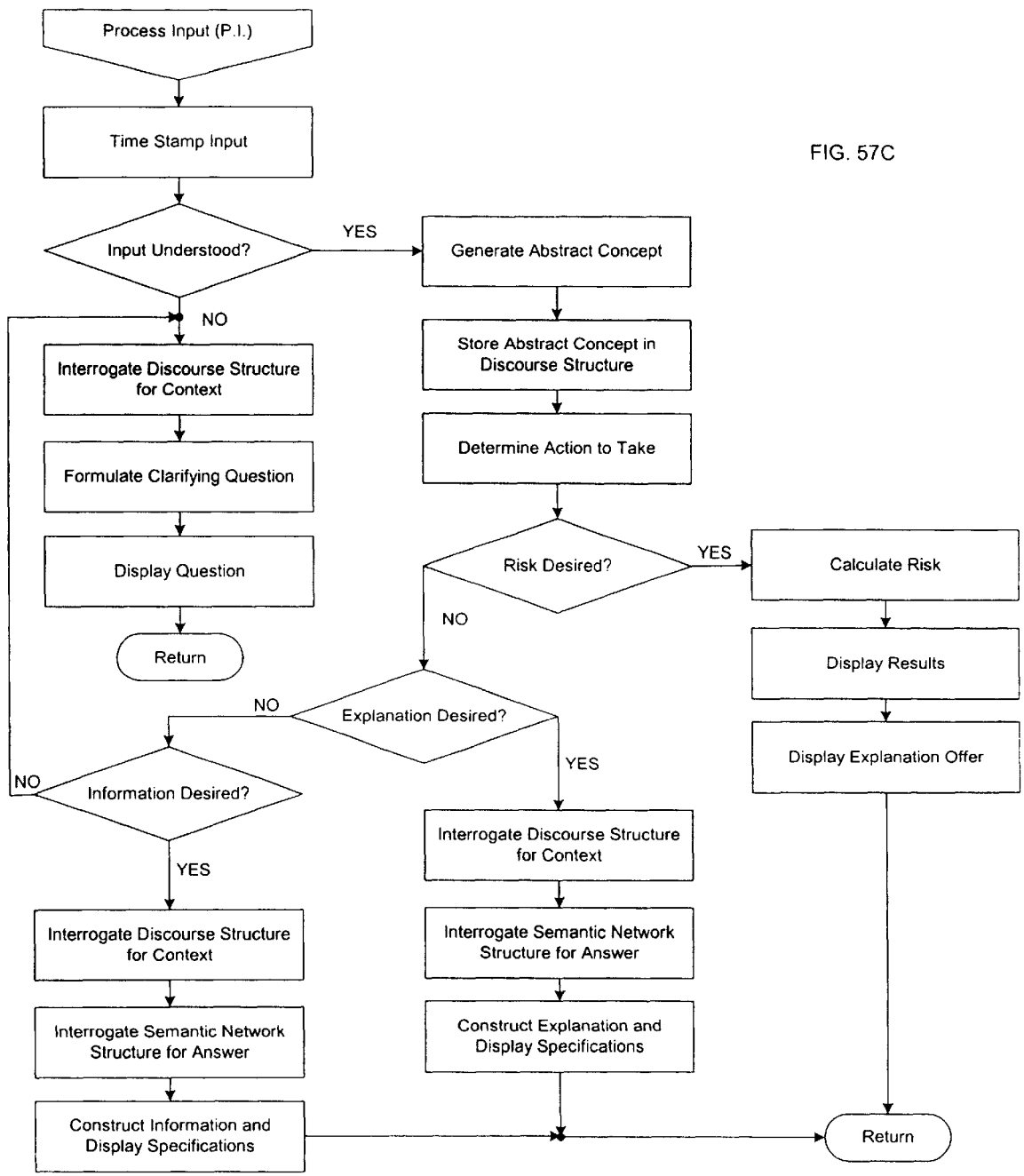
Figure 57D:
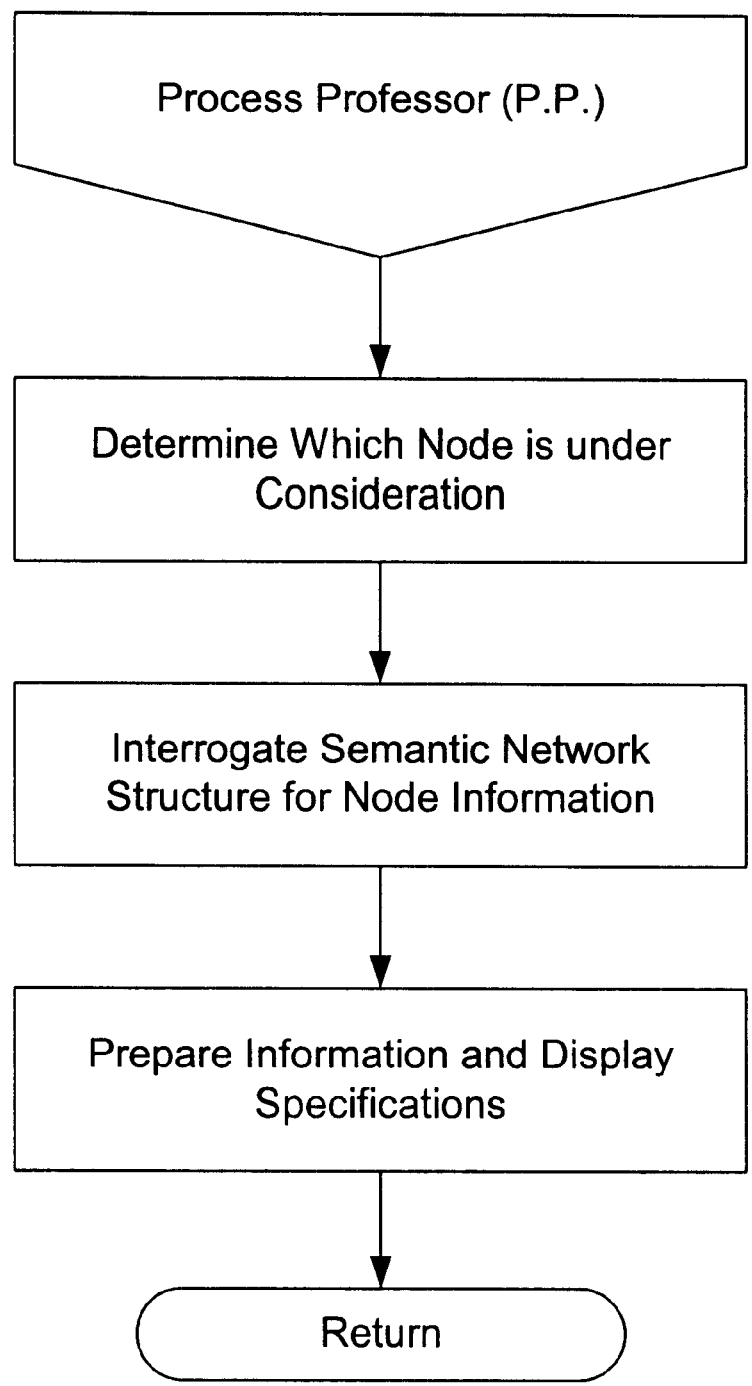

Referring next to FIGS. 57A–57D, which together comprise a high-level flow chart of the entire system, operation of the computer-aided diagnostic support system of the preferred embodiment of the present invention is described next. As shown in FIG. 57A, operation commences at start block 56. The inference engine is initialized (block 58), the semantic network structure is initialized (box 60), the discourse structure is initialized (box 62), and the parser is initialized (box 64). Subsequently, the system attempts to read the lexicon file (box 66), which as described above is a collection of words related to the domain of interest (i.e., breast cancer in the preferred embodiment). If the system experiences problems reading the lexicon file, a fatal error is generated and the program terminates (box 68). If the lexicon file is properly read, the system then enters a wait state looking for user input (box 70). Once input is received, the system attempts to determine its type (box 72). If, for example, a user is attempting to input evidence, at box 74 control is transferred to a subroutine for processing the evidence (see FIG. 57B). If, alternatively, a user is attempting to learn more about how the system relates its conclusions to that user's particular situation, at box 76 control is transferred to a subroutine for responding to the user's questions (see FIG. 57C). If, as a third alternative, a user is interested in learning more about the structure of the system (e.g., how it works, its components, its nodes and their states), at box 78 control is transferred to a subroutine that provides the requested information to the user (see FIG. 57D). If control is transferred to one of the subroutines (FIGS. 57B–57D), the system eventually returns to the wait state (box 70 in FIG. 57A) until the next input from the user is received.

Although a preferred embodiment of this invention has been described above, those skilled in the art could make numerous alterations to the disclosed embodiment without departing from the spirit or scope of this invention. It is intended that all matter contained in the above description or shown in the accompanying figures shall be interpreted as illustrative only and not limiting.

I claim:

1. A computer-implemented method of providing medical decision support comprising the steps of
    (A) initializing an inference engine;
    (B) initializing a semantic network structure;
    (C) initializing a discourse structure;
    (D) initializing a parser;
    (E) reading a lexicon file;
    (F) waiting for user input;
    (G) receiving a multimodal input from a user;
    (H) determining a type of input received, wherein it is determined that said type of input is evidence; and
    (I) processing said input based upon said determined type, wherein said processing step comprises the steps of
        (i) storing said evidence in an inference engine evidence vector;
        (ii) storing said evidence in a semantic network structure;
        (iii) determining a sensitivity based upon said evidence; and
        (iv) storing said determined sensitivity in said semantic network structure.

2. A computer-implemented method of providing computer-aided medical decision support comprising the steps of
    (A) initializing an inference engine;
    (B) initializing a semantic network structure;
    (C) initializing a discourse structure;
    (D) initializing a parser;
    (E) reading a lexicon file;
    (F) waiting for user input;
    (G) receiving a multimodal input from a user;
    (H) determining a type of input received, wherein it is determined that said type of input is a Professor question; and
    (I) processing said input based upon said determined type, wherein said processing step comprises the steps of
        (i) determining which node is under consideration;
        (ii) interrogating said semantic network structure for node information;
        (iii) preparing said information for display; and
        (iv) constructing display specifications for displaying said information.

3. A computer-implemented method of providing computer-aided medical decision support comprising the steps of
    (A) initializing an inference engine;
    (B) initializing a semantic network structure;
    (C) initializing a discourse structure;
    (D) initializing a parser;
    (E) reading a lexicon file;
    (F) waiting for user input;
    (G) receiving a multimodal input from a user;
    (H) determining a type of input received, wherein it is determined that said type of input is a user question; and
    (I) processing said input based upon said determined type, wherein said processing step determines that said user question is not understood, and said processing step comprises the additional steps of
        (i) interrogating said discourse structure for context;
        (ii) formulating a clarifying question; and
        (iii) displaying said clarifying question.

4. A computer-implemented method of providing computer-aided medical decision support comprising the steps of
    (A) initializing an inference engine;
    (B) initializing a semantic network structure;
    (C) initializing a discourse structure;

(D) initializing a parser;
(E) reading a lexicon file;
(F) waiting for user input;
(G) receiving a multimodal input from a user;
(H) determining a type of input received, wherein it is determined that said type of input is a user question; and
(I) processing said input based upon said determined type, wherein said processing step determines that said user question is understood, and said processing step comprises the additional steps of
  (i) generating an abstract concept;
  (ii) storing said abstract concept in a discourse structure; and
  (iii) determining an action to take based upon said abstract concept.

5. A computer aided medical diagnostic decision support system comprising
  an interactive multimodal explanation generation system, wherein said interactive multimodal explanation generation system comprises
    a multimodal interactive user interface for receiving multimodal inputs from a user and for presenting multimodal outputs to the user;
    a knowledge representation module in communication with said multimodal interactive user interface and with said Bayesian network inference engine module; and
    a multimodal discourse module in communication with said knowledge representation module and with said multimodal interactive user interface,
  wherein said multimodal interactive user interface comprises an input module and an output module, said input module in communication with said knowledge representation module, and said output module in communication with said multimodal discourse module, and wherein said knowledge representation module further comprises
    a domain-specific lexicon;
    a chart parser;
    a semantic network structure; and
    processing logic to process the flow of data and commands between said input module, said multimodal discourse module, and said Bayesian network inference engine module.

6. A method of generating interactive multimodal explanations in a medical diagnostic support tool using a Bayesian network inference engine, said method comprising the steps of
  (A) waiting for an utterance from a user;
  (B) constructing an input object from the utterance, the input object identifying a modality, a sequence, and a content of the utterance;
  (C) inserting the input object into an input stream;
  (D) sending the input stream to a knowledge representation module; and
  (E) parsing and encoding the input object in the knowledge representation module into an abstract statement, defining a statement type, defining a statement origin, defining a statement modality, and defining a statement context for each input object.

7. A method of generating interactive multimodal medical explanations during a dialog between system participants, including a decision support tool and a user, the decision support tool using a Bayesian network inference engine, said method comprising the steps of
  (A) receiving multimodal inputs from a user;
  (B) synthesizing said multimodal inputs into a single sequenced stream of events;
  (C) communicating said sequenced stream of events to a knowledge representation module;
  (D) generating, within said knowledge representation module, an abstract statement from said sequenced stream of events, wherein step (D) further comprises the steps of
    (i) reading a lexicon file, comprising lexicon words and corresponding lexicon semantic word types;
    (ii) storing the lexicon words and corresponding lexicon semantic word types in a lexicon structure;
    (iii) parsing said sequenced stream of events into noun phrases and verb phrases;
    (iv) assigning a semantic type to each said parsed phrase;
    (v) storing said parsed phrases and their said assigned semantic phrase types in a chart data structure;
    (vi) comparing each said stored parsed phrase and its said assigned semantic phrase type from the chart data structure to the lexicon words and corresponding lexicon semantic word types stored in the lexicon structure trying to match patterns by trying to match general patterns followed by trying to match specific patterns; and
    (vii) generating said abstract statement for matched patterns; and
  (E) storing said abstract statement into an explicit discourse history structure comprising part of a multimodal discourse module.

8. A method of generating interactive multimodal medical explanations during a dialog between system participants, including a decision support tool and a user, the decision support tool using a Bayesian network inference engine, said method comprising the steps of
  (A) receiving multimodal inputs from a user;
  (B) synthesizing said multimodal inputs into a single sequenced stream of events;
  (C) communicating said sequenced stream of events to a knowledge representation module;
  (D) generating, within said knowledge representation module, an abstract statement from said sequenced stream of events, wherein step (D) further comprises the steps of
    (i) parsing said sequenced stream of events, wherein said parsing step comprises using a bottom-up parsing strategy; and
    (ii) encoding said parsed stream of events into said abstract statement, wherein said encoding step comprises generating a statement type, a statement origin, a statement modality, and a statement context for each abstract statement; and
  (E) storing said abstract statement into an explicit discourse history structure comprising part of a multimodal discourse module.

9. A method of generating interactive multimodal medical explanations during a dialog between system participants, including a decision support tool and a user, the decision support tool using a Bayesian network inference engine, said method comprising the steps of
  (A) receiving multimodal inputs from a user;
  (B) synthesizing said multimodal inputs into a single sequenced stream of events;
  (C) communicating said sequenced stream of events to a knowledge representation module;

(D) generating, within said knowledge representation module, an abstract statement from said sequenced stream of events, wherein step (D) further comprises the steps of
  (i) parsing said sequenced stream of events; and
  (ii) encoding said parsed stream of events into said abstract statement;
(E) storing said abstract statement into an explicit discourse history structure comprising part of a multimodal discourse module;
(F) using said multimodal discourse module to mediate an on-going dialog between the system participants based upon said discourse history structure;
(G) sending inquiries from said multimodal discourse module to said knowledge representation module;
(H) processing inquiries from said multimodal discourse module in said knowledge representation module;
(I) requesting, via said knowledge representation module, statistical processing by said Bayesian network inference engine;
(J) generating, within said knowledge representation module, said abstract statement based upon a result of said statistical processing;
(K) passing said abstract statement to said multimodal discourse module;
(L) determining, within said multimodal discourse module, a presentation strategy for presenting said result;
(M) communicating said presentation strategy to an output module; and
(N) presenting said result to the user via said output module.

10. The method of claim 9, wherein step (F) further comprises the steps of generating a plurality of dialog entries comprising command type information, modality type information, speaker type information, and context type information.

* * * * *